United States Patent [19]
Furuya et al.

[11] Patent Number: 6,140,325
[45] Date of Patent: *Oct. 31, 2000

[54] THIENOPYRIMIDINE DERIVATIVES, THEIR PRODUCTION AND USE

[75] Inventors: Shuichi Furuya; Nobuo Choh; Tetsuya Ohtaki, all of Tsukuba; Toshifumi Watanabe, Kawachinagano, all of Japan

[73] Assignee: Takeda Chemical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/723,151

[22] Filed: Sep. 30, 1996

Related U.S. Application Data

[63] Continuation of application No. PCT/JP96/02290, Aug. 13, 1996, which is a continuation-in-part of application No. 08/295,049, Aug. 26, 1994.

[30] Foreign Application Priority Data

| Aug. 19, 1993 | [JP] | Japan | 5-211972 |
| Jun. 29, 1994 | [JP] | Japan | 6-148126 |
| Aug. 17, 1995 | [JP] | Japan | 7-209498 |

[51] Int. Cl.$^7$ ............ A61K 31/519; C07D 495/04; C07D 519/00
[52] U.S. Cl. .................. 514/228.5; 514/234.2; 514/245; 514/249; 514/258; 514/261; 544/37; 544/61; 544/102; 544/117; 544/212; 544/237; 544/258; 544/277; 544/278
[58] Field of Search ............ 544/278, 61, 117, 544/277, 102; 514/258, 261, 228.5

[56] References Cited

FOREIGN PATENT DOCUMENTS

| 04044525 A3 | 12/1990 | European Pat. Off. . |
| 0 443 568 | 8/1991 | European Pat. Off. . |
| 0 510 526 | 10/1992 | European Pat. Off. . |
| 0 526 708 | 2/1993 | European Pat. Off. . |
| 0 640 606 | 3/1995 | European Pat. Off. . |
| 2 225485 | 9/1990 | Japan . |
| 276256 | 5/1996 | Switzerland . |
| WO 89/02432 | 3/1989 | WIPO . |
| 93/08799 | 5/1993 | WIPO . |
| WO 93/08799 | 5/1993 | WIPO . |

OTHER PUBLICATIONS

J. D. Elliot et al., "1.3–Diarylindan–2–carboxylic Acids, Potent and Selective Non–Peptide Endothelin Receptor Antagonists", J. Med. Chem. , vol. 37, (1994), pp. 1553–1557.

Boehm Chemical Abstracts, American Chemical Society, vol. 106, Jun. 1987, pp. 657–658, Abs 213890.

Documentation Abstracts Journal, Chemical Patents Index, Derwent Publications, Week 9244, Jan. 1993, pp. 1–2, for EP510526.

Documentation Abstracts Journal, Chemical Patents Index, Derwent Scientific and Patent Info., Week 9306, Apr. 1993, pp. 1–2, for AU 9218121.

Documentation Abstracts Journal, Chemical Patents Index, Derwent Publications, Week 8913, May 1989, pp. 1–2, for WO 89–02432.

Documentation Abstracts Journal, Chemical Patents Index, Derwent Publications, Week 9042, Dec. 1990, pp. 1–2, for JP 2–225485.

Boehm et al., "Ueber Theino–Verbindungen", (1986), pp. 661.

Chemical Abstracts, vol. 114, No. 11, Mar. 18, 1991, Columbus, Ohio, U.S.; Abstract No. 102035e.

Malamas Journal of Medicinal Chemistry, vol. 34, No. 4, Apr. 1991, pp. 1492–1503.

Clozel I, Nature, 365, 759 (1993).

Clozel II, A.J. Cardiovas. Pharm 22, (suppl. 8), 5377, (1993).

Stein, J., Med. Chem. 37, p. 329, (1994).

Doherty, J., Chem 35, 1493 (1992).

Nirei, Life Science 52, 1869 (1993).

Ihura, Life Science 50, 247 (1991).

Mihara, Eur. J. Pharm–Molec. Pharm 246, 33 (1993).

Aramori, Molecular Pharm. 43, 127 (1993).

Aramori, J. Biol. Chem 267, 12468 (1992).

Clozel, J. Pharm. Exp. Therapeutics 270, 228 (1994).

Fukuroda, Life Sci. 50, pp. pl107–pl112 (1992).

Williams, J. Biochem. Biophys. Nes. Comm 175, 556 (1991).

Kiowski, The Lancet 346, 732 (1995).

Koseki, Am. J. Physiology, 256, p.R858 (1989).

Watanabe, Circulation Research 69, p. 370 (1991).

Shibouta, Life Sci. 46, 1611 (1990).

Kanno, J.A.M.A. 264, 2868 (1990).

*Primary Examiner*—Mark L. Berch
*Attorney, Agent, or Firm*—Foley & Lardner

[57] ABSTRACT

Thienopyrimidine derivatives are disclosed. Also disclosed are methods for the production and use of these compounds.

42 Claims, No Drawings

THIENOPYRIMIDINE DERIVATIVES, THEIR PRODUCTION AND USE

This application is a continuation of PCT/JP96/02290 filed Aug. 13, 1996 which is a continuation-in-part of U.S. application Ser. No. 08/295,049, filed Aug. 26, 1994.

The substituent designations of the formulae according to the first embodiment may be the same or different than the substituent designations of formulae of the second embodiment.

TECHNICAL FIELD OF THE FIRST EMBODIMENT

The first embodiment of the present invention relates to endothelin antagonists containing thieno[2,3-d]pyrimidine derivatives. The first embodiment of the present invention also relates to thieno[2,3-d]pyrimidine derivatives. The first embodiment further relates to methods of manufacturing them.

BACKGROUND ART OF THE FIRST EMBODIMENT

The participation of endothelin has been suggested in adult diseases which have been increasing in recent years, particularly in those which are caused by ischemia such as cerebral infarction, angina pectoris, myocardial infarction and renal insufficiency. Endothelin is a peptide comprising 21 amino acids produced by endothelial cells and endothelin-1, endothelin-2 from which endothelin-3 have been obtained. In this specification, a group comprising these endothelins will be referred to as "endothelin".

It has been reported that endothelin exhibits the most powerful and long-lasting vasoconstrictive action, hypertensive activity and potentiating action for contraction of heart muscles among the natural and synthetic substances which were known hitherto. Such actions of the peptide have been thought to be due to the endothelin receptors which are thought to be present in smooth muscle membranes of the blood vessel and others. With regard to the endothelin receptors, endothelin-A receptor and endothelin-B receptor have been known. Hereinafter, they will be referred to as "endothelin receptors".

Accordingly, compounds having affinity for endothelin receptors while showing endothelin antagonistic activity have prophylactic and therapeutic effects against diseases which are caused by ischemia such as cerebral infarction, angina pectoris, myocardial infarction, renal insufficiency and liver insufficiency and thus development of these compounds has been greatly expected. With respect to compounds having an endothelin antagonistic action prepared by means of synthesis, those which are disclosed in the EP-A-510526 and 526708 and the PCT Gazette 9308799 have been known. However, the degree of endothelin antagonistic action of these compounds has not been satisfactory.

An object of the present invention is to offer endothelin antagonists containing thienopyrimidine derivatives exhibiting an excellent endothelin antago3nistic action, novel thienopyrimidine derivatives and methods of manufacturing them.

Under the above-mentioned circumstances, the present inventors have carried out extensive investigations in order to find novel compounds which can be used as endothelin antagonists and found that the thieno[2,3-d]pyrimidine derivatives exhibit an excellent endothelin antagonistic action. As a result of further investigations based upon such a finding, the present inventors have achieved the present invention.

SUMMARY OF THE INVENTION OF THE FIRST EMBODIMENT

Thus, the present invention provides a pharmaceutical composition for antagonizing endothelin containing thieno [2,3-d]pyrimidine derivatives. The present invention also provides novel thienopyrimidine derivatives and salts thereof. The present invention further provides methods for manufacturing thieno[2,3-d]pyrimidine derivatives.

More specifically, the present invention provides:

1. a pharmaceutical composition for antagonizing endothelin which comprises a compound of the formula (I):

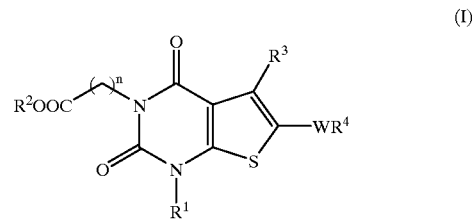

wherein each of $R^1$ and $R^2$ is hydrogen or an optionally-substituted hydrocarbon residue; $R^3$ is hydrogen or a group which is bonded through a carbon atom or nitrogen atom; $R^4$ is an optionally-substituted hydrocarbon residue; W is a chemical bond or a connecting group and n is an integer of 1–3, or a salt thereof and a pharmaceutically acceptable carrier, excipient or diluent;

2. a composition according to 1, wherein the composition is a prophylactic or therapeutic composition for acute renal insufficiency, myocardial infarction and/or liver insufficiency;

3. a composition according to 1, wherein the composition is prophylactic or therapeutic composition for hypofunction of an organ caused by its surgery or transplant;

4. a composition according to 3, wherein the organ is a liver;

5. a composition according to 1, wherein $R^1$ is hydrogen or optionally-substituted alkyl;

6. a composition according to 1, wherein $R^1$ is a group of the formula:

—(CH$_2$)mQ wherein m is an integer of 0–3, Q is optionally-substituted aryl, optionally-substituted cycloalkyl or an optionally-substituted heterocyclic group;

7. a composition according to 6, wherein Q is aryl which may be substituted by a group selected from the group consisting of (i) halogen, (ii) nitro, (iii) cyano, (iv) amino, (v) optionally-substituted carboxyl, (vi) lower alkylenedioxy, (vii) a group of the formula: —A—$R^5$ (in which A is a chemical bond or a connecting group; $R^5$ is lower alkyl);

8. a composition according to 7, wherein aryl is phenyl;

9. a composition according to 1, wherein $R^2$ is hydrogen or alkyl;

10. a composition according to 1, wherein $R^2$ is hydrogen;

11. a composition according to 1, wherein $R^3$ is hydrogen, alkyl, amino which may be mono- or di-substituted by alkyl or aryl;

12. a composition according to 1, wherein $R^3$ is lower alkyl;

13. a composition according to 1, wherein $R^4$ is optionally-substituted aryl, optionally-substituted cycloalkyl, an optionally-substituted heterocyclic group or carboxyl which may be esterified by alkyl;

14. a composition according to 1, wherein $R^4$ is aryl;

15. a composition according to 1, wherein the connecting group is a group of the formula: —SOf— (in which f is an integer of 0–2); a group of the formula: —CO—; or a group of the formula: —CONR$^6$— (in which $R^6$ is lower alkyl);

16. a composition according to 1, wherein the compound is selected from the group consisting of
2,4(1H,3H)-dioxo-5-methyl-6-(4-methoxymethoxyphenyl)-1-(2-methoxybenzyl)thieno[2,3-d]pyrimidine-3-acetic acid,
2,4(1H,3H)-dioxo-5-methyl-6-(4-methoxyphenyl)-1-(2-methylthiobenzyl)thieno[2,3-d]pyrimidine-3-acetic acid,
2,4(1H,3H)-dioxo-5-methyl-6-(4-methoxymethoxyphenyl)-1-(2-methylthiobenzyl)thieno[2,3-d]pyrimidine-3-acetic acid,
2,4(1H,3H)-dioxo-5-methyl-6-(4-methylthiomethoxyphenyl)-1-(2-methylthiobenzyl)thieno[2,3-d]pyrimidine-3-acetic acid,
2,4(1H,3H)-dioxo-5-methyl-6-(4-methylthiomethoxyphenyl)-1-(2-methoxybenzyl)thieno[2,3-d]pyrimidine-3-acetic acid,
2,4(1H,3H)-dioxo-5-methyl-1-(2-methylthiobenzyl)-6-(4-propoxyphenyl)thieno[2,3-d]pyrimidine-3-acetic acid and
2,4(1H,3H)-dioxo-5-methyl-1-(2-methylthiobenzyl)-6-[4-(2-oxopropoxy)phenyl]thieno[2,3-d]pyrimidine-3-acetic acid;

17. a compound of the formula (I'):

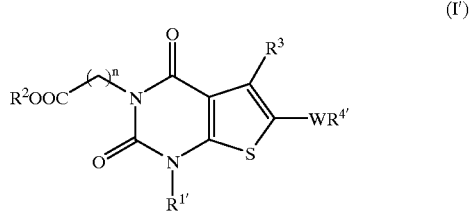

(I')

wherein $R^{1'}$ is hydrogen, lower alkyl or a group of the formula: —(CH2)mQ' {in which m is an integer of 0–3, Q' is aryl which may be substituted by (i) halogen, (ii) nitro, (iii) cyano, (iv) amino, (v) optionally-substituted carboxyl, (vi) lower alkylenedioxy or (vii) a group of the formula: —A—$R^6$ (in which A is a chemical bond or a connecting group, $R^6$ is lower alkyl), an optionally-substituted cycloalkyl or an optionally-substituted heterocyclic group}; $R^2$ is hydrogen or an optionally-substituted hydrocarbon residue; $R^3$ is hydrogen or a group bonded through a carbon atom or through a nitrogen atom; $R^{4'}$ is aryl, cycloalkyl, a heterocyclic group or a group of the formula: —COOR$^{5'}$ (in which $R^{5'}$ is hydrogen or lower alkyl) wherein each of them may be substituted; W is a chemical bond or a connecting group and n is an integer of 1–3, or a salt thereof;

18. a compound according to 17, wherein Q' is a group of the formula: —A—$R^5$ (in which A is a chemical bond or a connecting group; $R^5$ is lower alkyl);

19. a compound according to 17, wherein $R^{1'}$ is benzyl which may be substituted by a group of the formula: —A—$R^5$: (wherein A is a chemical bond or a connecting group; $R^5$ is lower alkyl);

20. a compound according to 17, wherein $R^2$ is hydrogen or alkyl;

21. a compound according to 17, wherein $R^2$ is hydrogen;

22. a compound according to 17, wherein $R^1$ is hydrogen, alkyl or amino which may be mono- or di-substituted by alkyl or aryl;

23. a compound according to 17, wherein $R^3$ is lower alkyl;

24. a compound according to 17, wherein $R^{4'}$ is optionally-substituted aryl;

25. a compound according to 17, wherein $R^{4'}$ is aryl which may be substituted by alkoxy or alkylthio;

26. a compound according to 17, wherein the connecting group is a group of the fomula: —SOf— (wherein f is an integer of 0–2); a group of the formula: —CO—; or a group of the formula: —CONR$^6$— (in which $R^6$ is lower alkyl);

27. a compound according to 17, wherein the compound is selected from the group consisting of
2,4(1H,3H)-dioxo-5-methyl-6-(4-methoxymethoxyphenyl)-1-(2-methoxybenzyl)thieno[2,3-d]pyrimidine-3-acetic acid,
2,4(1H,3H)-dioxo-5-methyl-6-(4-methoxyphenyl)-1-(2-methylthiobenzyl)thieno[2,3-d]pyrimidine-3-acetic acid,
2,4(1H,3H)-dioxo-5-methyl-6-(4-methoxymethoxyphenyl)-1-(2-methylthiobenzyl)thieno[2,3-d]pyrimidine-3-acetic acid,
2,4(1H,3H)-dioxo-5-methyl-6-(4-methylthiomethoxyphenyl)-1-(2-methylthiobenzyl)thieno[2,3-d]pyrimidine-3-acetic acid,
2,4(1H,3H)-dioxo-5-methyl-6-(4-methylthiomethoxyphenyl)-1-(2-methoxybenzyl)thieno[2,3-d]pyrimidine-3-acetic acid,
2,4(1H,3H)-dioxo-5-methyl-1-(2-methylthiobenzyl)-6-(4-propoxyphenyl)thieno[2,3-d]pyrimidine-3-acetic acid and
2,4(1H,3H)-dioxo-5-methyl-1-(2-methylthiobenzyl)-6-[4-(2-oxopropoxy)phenyl]thieno[2,3-d]pyrimidine-3-acetic acid;

28. a method for producing a compound according to 17 in which $R^{1'}$ is hydrogen and $R^2$ is an optionally-substituted hydrocarbon residue, which comprises subjecting a compound of the formula (II):

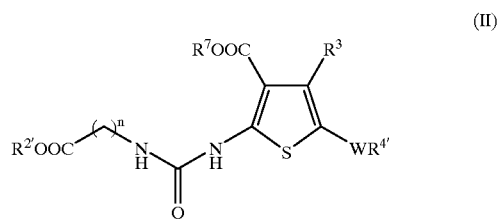

(II)

wherein $R^{2'}$ is an optionally-substituted hydrocarbon residue; $R^3$ is hydrogen, a group bonded through a carbon atom or through a nitrogen atom; $R^{4'}$ is aryl, cycloalkyl, a heterocyclic group or a group of the formula: —COOR$^{5'}$ (in which $R^{5'}$ is hydrogen or lower alkyl) wherein each of them may be substituted; $R^7$ is hydrogen or an optionally-substituted hydrocarbon residue; W is a chemical bond or a connection group; n is an integer of 1–3, or its salt to react with a base;

29. a method for producing a compound according to 17 in which $R^{1'}$ is hydrogen and $R^2$ is an optionally-substituted hydrocarbon residue, which comprises subjecting a compound of the formula (III):

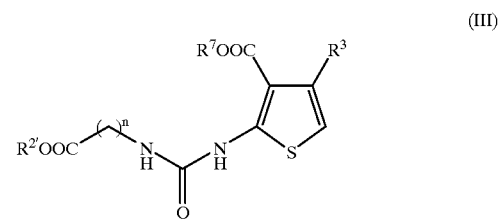

(III)

wherein $R^{2'}$ is an optionally-substituted hydrocarbon residue; $R^3$ is hydrogen, a group bonded through a carbon atom or through a nitrogen atom; $R^{4'}$ is aryl, cycloalkyl, a heterocyclic group or a group of the formula: —COOR$^{5'}$ (in which R$^{5'}$ is hydrogen or lower alkyl) wherein each of them may be substituted; R$^7$ is hydrogen or an optionally-substituted hydrocarbon residue; W is a chemical bond or a connecting group; n is an integer of 1–3, or its salt to react with a base, and subjecting the resulting product to an electrophilic substitution reaction;

30. a method for producing a compound according to 17 in which R$^{1'}$ is lower alkyl or a group of the formula: —(CH2)mQ' [in which m is an integer of 0–3, Q' is aryl which may be substituted by (i) halogen, (ii) nitro, (iii) cyano, (iv) amino, (v) optionally-substituted carboxyl, (vi) lower alkylenedioxy or (vii) a group of the formula: —A—R$^6$ (wherein A is a chemical bond or a connecting group, R$^6$ is lower alkyl), an optionally-substituted cycloalkyl or an optionally-substituted heterocyclic group] and R$^2$ is an optionally-substituted hydrocarbon residue, which comprises subjecting a compound of the formula (IV):

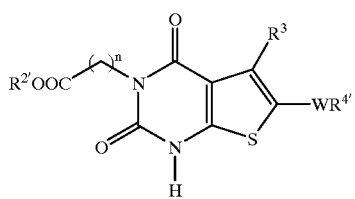

(IV)

wherein R$^{2'}$ is an optionally-substituted hydrocarbon residue; R$^3$ is hydrogen, a group bonded through a carbon atom or through a nitrogen atom; R$^{4'}$ is aryl, cycloalkyl, a heterocyclic group or a group of the formula: —COOR$^{5'}$ (in which R$^{5'}$ is hydrogen or lower alkyl) wherein each of them may be substituted; W is a chemical bond or a connecting group; n is an integer of 1–3, or its salt to react with a compound of the formula (V):

R$^{1''}$—X    (V)

wherein R$^{1''}$ is lower alkyl or a group of the formula: —(CH2)mQ' {in which m is an integer of 0–3, Q' is aryl which may be substituted by (i) halogen, (ii) nitro, (iii) cyano, (iv) amino, (v) optionally-substituted carboxyl, (vi) lower alkylenedioxy or (vii) a group of the formula: —A—R$^6$ (in which A is a chemical bond or a connecting group, R$^1$ is lower alkyl), an optionally-substituted cycloalkyl or an optionally-substituted heterocyclic group} and X is halogen, or its salt;

31. use of a compound as defined in 1 for producing a pharmaceutical composition for antagonizing endothelin activity in a mammal suffering from an endothelin-derived disorder;

32. use according to 31, wherein the endothelin-derived disorder is selected from the group consisting of acute renal insufficiency, cardiac infarction and/or liver insufficiency;

33. use according to 31, wherein the endothelin-derived disorder is hypofunction of an organ caused by its surgery or transplant; and 34. use according to 33, wherein the organ is a liver.

DETAILED DESCRIPTION OF THE INVENTION OF THE FIRST EMBODIMENT

The compounds of the present invention and the starting material compounds used for the production of them (hereinafter, both may be referred to as "the compounds of the present application" in some cases) will be illustrated in more detail.

The above-mentioned n is preferably 1 or 2 and, particularly preferably, it is 1.

Examples of the hydrocarbon residue in the optionally-substituted hydrocarbon residue shown by the above-mentioned R$^1$, R$^2$, R$^{2'}$, R$^4$ and R$^7$ are alkyl (e.g. C$_{1-6}$ alkyl such as methyl, ethyl, propyl, isopropyl, butyl, tert-butyl, pentyl, hexyl, etc.), cycloalkyl (e.g. C$_{3-6}$ cycloalkyl such as cyclopropyl, cyclopentyl, cyclohexyl, etc.), alkoxyalkyl (e.g. C$_{1-3}$ alkoxy C$_{1-6}$ alkyl such as methoxymethyl, ethoxymethyl, ethoxybutyl, propoxymethyl, propoxyhexyl, etc.), hydroxyalkyl (e.g. hydroxy C$_{1-6}$ alkyl such as hydroxymethyl, hydroxyethyl, hydroxybutyl, hydroxypropyl, etc.), alkenyl (e.g. C$_{2-6}$ alkenyl such as vinyl, butadienyl, hexatrienyl, etc.), formyl, carboxyl, alkoxycarbonyl (e.g. C$_{1-6}$ alkoxycarbonyl such as methoxycarbonyl, ethoxycarbonyl, tert-butoxycarbonyl, etc.), aryl (e.g. C$_{6-14}$ aryl such as phenyl, naphthyl, anthracenyl, etc.), aralkyl (e.g. C$_{7-20}$ aralkyl such as benzyl, benzhydryl, trityl, etc.) and the like.

Examples of the substituent that said hydrocarbon residue may have are nitro, hydroxyl, oxo, thioxo, cyano, carbamoyl, carboxyl, C$_{1-4}$ alkoxy-carbonyl (e.g. methoxycarbonyl, ethoxycarbonyl, etc.), sulfo, halogen (e.g. fluorine, chlorine, bromine and iodine), C$_{1-6}$ alkoxy (e.g. methoxy, ethoxy, propoxy, isopropoxy, butoxy, isobutoxy, sec-butoxy, tert-butoxy, etc.), C$_{6-12}$ aryloxy (e.g. phenoxy; etc.), halogeno C$_{6-16}$ aryl (e.g. o-, m- or p-chlorophenoxy, o-, m- or p-bromophenoxy, etc.), C$_{1-6}$ alkylthio (e.g. methylthio, ethylthio, n-propylthio, isopropylthio, n-butylthio, tert-butylthio, etc.), C$_{6-12}$ arylthio (e.g. phenylthio, etc.), C$_{1-6}$ alkylsulfinyl (e.g. methylsulfinyl, ethylsulfinyl, etc.), C$_{1-6}$ alkylsulfonyl (e.g. methylsulfonyl, ethylsulfonyl, etc.), amino, C$_{1-6}$ acylamino (e.g. formylamino, acetylamino, propionylamino, etc.), mono- or di-C$_{1-4}$ alkylamino (e.g. methylamino, ethylamino, n-propylamino, isopropylamino, n-butylamino, dimethylamino, diethylamino, etc.), C$_{1-6}$ acyl (e.g. formyl, acetyl, hexanoyl, etc.), C$_{6-12}$ aryl-carbonyl (e.g. benzoyl, etc.), a five- or six-membered heterocyclic group having one to four heteroatom(s) selected from oxygen, sulfur, nitrogen, etc. besides carbon atoms (e.g. 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidyl, 3- or 4-pyridanidyl, quinolyl, isoquinolyl, indolyl, etc.) which may be susbtituted with one to four substituent(s) selected from (a) halogen (e.g. fluorine, bromine, chlorine and iodine), (b) C$_{1-4}$ alkyl (e.g. methyl, ethyl, propyl, isopropyl, etc.) and (c) halogenophenoxy (e.g. o-, m- or p-chlorophenoxy, o-, m- or p-bromophenoxy, etc.), C$_{1-10}$ haloalkyl (e.g. difluoromethyl, trifluoromethyl, trifluoroethyl, trichloroethyl, etc.), and the like. One to five substituent(s) selected from the above may be used. When the hydrocarbonyl group is cycloalkyl, cycloalkenyl, aryl or aralkyl, the substituent may be C$_{1-6}$ alkyl (e.g. methyl, ethyl, propyl, isopropyl, butyl, etc.). Number of the substituent may be from noe to six or, preferably, one to three.

Examples of the above-mentioned optionally-substituted group bonded through a carbon atom shown by R$^3$ are alkyl (e.g. C$_{1-6}$ alkyl such as methyl, ethyl, propyl, isopropyl, butyl, tert-butyl, pentyl, hexyl, etc.), cycloalkyl (e.g. C$_{3-6}$ cycloalkyl such as cyclopropyl, cyclopentyl, cyclohexyl, etc.), alkoxyalkyl (e.g. C$_{1-3}$ alkoxy C$_{1-6}$ alkyl such as methoxymethyl, ethoxymethyl, ethoxybutyl, propoxymethyl, propoxyhexyl, etc.), hydroxyalkyl (e.g.. hydroxy C$_{1-6}$ alkyl such as hydroxymethyl, hydroxyethyl, hydroxybutyl, hydroxypropyl, etc.), alkenyl (e.g. $C_{2-6}$ alkenyl such as vinyl, butadienyl, hexatrienyl, etc.), formyl, carboxyl, alkoxycarbonyl (e.g. $C_{1-6}$ alkoxycarbonyl such as methoxycarbonyl, ethoxycarbonyl, tert-butoxycarbonyl, etc.), cyano, amido, mono- or dialkylcarbamoyl (e.g. mono- or di-$C_{1-6}$ alkylcarbamoyl such as methylcarbamoyl, ethylcarbamoyl, hexylcarbamoyl, dimethylcarbamoyl, methylethylcarbamoyl, etc.), amidino, aryl (e.g. $C_{6-14}$ aryl such as phenyl, naphthyl, anthryl, etc.), aralkyl (e.g. $C_{7-20}$ aralkyl such as benzyl, benzhydryl, trityl, etc.), a heterocyclic group having a linkage to a carbon atom {e.g. a five- to eight-membered ring having one to four heteroatom(s) such as oxygen atom, sulfur atom, nitrogen atom, etc. besides carbon atom or a condensed said ring [e.g. a five-membered group having one to four hetero atom(s) selected from oxygen, sulfur, nitrogen, etc. besides carbon atom (e.g. 2- or 3-thienyl, 2- or 3-furyl, 2- or 3-pyrrolyl, 2-, 4- or 5-oxazolyl, 2-, 4- or 5-thiazolyl, 3-, 4- or 5-pyrazolyl pyrrolidinyl, 2-, 4- or 5-imidazolyl, 3- 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, etc.); a six-membered ring having one to four hetero atom(s) selected from oxygen atom, sulfur atom, nitrogen atom, etc. besides carbon atom (e.g. 2-, 3- or 4-pyridyl, N-oxido-2-, 3- or 4-pyridyl; 2-, 4- or 5-pyrimidinyl, N-oxido-2-, 4- or 5-pyrimidinyl, 2- or 3-thiomorpholinyl, 2- or 3-morpholinyl, piperidyl, pyranyl, thiopyranyl, 1,4-oxazinyl, 1,4-thiazinyl, 1,3-thiazinyl, 2- or 3-piperazinyl, triazinyl, oxotriazinyl, 3- or 4-pyridazinyl, pyrazinyl, N-oxido-3- or 4-pyridazinyl, etc.); a bicyclic or tricyclic condensed ring having one to four hetero atom(s) selected from oxygen atom, sulfur atom, nitrogen atom, etc. besides carbon atom (e.g. benzofuryl, benzothiazolyl, benzoxazolyl, pyrrolo[1,2-b]pyridazinyl, pyrazolo[1,5-b]pyridyl, imidazo[1,2-a]pyridyl, triazolo[4,5-b]pyridazinyl, imidazo[1,2-b]pyridazinyl, 1,2,4-triazolo[4,3-a]pyridyl, benzimidazolyl, quinolyl, isoquinolyl, cinnolinyl, phthalazinyl, quinazolinyl, quinoxalinyl, indolidinyl, quinolidinyl, 1,8-naphthylidinyl, purinyl, pteridinyl, dibenzofuranyl, carbazolyl, acridinyl, phenanthridinyl, chromanyl, benzoxazinyl, phenazinyl, phenothiazinyl, phenoxazinyl, phthalazinyl, naphthyridiryl, phenoxathiinyl, phenanthrolinyl, thianthrenyl, etc.), etc.] and the like.

Examples of the substituent that the above-mentioned group bonded through a carbon atom may have are $C_{6-14}$ aryl (e.g. phenyl, naphthyl, etc.) which may be substituted with one to four group(s) selected from (a) hydroxyl, (b) amino, (c) mono- or di-$C_{1-6}$ alkylamino (e.g. methylamino, ethylamino, propylamino, dimethylamino, diethylamino, etc.), (d) $C_{1-6}$ alkoxy (e.g. methoxy, ethoxy, propoxy, hexyloxy, etc.) and (e) halogen (e.g. fluorine, chlorine, bromine and iodine); mono- or di-$C_{1-6}$ alkylamino (e.g. methylamino, ethylamino, propylamino, dimethylamino, diethylamino, etc.); $C_{1-4}$ acylamino (e.g. formylamino, acetylamino, etc.); hydroxyl; carboxyl; nitro; $C_{1-6}$ alkoxy (e.g. methoxy, ethoxy, propoxy, isopropoxy, butoxy, etc.); $C_{1-6}$ alkyl-carbonyloxy (e.g. acetoxy, ethylcarbonyloxy, etc.); halogen (e.g. fluorine, chlorine, bromine and iodine); an. optionally-substituted nitrogen-containing group which will be mentioned later; and the like. Numbers of the substituent(s) are from one to six or, preferably, from one to three.

Examples of the above-mentioned optionally-substituted group bonded through a nitrogen atom expressed by $R^3$ are amino, —$NR^8R^9$ [in which $R^8$ is hydrogen, alkyl, cycloalkyl, aryl or a heterocyclic group and $R^9$ is hydrogen or alkyl], a heterocyclic group having a linkage on a nitrogen atom (e.g. 1H-1-pyrrolyl, 1-imidazolinyl, pyrazolyl, indolyl, 1H-1-indazolyl, 7-purinyl, 1-pyrrolidinyl, 1-pyrrolinyl, 1-imidazolinyl, pyrazolidinyl, piperazinyl, pyrazolinyl, 1-piperidinyl, 4-morpholinyl, 4-thiomorpholinyl, etc.) and the like. The above-mentioned alkyl, cycloalkyl, aryl and a heterocyclic group have the same meanings as defined already.

Examples of the substituent that said group connected by a nitrogen atom has are $C_{1-6}$ alkyl (e.g. methyl, ethyl, propyl, isopropyl, butyl, isobutyl, sec-butyl, tert-butyl, etc.), $C_{2-6}$ alkenyl (e.g. vinyl, 1-methylvinyl, 1-propenyl, allyl, etc.), $C_{2-6}$ alkynyl (e.g. ethynyl, 1-propynyl, propargyl, etc.), $C_{3-6}$ cycloalkyl (e.g. cyclopropyl, cyclobutyl, cyclopentyl, cyclohexyl, etc.), $C_{5-7}$ cycloalkenyl (e.g. cyclopentenyl, cyclohexenyl, etc.), $C_{7-11}$ aralkyl (e.g. benzyl, alpha-methylbenzyl, phenethyl, etc.), $C_{6-14}$ aryl (e.g. phenyl, naphthyl, etc.), $C_{1-6}$ alkoxy (e.g. methoxy, ethoxy, propoxy, isopropoxy, n-butoxy, isobutoxy, sec-butoxy, tert-butoxy, etc.), $C_{6-14}$ aryloxy (e.g. phenoxy, etc.), $C_{1-6}$ alkanoyl (e.g. formyl, acetyl, propionyl, n-butyryl, isobutyryl, etc.), $C_{6-14}$ aryl-carbonyl (e.g. benzoyl, etc.), $C_{1-6}$ alkanoyloxy (e.g. formyloxy, acetyloxy, propionyloxy, n-butyryloxy, isobutyryloxy, etc.) $C_{6-14}$ aryl-carbonyloxy (e.g. benzoyloxy, etc.), carboxyl, $C_{1-6}$ alkoxy-carbonyl (e.g. methoxycarbonyl, ethoxycarbonyl, n-propoxycarbonyl, isopropoxycarbonyl, n-butoxycarbonyl, isobutoxycarbonyl, tert-butoxycarbonyl, etc.), carbamoyl, N-mono-$C_{1-4}$ alkyl-carbamoyl (e.g. N-methylcarbamoyl, N-ethylcarbamoyl, N-propylcarbamoyl, N-isopropylcarbamoyl, N-butylcarbamoyl, etc.), N,N-di-$C_{1-4}$ alkylcarbamoyl (e.g. N,N-dimethylcarbamoyl, N,N-diethylcarbamoyl, N,N-dipropylcarbamoyl, N,N-dibutylcarbamoyl, etc.), cyclic aminocarbonyl (e.g. 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl, etc.), halogen (e.g. fluorine, chlorine, bromine and iodine), mono-, di- or tri-halogeno-$C_{1-4}$ alkyl (e.g. chloromethyl, dichloromethyl, trifluoromethyl, trifluoroethyl, etc.), oxo, amidino, imino, amino, mono- or di-$C_{1-4}$ alkylamino (e.g. methylamino, ethylamino, propylamino, isopropylamino, butylamino, dimethylamino, diethylamino, dipropylamino, diisopropylamino, dibutylamino, etc.), a three- to six-membered heterocyclic amino group which may have one to three hetero atom(s) selected from oxygen, sulfur, nitrogen, etc. besides carbon atoms and one nitrogen atom (e.g. aziridinyl, azetidinyl, pyrrolidinyl, pyrrolinyl, pyrrolyl, imidazolyl, pyrazolyl, imidazolinyl, piperidino, morpholino, dihydropyridyl, pyridyl, N-methylpiperazinyl, N-ethylpiperazinyl, etc.), $C_{1-6}$ alkanoylamino (e.g. formamido, acetamido, trifluoroacetamido, propionylamido, butyrylamido, isobutyrylamido, etc.), benzamido, carbamoylamino, N-$C_{1-4}$ alkylcarbamoylamino (e.g. N-methylcarbamoylamino, N-ethylcarbamoylamino, N-propylcarbamoylamino, N-isopropylcarbamoylamino, N-butylcarbamoylamino, etc.), N,N-di-$C_{1-4}$ alkylcarbamoylamino (e.g. N,N-dimethylcarbamoylamino, N,N-diethylcarbamoylamino, N,N-dipropylcarbamoylamino, N,N-dibutylcarbamoylamino, etc.), $C_{1-3}$ alkylenedioxy (e.g. methylenedioxy, ethylenedioxy, etc.), —$B(OH)_2$, hydroxyl, epoxy (—O—), nitro, cyano, mercapto, sulfo, sulfino, phosphono, dihydroxyboryl, sulfamoyl, $C_{1-6}$ alkylsulfamoyl (e.g. N-methylsulfamoyl, N-ethylsulfamoyl, N-propylsulfamoyl, N-isopropylsulfamoyl, N-butylsulfamoyl, etc.), di-$C_{1-6}$ alkylsulfamoyl (e.g. N,N- dimethylsulfamoyl, N,N-diethylsulfamoyl, N,N-dipropylsulfamoyl, N,N-dibutylsulfamoyl, etc.), $C_{1-6}$ alkylthio (e.g. methylthio, ethylthio, propylthio, isopropylthio, n-butylthio, sec-butylthio, tert-butylthio, etc.), phenylthio, $C_{1-6}$ alkylsulfinyl (e.g. methylsulfinyl, ethylsulfinyl, propylsulfinyl, butylsulfinyl, etc.), phenylsulfinyl, $C_{1-6}$ alkylsulfonyl (e.g. methylsulfonyl, ethylsulfonyl, propylsulfonyl, butylsulfonyl, etc.), phenylsulfonyl, and the like. Numbers of the substituent(s) are from one to six or, preferably, from one to three.

Examples of the aryl group in the above-mentioned optionally-substituted aryl expressed by $R^{4'}$ are monocyclic or condensed polycyclic aromatic hydrocarbon groups. Preferred examples are $C_{6-14}$ aryl such as phenyl, naphthyl, anthryl, phenanthryl, acenaphthylenyl, etc. and the particularly preferred ones among them are phenyl, 1-naphthyl, 2-naphthyl, etc.

Said aryl may have one or more (preferably from one to three) suitable substituent(s) and examples of such substituent(s) are alkyl having 1–3 carbons (e.g. methyl, ethyl, propyl, etc.), alkenyl having 2–4 carbons (e.g. vinyl, allyl, 2-butenyl, etc.), lower alkynyl having 3–4 carbons (e.g. propargyl, butan-2-ynyl, etc.), cycloalkyl having 3–7 carbons (e.g. cyclopropyl, cyclobutyl, cyclopentyl, cyclohexyl, etc.), aryl (e.g. phenyl, naphthyl, etc.), a five- to nine-membered aromatic heterocyclic group having one to four hetero atoms selected from nitrogen, oxygen and sulfur (e.g. furyl, thienyl, pyrrolyl, thiazolyl, imidazolyl, pyrazolyl, pyridyl, etc.), a five- to nine-membered nonaromatic heterocyclic group having one to four hetero atoms selected from nitrogen, oxygen and sulfur (e.g. oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.), aralkyl having 7–10 carbons (e.g. benzyl, phenethyl, etc.), amino, N-monosubstituted amino (e.g. monoalkylamino having 1–6 carbons such as methylamino, ethylamino, propylamino, etc.), N,N-disubstituted amino (e.g. N,N-disubstituted amino wherein the substituents are the alkyls having 2–6 carbons such as dimethylamino, diethylamino, etc.), amidino, acyl (e.g. arylcarbonyl having 1–8 carbons such as acetyl, propionyl, butyryl, etc.; arylcarbonyl having 6–14 carbons such as benzoyl, etc.; and the like), carbamoyl, N-monosubstituted carbamoyl (e.g. alkylcarbamoyl having 1–6 carbons such as methylcarbamoyl, ethylcarbamoyl, propylcarbamoyl, etc.), N,N-disubstituted carbamoyl (e.g. N,N-disubstituted carbamoyl substituted with alkyls having 1–6 carbons such as dimethylcarbamoyl, diethylcarbamoyl, etc.), sulfamoyl, N-monosubstituted sulfamoyl (e.g. N-alkylsulfamoyl substituted with alkyl having 1–6 carbons such as methylsulfamoyl, ethylsulfamoyl, propylsulfamoyl, etc.), N,N-disubstituted sulfamoyl (e.g. N,N-disubstituted sulfamoyl substituted with alkyls having 1–6 carbons such as dimethylsulfamoyl, diethylsulfamoyl, etc.), carboxyl, alkoxycarbonyl having 1–3 carbons (e.g. methoxycarbonyl, ethoxycarbonyl, etc.), hydroxyl, optionally-substituted alkoxy having 1–3 carbons in which the substituent is, for example, $C_{1-3}$ lower alkyl halogen, $C_{1-3}$ alkylthio, hydroxyl, etc. (e.g. methoxy, ethoxy, propoxy, etc.), alkenyloxy having 2–4 carbons (e.g. vinyloxy, allyloxy, etc.), cycloalkyloxy (e.g. cycloalkyloxy having 3–7 carbons such as cyclopropyloxy, cycloethyloxy, etc.), aralkyloxy (e.g. aralkyloxy having 7–10 carbons such as benzyloxy, etc.), aryloxy (e.g. phenyloxy, naphthyloxy, etc.), mercapto, alkylthio having 1–3 carbons (e.g. methylthio, ethylthio, propylthio, etc.), aralkylthio (e.g. aralkylthio having 7–10 carbons such as benzylthio, etc.), arylthio (e.g. phenylthio, naphthylthio, etc.), lower alkylenedioxy having 1–3 carbons (e.g. methylenedioxy, ethylenedioxy, propylenedioxy, etc.), sulfo, cyano, azido, nitro, nitroso, a halogen atom (e.g. fluorine, chlorine, bromine, iodine, etc.), and the like.

Examples of the cycloalkyl in the optionally-cycloalkyl shown by the above-mentioned $R^{4'}$ and Q' are cycloalkyl having 3–10 carbons and bicycloalkyl having 3–10 carbons. Preferable examples thereof are cyclopropyl, cyclobutyl, cyclopentyl, cyclohexyl, cycloheptyl, cyclooctyl, bicyclo[2,2,1]heptyl, bicyclo[2,2,2]octyl, bicyclo[3,2,1]octyl, bicyclo[3,2,1]nonyl, bicyclo[4,2,1]nonyl, bicyclo[4,3,1]decyl, etc. Among them, cyclopentyl and cyclohexyl are preferred.

The substituent for said cycloalkyl has the same meaning as that for the above-mentioned aryl.

Examples of the heterocyclic group in the optionally-substituted heterocylic group shown by the above-mentioned $R^{4'}$ and Q' are a five- to thirteen-membered aromatic heterocyclic group having one to four heteroatoms selected from oxygen (O), sulfur (S) and nitrogen (N) as the atom for constituting the ring (atom in the ring) or a saturated or unsaturated nonaromatic heterocyclic group (aliphatic heterocyclic group).

Examples of the preferred aromatic heterocyclic group are aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4 -thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl; and aromatic fused heterocyclic group such as benzofuranyl, isobenzofuranyl, benzo[b]thienyl, indolyl, isoindolyl, 1H-indazolyl, benzoimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, alpha-carbolinyl, beta-carbolinyl, gamma-carbolinyl, acridinyl, phenoxazinyl, phenothiazinyl, phenazinyl, phenoxathinyl, thianthrenyl, phenathridinyl, phenathrolinyl, indolidinyl, pyrrolo[1,2-b]pyridazinyl, pyrazoloro[1,5-a]pyridyl, imidazo[1,2-a]pyridyl, imidazo[1,5-a]pyridyl, imidazol[1,2-b]pyridazinyl, imidazo[1,2-a]pyrimidinyl, 1,2,4-triazolo[4,3-a]pyridyl and 1,2,4-triazolo[4,3-b]pyridazinyl.

Preferable examples of the nonaromatic heterocyclic group include oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl.

Said heterocyclic group may have one or more (preferably, one to three) suitable substituent(s) and said substituents are the same as those for the above-mentioned aryl group.

Examples of the substituent for the optionally-substituted carboxyl in the above-mentioned Q' are alkyl, cycloalkyl, aryl, aryl, aralkyl and heterocyclic group and they have the same meanings as mentioned already.

Examples of the lower alkylenedioxy in the above-mentioned Q' are $C_{1-6}$ alkylenedioxy (e.g. methylenedioxy, ethylenedioxy, propoylenedioxy and 2,3-dimethylmethylenedioxy).

The aryl group in the above-mentioned Q' has the same meaning as that mentioned already.

Examples of the lower alkyl expressed in the above-mentioned $R^{1'}$, $R^{1''}$, $R^5$, $R^{5'}$ and $R^6$ are $C_{1-6}$ alkyl (e.g. methyl, ethyl, propyl, isopropyl, butyl, tert-butyl, pentyl, hexyl, etc.).

Examples of the above-mentioned connecting group shown by W and A are $C_{1-4}$ alkylene (e.g. methylene, ethylene, etc.), $C_{1-6}$ alkenylene (e.g. vinylene, butadienylene, etc.), —(CH$_2$)$_c$NR$^{10}$— (in which c is an integer of 0–3 and R$^{10}$ is hydrogen or $C_{1-6}$ alkyl such as methyl, ethyl, butyl, etc.), —CO—, a group of the formula: —CONR$^{10}$— (in which R$^{10}$ has the same meaning as defined above), —O—, —S—, a group of the formula: —NR$^{10}$SO$_e$— (in which e is an integer of 0–2 and R$^{10}$ has the same meaning as defined above), and the like.

Preferably, R$^1$ is hydrogen or optionally-substituted alkyl. More preferably, R$^1$ is hydrogen or a group of the formula: —(CH$_2$)$_m$Q (in which m is an integer of 0–3 and Q is an optionally-substituted aryl, optionally-substituted cycloalkyl or an optionally-substituted heterocyclic group). Examples of alkyl in the above-mentioned optionally substituted alkyl are $C_{1-6}$ alkyl (e.g. methyl, ethyl, propyl, butyl, t-butyl, hexyl, etc.), more preferably $C_{1-3}$ alkyl. The above-mentioned optionally-susbtituted aryl, optionally-substituted cycloalkyl and optionally-substituted heterocyclic group are the same meanings as defined above. Q is preferably aryl which may be substituted by (i) hologen, (ii) nitro, (iii) cyano, (iv) amino, (v) optionally-substituted carboxyl, (vi) lower alkylenedioxy, (vii) a group of the formula: —A—R$^6$ (in which A and R$^6$ are the same meaning as defined above). The optionally-substituted carboxyl and lower alkylenedioxy are the same meaning as defined above. The aryl is preferably $C_{6-12}$ aryl (e.g. phenyl, naphthyl, etc), more preferably phenyl.

Preferably, R$^2$ is hydrogen or alkyl. More preferably, R$^2$ is hydrogen or $C_{1-6}$ alkyl (e.g. methyl, ethyl, propry, butyl, t-butyl, hexyl, etc.). Most preferably, R$^2$ is hydrogen.

Preferably R$^3$ is hydrogen, alkyl or amino which may be mono-/di-substituted by alkyl or aryl. More preferably, R$^3$ is $C_{1-6}$ alkyl (e.g. methyl, ethyl, propyl, butyl, t-butyl, hexyl, etc.). Most preferably, R$^3$ is $C_{1-3}$ alkyl (e.g. methyl, ethyl, propyl, etc.). Alkyl, in the amino which may be mono-/di-substituted by alkyl or aryl, is preferably $C_{1-4}$ alkyl (e.g. methyl, ethyl, propyl, butyl, etc.). Aryl, in the amino which may be mono-/di-substituted by alkyl or aryl, is preferably $C_{6-12}$ aryl (e.g. phenyl, naphthyl, etc.).

Preferably, R$^4$ is optionally-substituted aryl, optionally-substituted cycloalkyl, an optionally-substituted heterocyclic group or optionally-substituted carboxyl which may be esterified by alkyl (e.g. $C_{1-6}$ alkyl such as methyl, ethyl, propyl, butyl, hexyl, etc.). More preferably, R$^4$ is aryl (e.g. $C_{6-12}$ aryl such as phenyl, naphthyl, etc.) which may be substituted by alkoxy (e.g. $C_{1-6}$ alkoxy such as methoxy, ethoxy, butoxy, hexyloxy, etc.) of alkylthio (e.g. $C_{1-6}$ alkylthio such as methylthio, ethylthio, butylthio, hexylthio, etc.). Said aryl is most preferably phenyl.

Preferably, W is a chemical bond, or a connecting group selected from the group consisting of a group of the formula: —SO$_f$— (in which f is an integer of 0–2), —CO—, a group of the formula: —CONR$^{11}$— [in which R$^{11}$ is lower alkyl (e.g. $C_{1-4}$ alkyl such as methyl, ethyl, propyl, butyl, etc.)]. More preferably, W is a chemical bond.

Preferably, R$^{1'}$ is a group of the formula: —(CH2)mQ" [in which m is an integer of 0–3, Q" is aryl which may be substituted by a group of the formula: —A—R$^5$ (wherein A and R$^5$ is the same meaning as defined above)]. The aryl is the same meaning as defined above, and preferably $C_{6-12}$ aryl (e.g. phenyl, naphthyl, etc.), more preferably, phenyl.

Preferably, R$^{4'}$ is optionally-substituted aryl. More preferably, R$^{4'}$ is aryl (e.g. $C_{6-12}$ aryl such as phenyl, naphthyl, etc.) which may be substituted by alkoxy (e.g. $C_{1-6}$ alkoxy such as methoxy, ethoxy, butoxy, hexyloxy, etc.) of alkylthio (e.g. $C_{1-6}$ alkylthio such as methylthio, ethylthio, butylthio, hexylthio, etc.). Said aryl is most preferably phenyl.

Preferred examples of the compound (I) and (I') or salts thereof are, for example, 2,4(1H,3H)-dioxo-5-methyl-6-(4-methoxymethoxyphenyl)-1-(2-methoxybenzyl)thieno[2,3-d]pyrimidine-3-acetic acid, 2,4(1H,3H)-dioxo-5-methyl-6-(4-methoxyphenyl)-1-(2-methylthiobenzyl)thieno[2,3-d]pyrimidine-3-acetic acid, 2,4(1H,3H)-dioxo-5-methyl-6-(4-methoxymethoxyphenyl)-1-(2-methylthiobenzyl)thieno[2,3-d]pyrimidine-3-acetic acid, 2,4(1H,3H)-dioxo-5-methyl-6-(4-methylthiomethoxyphenyl)-1-(2-methylthiobenzyl)thieno[2,3-d]pyrimidine-3-acetic acid, 2,4(1H,3H)-dioxo-5-methyl-6-(4-methylthiomethoxyphenyl)-1-(2-methoxybenzyl)thieno[2,3-d]pyrimidine-3-acetic acid, 2,4(1H,3H)-dioxo-5-methyl-1-(2-methylthiobenzyl)-6-(4-propoxyphenyl)thieno[2,3-d]pyrimidine-3-acetic acid and 2,4(1H,3H)-dioxo-5-methyl-1-(2-methylthiobenzyl)-6-[4-(2-oxopropoxy)phenyl]thieno[2,3-d]pyrimidine-3-acetic acid or salts thereof.

In the following, description is made on the method of producing the compound (I), (I') or a salt thereof.

(a) A compound (IV') according to compound (I) in which R$^1$ is hydrogen and R$^2$ is an optionally-substituted hydrocarbon residue, or its salt is produced by subjecting a compound of the formula (II'):

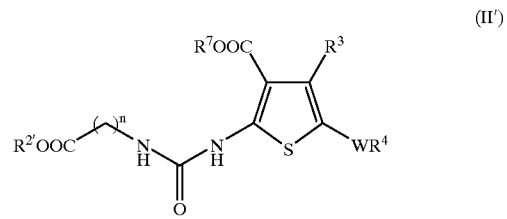

(II')

wherein R$^{2'}$, R$^3$, R$^4$, R$^7$, W and n are the same meanings as defined above, or its salt to a ring-closure reaction by using a base.

The ring-closure reaction is carried out in a solvent which does not affect the reaction. Examples of the solvent are, for example, alcohol (e.g. methanol, ethanol, isopropanol, etc.), ether (e.g. dioxane, tetrahydrofuran, etc.) and the like.

Examples of the base are, for example, alkali metal alkoxide (e.g. sodium methylate, sodium ethylate, sodium isopropoxide, etc.) and the like. One molar portion of the compound (II') is employed with about 1 to 5 moles, preferably about 1.5 to 3 moles of the base.

The reaction temperature is about 10° C. to boiling point of the employed solvent, preferably about 25° C. to boiling point of the employed solvent.

The reaction time is a few minutes to a few days, preferably about 10 minutes to 2 days.

(b) A compound (IV') or its salt is produced by subjecting the compound (III) or its salt to a ring-closure reaction by using a base and then subjecting the resulting ring-closure product to an electrophilic substitution reaction to introduce a group —WR$^4$ (in which W and R$^4$ are the same meaning as defined above).

The ring-closure reaction is carried out in a solvent which does not affect the reaction. Examples of the solvent are, for example, alcohol (e.g. methanol, ethanol, isopropanol, etc.), ether (e.g. dioxane, tetrahydrofuran, etc.) and the like.

Examples of the base are, for example, alkali metal alkoxide (e.g. sodium methylate, sodium ethylate, sodium isopropoxide, etc.) and the like. One molar portion of the compound (II') is employed with about 1 to 5 moles, preferably about 1.5 to 3 moles of the base.

The reaction temperature is about 10° C. to boiling point of the employed solvent, preferably about 25° C. to boiling point of the employed solvent.

The reaction time is a few minutes to a few days, preferably about 10 minutes to 2 days.

Examples of the electrophilic substitution reaction are per se known electrophilic substitution reaction. Preferred examples of the electrophilic substitution reaction are nitration (using, for example, fuming nitric acid-concentrated sulfuric acid, sodium nitrate-concentrated sulfuric acid, etc.), acylation (using, for example, an acid chloride-aluminum chloride, etc.), formylation (using, for example, phosphorus oxychloride-dimethylformamide, N-methylformanilide, etc.), halogenation (using, for example, N-bromosuccinimide, bromine-pyridine, sulfuryl chloride, etc.) and the like.

Said electrophilic substitution reaction can be carried out by a per se known method. For example, the nitration is carried out in fuming nitric acid-concentrated sulfuric acid or sodium nitrate-concentrated sulfuric acid at about 0 to 80° C. For example, acylation is carried out by using alkanoyl-chloride (e.g. acetyl chloride, propionyl chloride, etc.) in a solvent, which does not affect the acylation, such as nitrobenzen, nitromethane, carbondisufide and the like, in the presence of Lewis acid catalyst (e.g. aluminum chloride, titanium tetrachloride, etc.) at about 0 to 100° C. For example, the formulation is carried out by using phosphorous oxychloride-N,N-dimethylformamide or N-methylformanilide, oxalyl chloride-N,N-dimethylformamide or N-methylformanilide, thionyl chloride-N,N-dimethylformamide or N-methylformanilide in a solvent, which does not affect the formylation, such as benzene, toluene, xylene, tetrahydrofuran, dioxane, 1,2-dichloroethane and the like, at about 15 to 130° C. For example, the halogenation is carried out by using sulfuryl chloride, N-chlorosuccinimide, N-bromosuccinimide, bromine, chlorine, iodine, etc. in a solvent, which does not affect the halogenation, such as dichloromethane, chloroform, carbon tetrachloride, 1,2-dichloroethane, pyridine, benzene, toluene, xylene and the like, at about 15 to 130° C.

If desired, the group which is introduced by the electrophlic substitution reaction can be subjected a functional group conversion reaction. Examples of the functional group conversion reaction are per se known functional group conversion reactions such as reduction, acylation, sulfonylation, alkylation, diazo-coupling, Wittig reaction, halogenation, Grignard reagent with halide, organic zinc reagent, organic boron reagent organic thin reagent and the like.

(c) A compound (VI), according to the compound (I) in which $R^2$ is an optionally-substituted hydrocarbon residue, or its salt is produced by subjecting the compound (IV') or its salt, which is produced in above-mentioned (a) and (b), to react with a compound of the formula (V'):

$$R^{1'''}-X$$

wherein $R^{1'''}$ is an optionally-substituted hydrocarbon residue and X is halogen, or its salt.

The optionally-substituted hydrocarbon residue shown by $R^{1'''}$ is the same meaning as defined above. Halogen shown by X is fluorine, chlorine, bromine or iodine.

The reaction is carried out in a solvent which does not affect the reaction. Examples of the solvent are ether (e.g. dioxane, tetrahydrofuran, etc.), aromatic hydrocarbon (e.g. benzene, toluene, xylene, etc), amide (e.g. N,N-dimethylformamide, N,N-dimethylacetamide, etc), dimethylsulfoxide and the like. Preferably, the reaction is carried out in the presence of a base (e.g. potassium carbonate, sodium hydride, potassium hydride, potassium t-butoxide, etc.).

One molar portion of the compound (IV') is employed with about 1 to 5 moles, preferably about 1.1 to 2.5 moles of the compound (V'). When a base is used in the reaction, one molar portion of the compound (IV') is employed with about 1 to 5 moles, preferably about 1.1 to 3 moles of the base.

The reaction temperature is about 10° C. to boiling point of the employed solvent, preferably about 20° C. to 130° C.

The reaction time is a few minutes to a few days, preferably about 10 minutes to 2 days.

(d) A compound (VII), according to the compound (I) in which $R^2$ is hydrogen, or its salt is produced by subjecting the compound (VI) or its salt, which is produced in above-mentioned (c), to a reaction in which $R^{2'}$ is converted to hydrogen.

Example of the reaction, in which $R^{2'}$ is converted to hydrogen, is hydrolysis.

The hydrolysis is carried out by subjecting the compound (VI) or its salt to react a base in a solvent which does not affect the hydrolysis. Examples of the solvent are alcohol (e.g. methanol, ethanol, isopropanol, etc.), ether (e.g. dioxane, tetrahydrofuran, etc.), aromatic hydrocarbon (e.g. benzene, toluene, xylene, etc), amide (e.g. N,N-dimethylformamide, N,N-dimethylacetamide, etc), dimethylsulfoxide and the like. Examples of the base are alkali metal hydroxide (e.g. lithium hydroxide, sodium hydroxide, potassium hydroxide, etc.), alkaline earth metal hydroxide (e.g. calcium hydroxide, barium hydroxide, etc.), alkali metal carbonate (e.g. potassium carbonate, sodium carbonate, etc.).

One molar portion of the compound (VI) is employed with about 1 to 10 moles, preferably about 1.5 to 5 moles of the base.

The reaction temperature is about 10° C. to boiling point of the employed solvent, preferably about 15° C. to 130° C.

The reaction time is a few minutes to a few days, preferably about 10 minutes to 2 days.

Production of a raw compound (II), (III) or a salt thereof, used in the above-mentioned producing method (a) to (d), can be, for example, carried out by a method A or B as set forth below.

1. Method A.

The compound (II), (III) or a salt thereof is produced by subjecting a compound of the formula (VIII):

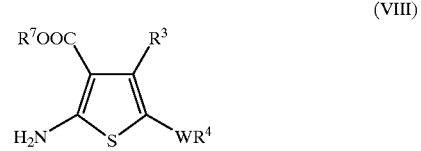

(VIII)

wherein $R^3$, $R^4$, $R^7$, W and n are the same meaning as defined above, or its slat; or a compound of the formula (VIII'):

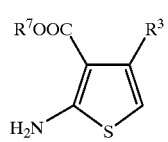
(VIII')

wherein R³ and R⁷ are the same meaning as defined above, or its salt to react with an isocyanate derivative.

Examples of the isocyanate derivative are an isocyanate ester derivative of the formula: $R^7OOC-(CH_2)n-NCO$ (in which $R^7$ and n are the same meaning as defined above.

The reaction is carried out in a solvent which does not affect the reaction. Examples of the solvent are tetrahydrofuran, pyridine, dioxane, benzene, dichloromethane, 1,2-dichloroethane, toluene, xylene, etc.).

One molar portion of the compound (VIII) or (VIII') is employed with about 1 to 5 moles, preferably about 1.1 to 2.5 moles of the icocyanate derivative.

The reaction temperature is about 15° C. to 130° C., preferably about 25° C. to 130° C. The reaction time is a few minutes to a few days, preferably about 10 minutes to 2 days.

2. Method B.

The compound (II), (III) or a salt thereof is produced by subjecting the compound (VIII), (VIII') or a salt thereof to react with phosgene or an equivalent thereof (e.g. diphosgene such as bis(trichloromethyl)carbonate, triphosgene such as trichloromethylchloroformate and the like) to give an isocyanate derivative, and then subjecting the isocyanate derivative to react with amine (e.g. a compound of the formula: $R^7OOC-(CH_2)n-NH_2$ (in which $R^7$ and n are the same meaning as defined above).

The reaction of the compound (VIII), (VIII') or its salt with the phosgene or its equivalent is carried out in a solvent which does not affect the reaction. Examples of the solvent are tetrahydrofuran, pyridine, dioxane, benzene, dichloromethane, 1,2-dichloroethane, toluene, xylene, etc.).

One molar portion of the compound (VIII) or (VIII') is employed with about 0.5 to 2 moles, preferably about 0.9 to 1.1 moles of the phosgene or its equivalent.

The reaction temperature is about 15° C. to 130° C., preferably about 25° C. to 130° C.

The reaction time is a few minutes to a few days, preferably about 10 minutes to 2 days.

The reaction of the isocyanate derivative with the amine is carried out in a solvent which does not affect the reaction. Examples of the solvent are tetrahydrofuran, pyridine, dioxane, benzene, dichloromethane, 1,2-dichloroethane, toluene, xylene, etc.).

One molar portion of the compound (VIII) or (VIII') is employed with about 1 to 5 moles, preferably about 1.1 to 3 moles of the phosgene or its equivalent.

The reaction temperature is about 15° C. to 130° C., preferably about 25° C. to 130° C.

The reaction time is a few minutes to a few days, preferably about 10 minutes to 2 days.

The compound (VIII) or its salt used in the above reaction is produced by the reaction of a ketone or an aldehyde having an activated methylene group [e.g. a compound of the formula (IX): $R^3-CO-CH_2-WR^4$ (in which $R^3$, $R^4$ and W are the same meanings as defined above)] with a cyanoacetate derivative and sulfur according to a method by Karl Gewald, et al. [K. Gewald, E. Schinke and H. Boettcher: Chem. Ber., 99, 94–100 (1966)]. Thus, in the case of a ketone [e.g. a compound (IX) in which $R^3$ is a group bonded through a nitrogen atom or a carbon atom], it is made to react with a cyanoacetate derivative in the presence of acetic acid and ammonium acetate are refluxed in a solvent, which does not affect the reaction, such as benzene, toluene and the resulting alkylidene cyanoacetate derivative is heated (e.g. about 50 to 80° C.) in the presence of sulfur and a base (e.g. an organic base such as triethylamine, ethyldiisopropyoamine, dimethylaminopyridine, etc.) in a solvent, which does not affect the reaction, such as methanol, ethanol to give a 2-aminothiophene derivative [the compound (VIII) in which $R^3$ is a group bonded through a nitrogen atom or a carbon atom]. In the case of an aldehyde [e.g. a compound (IX) in which $R^3$ is a hydrogen atom], it is heated with a cyanoester derivative in the presence of sulfur and a base (e.g. an organic base such as triethylamine, ethyldiisopropylamine, etc.) in a solvent, which does not affect the reaction, such as dimethylformamide, dimethylsulfoxide to give a 2-aminothiophene derivative [a compound (VIII) in which $R^3$ is a hydrogen atom].

The compound (VIII') can be synthesized by a method of Karl Gewald, et al. [K. Gewald: Chem. Ber. 98, 3571–3577 (1965); and K. Gewald and E. Schinke: Chem. Ber. 99, 2712–2715(1966)].

In the production method mentioned above, preferably, $R^1$ is a group shown by $R^{1'}$, $R^{1'''}$ is a group shown by $R^{1''}$ and $R^4$ is a group shown by $R^4$.

With respect to a salt of the compound of the present invention prepared as such, a physiologically acceptable acid addition salt is preferred. Examples of such a salt are the salts with inorganic acids (e.g. hydrochloric acid, hydrobromic acid, nitric acid, sulfuric acid, phosphoric acid, etc.) and the salts with organic acids (e.g. formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.). Further, when the compound (I) of the present invention has an acidic group such as —COOH, the compound (I) may form a salt with an inorganic base (e.g. an alkali metal or an alkali earth metal such as sodium, potassium, calcium and magnesium; and ammonia) or an organic base (e.g. trimethylamine, triethylamine, pyridine, picoline, ethanolamine, diethanolamine, triethanolamine, dicyclohexylamine, N,N'-dibenzylethylenediamine, etc.).

The compound or a salt thereof prepared as such can be isolated and purified by conventional separating means such as recrystallization, distillation, chromatography, etc. When the compound (I) is obtained in a free state, it can be converted to a salt by a known method per se or by a similar method thereto while, when it is obtained in a form of a salt, it can be converted to a free state or to another salt.

The salt of the above-mentioned compounds (II)–(IX) may be the same as that of the compound (I).

When the compound of the present invention or a salt thereof is an optically active substance, it can be separated into a d- and an l-compounds by a conventional means for optical resolution.

The compound of the present invention has an endothelin antagonistic activity with low toxicity thus rendering such compounds therapeuticall and diagnostically useful. Accordingly, it can be safely used as an endothelin antagonist to warm-blooded mammals (e.g. rats, mice, rabbits, cats, dogs, cattle, horses, human being, etc.) especially for treating or preventing acute renal insufficiency, myocardial infarction, liver insufficiency, angina pectoris, cerebral infarction, sub-arachnoid haemorrhage (SAH), hypertension, renal insufficiency, asthma, variant form of angina, Raynaud's syndrome, pulmonary hypertension, surgery shock, chronic cardiac insufficiency, cardiac hypertrophy, arteriosclerosis, migraine and the like, furthermore, for treating or preventing a hypofunction of an organ (e.g. liver, etc.) caused by its surgery or transplant, insufficient microcirculation, still fruthermore, for preventing restenosis after percutaneous transluminal coronary angioplasty (PTCA). More especially, it can be used for treating or preventing acute renal insufficiency, myocardial infraction, liver insufficiency, hypertension, pulmonary hypertension; for treating or preventing a hypofunction of an organ (e.g. liver, etc.) caused by its surgery or transplant, insufficient microcirculation; and for preventing restenosis after PTCA.

When the compound (I) or its salt is administered, for example, to human being, it can be safely administered either orally or parenterally as it is or as a pharmaceutical composition prepared by mixing with suitable pharmaceutically acceptable carriers, diluents, excipient, etc.

Examples of the above-mentioned pharmaceutical composition are oral agents (e.g. diluted powders, granules, capsules and tablets), injections, dropping injections, external agents (e.g. transnasal preparations, percutaneous preparations, etc.), ointments (e.g. rectal ointment, vaginal ointment, etc.) and the like.

Such pharmaceutical compositions can be manufactured by a per se known method commonly used in preparing pharmaceutical compositions.

The compound (I) of the present invention or a salt thereof can be made into injections either in a form of an aqueous injection together with dispersing agents [e.g. Tween 80 (Atlas Powder, U.S.A.), HCO 80 (Nikko Chemicals, Japan), polyethylene glycol, carboxymethylcellulose, sodium alginate, etc.], preservatives (e.g. methyl paraben, propyl paraben, benzyl alcohol, etc.), isotonizing agents (e.g. sodium chloride, mannitol, sorbitol, glucose, etc.) and the like or in a form of an oily injection by dissolving, suspending or emulsifying in plant oil (e.g. olive oil, sesame oil, cotton seed oil, corn oil, etc.), propylene glycol and the like.

In preparing a pharmaceutical composition for oral use, the compound (I) of the present invention or a salt thereof is molded by compressing, for example, with fillers (e.g. lactose, sucrose, starch, etc.), disintegrating agents (e.g. starch, calcium carbonate, etc.), binders (e.g. starch, gum arabic, carboxymethylcellulose, polyvinylpyrrolidone, hydroxypropylcellulose, etc.) or lubricants (e.g. talc, magnesium stearate, polyethylene glycol 6000, etc.) and the like. If necessary, the composition is coated by a per se known method with an object of masking the taste, enteric caoting or long-acting. Examples of the coating agent therefor are hydroxypropylmethylcellulose, ethylcellulose, hydroxymethylcellulose, hydroxypropylcellulose, polyoxyethylene glycol, Tween 80, pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), red oxide of iron and the like. Subcoating layer may be provided between the enteric coating and the core according to per se known method.

In preparing an external composition, the compound (I) of the present invention or a salt thereof as it is or a salt thereof is subjected to a per se known method to give a solid, semisolid or liquid agent for external use. For example, the solid preparation is manufactured as follows. Thus, the compound (I) as it is or after adding/mixing fillers (e.g. glycol, mannitol, starch, microcrystalline cellulose, etc.), thickeners (e.g. natural gums, cellulose derivatives, acrylic acid polymers, etc.) and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be compounded with a pH adjusting agent (e.g. carbonic acid, phosphoric acid, citric acid, hydrochloric acid, sodium hydroxide, etc.), an antiseptic agent (e.g. p-hydroxybenzoates, chlorobutanol, benzalkonium chloride, etc.) and the like.

In the manufacture of an ointment for example, the compound (I) of the present invention or a salt thereof can be made into an oily or an aqueous solid, semisolid or liquid ointment. Examples of the oily base material applicable in the above-mentioned composition are glycerides of higher fatty acids [e.g. cacao butter, Witepsols (manufactured by Dynamite-Nobel), etc.], medium fatty acids [e.g. Miglyols (manufactured by Dynamite-Nobel), etc.] and plant oil (e.g. sesame oil, soybean oil, cotton seed oil, etc.) and the like. Examples of the aqueous base material are polyethylene glycols and propylene glycol and those of the base material for aqueous gel are natural gums, cellulose derivatives, vinyl polymers, acrylic acid polymers, etc.

A daily dose may vary depending upon the degree of the disease; age, sex, body weight, a difference in the susceptibility, etc. of the patient; time and interval of the administration; nature, composition and type of the pharmaceutical composition; type of the active component; and the like and is not particularly limited. Usually, however, it is about 0.01–150 mg/kg, preferably about 0.1–100 mg/kg or, more preferably, about 0.5–50 mg/kg to warm-blooded animals. The above dose is usually administered by dividing it into one to four times a day.

EXAMPLES

The present invention will be further illustrated by way of the following examples though the present invention is not to be limited thereto.

$^1$H-NMR spectrum is determined by a Varian Gemini 200 (200 MHz) type spectrometer or Bruker AM-500 (500 MHz) type spectrometer using tetramethyl silane as the internal standard, expressing all the values as ppm.

Symbols used in the reference examples and working examples are of the following meaning.

s; singlet, d; doublet, t; triplet, q; quartet, dd; double doublet; dt; double triplet, m; multiplet, br; broad, J; coupling constant.

Reference Example 1

Production of ethyl 2-amino-5-phenylthiophene-3-carboxylate.

Phenylacetaldehyde (a 50% solution in diethyl phthalate; 12.05 g; 50 mmoles) was added dropwise, within 20 minutes, into a mixture of ethyl cyanoacetate (6.1 g, 50 mmoles), sulfur (1.61 g, 50 mmoles), triethylamine (3.5 ml, 25 mmoles) and dimethylformamide (10 ml). The mixture was stirred at 45° C. for nine hours. The reaction mixture was concentrated and the resulting residue was extracted with ethyl acetate. The extract was washed with an aqueous solution of sodium chloride, then dried over $MgSO_4$ and evaporated in vacuo. The resulting residue was chromatographed on silica gel followed by crystallizing from ether-hexane to give pale yellow plates (5.55 g; 45%).

m.p. 124.5–125.5° C. (the literature value: 123–124° C.

Elemental analysis (%) for $C_{13}H_{13}NO_2S$: Calcd.: C 63.13, H 5.30, N 5.66; Found : C 62.99, H 5.05, N 5.63.

$^1$H-NMR (200 MHz, CDCl$_3$) δ: 1.37 (3H, t, J=7.1 Hz), 4.30 (2H, d, J=7.1 Hz), 5.97 (2H, br), 7.17–7.46 (6H, m).

IR (KBr): 3448, 3320, 1667, 1590, 1549 cm$^{-1}$.

Reference Example 2

Production of ethyl 2-amino-4-methyl-5-(4-methoxyphenyl)thiophene-3-carboxylate.

A mixture of 4-methoxyphenylacetone (16.5 g, 0.10 mole), ethyl cyanoacetate (12.2 g, 0.10 mole), ammonium acetate (1.55 g, 20 mmoles), acetic acid (4.6 ml, 80 mmoles) and benzene (20 ml) was refluxed for 24 hours together with a removal of the resulting water therefrom by means of a Dene-Starke's apparatus. After cooling, the reaction mixture was concentrated in vacuo and the resulting residue was partitioned between dichloromethane and an aqueous solution of sodium bicarbonate. The organic layer was washed with an aqueous solution of sodium chloride, then dried over MgSO$_4$ and evaporated in vacuo. The resulting residue was taken up in ethanol (30 ml). To the solution were added sulfur (3.21 g, 0.10 mole) and diethylamine (10.4 ml, 0.10 mole), and the mixture was stirred at 50–60° C. for two hours. The reaction mixture was concentrated and the resulting residue was extracted with ethyl acetate. The extract was washed with an aqueous solution of sodium chloride, then dried over MgSO$_4$ and evaporated in vacuo. The resulting residue was chromatographed on silica gel followed by crystallizing from ether-hexane to give pale yellow plates (11.5 g; 40%).

m.p. 79–80° C.

Elemental analysis (%) for C$_{15}$H$_{17}$NO$_3$S: Calcd.: C 61.83, H 5.88, N 4.81, S 11.01; Found : C 61.81, H 5.75, N 4.74, S 10.82.

$^1$H-NMR (200 MHz, CDCl$_3$) δ: 1.37 (3H, t, J=7.1 Hz), 2.28 (3H, s), 3.83 (3H, s), 4.31 (2H, q, J=7.1 Hz), 6.05 (2H, brs), 6.91 (2H, d, J=8.8 Hz), 7.27 (2H, d, J=8.8 Hz).

IR (KBr): 3426, 3328, 1651, 1586, 1550, 1505, 1485 cm$^{-1}$.

FAB-MS m/z: 291 (M$^+$).

Reference Example 3

Production of ethyl 2-amino-4-methyl-5-phenylthiophene-3-carboxylate.

Phenylacetone (11.6 g; 86.5 mmoles) was used instead of 4-phenylacetone and the same operations as mentioned in Reference Example 2 were carried out using ethyl cyanoacetate (10.5 g, 86.5 mmoles), ammonium acetate (1.34 g, 17.4 mmoles), acetic acid (3.96 ml, 69.2 mmoles), sulfur (2.78 g, 86.5 mmoles) and dietylamine (8.95 ml, 86.5 mmoles) to give colorless needles (9.95 g; 40%).

m.p. 64–65° C. (recrystallized from ether-hexane; lit: 95° C.

Elemental analysis (%) for C$_{14}$H$_{15}$NO$_2$S: Calcd.: C 64.34, H 5.79, N 5.36; Found : C 64.51, H 5.77, N 5.29.

$^1$H-NMR (200 MHz, CDCl$_3$) δ: 1.37 (3H, t, J=7.1 Hz), 2.33 (3H, s), 4.32 (2H, q, J=7.1 Hz), 6.09 (2H, br), 7.24–7.42 (5H, m).

IR (KBr): 3388, 3278, 1665, 1584, 1549, 1481 cm$^{-1}$.

Reference Example 4

Production of ethyl 2-amino-4-methyl-5-(3,4-methylenedioxyphenyl)thiophene-3-carboxylate.

3,4-Methylenedioxyphenylacetone (5.34 g; 30 mmoles) was used instead of 4-phenylacetone and the same operations as in Reference Example 2 were carried out by using ethyl cyanoacetate (3.65 g, 30 mmoles), ammonium acetate (0.46 g, 6 mmoles), acetic acid (1.37 ml, 24 mmoles), sulfur (0.90 g, 28.25 mmoles) and diethylamine (2.92 ml, 28.25 mmoles) to give pale yellow powders (2.90 g; 34%).

hu 1H-NMR (200 MHz, CDCl$_3$) δ: 1.37 (3H, t, J=7.1 Hz), 2.29 (3H, s), 4.31 (2H, q, J=7.1 Hz), 5.99 (2H, s), 6.82 (3H, s).

Reference Example 5

Production of ethyl 2-amino-4-methyl-5-(3,4-dimethoxyphenyl)thiophene-3-carboxylate.

3,4-Dimethoxyphenylacetone (5.0 ml; 28.7 mmoles) was used instead of 4-phenylacetone and the same operations as in Reference Example 2 were carried out by using ethyl cyanoacetate (0.44 g, 5.74 mmoles), ammonium acetate (3.49 g, 28.7 mmoles), acetic acid (1.32 ml, 23.0 mmoles), sulfur (0.90 g, 28.0 mmoles) and diethylamine (2.9 ml, 28.0 mmoles) to give pale yellow powders (3.09 g; 34%).

$^1$H-NMR (200 MHz, CDCl$_3$) δ: 1.38 (3H, t, J=7.1 Hz), 2.30 (3H, s), 3.89 (3H, s), 3.91 (3H, s), 4.32 (2H, q, J=7.1 Hz), 6.07 (2H, s), 6.74–6.89 (3H, m).

Reference Example 6

Production of ethyl 2,4(1H,3H)-dioxo-5-methylthieno[2,3-d]pyrimidine-3-acetate.

Ethyl isocyanate acetate (9.1 ml; 81.1 mmoles) was added dropwise into a solution of ethyl 2-amino-4-methylthiophene (10.0 g, 54.0 mmoles) in pyridine (25 ml) at 45–50° C. The mixture was stirred for two hours. The reaction mixture was evaporated to dryness and the resulting residue was partitioned between ethyl acetate and diluted hydrochloric acid. The aqueous layer was extracted with ethyl acetate. The combined extracts were washed with an aqueous solution of sodium chloride, dried over MgSO$_4$ and evaporated in vacuo. The resulting residue was recrystallized from ethyl acetate to give colorless needles (16.1 g). The crystals (12.0 g; 38.2 mmoles) were suspended in ethanol (150 ml), then sodium ethoxide [prepared from metal sodium (1.95 g, 84.8 mmoles) and ethanol (70 ml)] was added thereto and the mixture was stirred at room temperature for one hour. To the reaction mixture was added 2N hydrochloric acid (45 ml) under ice-cooling and ethanol was evaporated therefrom in vacuo. The crystals separated out therefrom were collected by filteration, washed with water-ethanol, dried over phosphorus pentaoxide in vacuo and recrystallized from ethanol to give colorless needles (9.50 g; 93%).

m.p. 229–230° C.

Reference Example 7

Production of ethyl 2,4(1H,3H)-dioxo-4-nitro-5-methylthieno[2,3-d]pyrimidine-3-acetate.

To the compound produced in Reference Example 6 (4.0 g, 14.9 mmoles) was added concentrated sulfuric acid (15 ml) and then a solution of sodium nitrate (1.33 g, 15.7 mmoles) in concentrated sulfuric acid (25 ml) was added dropwise thereinto with ice-cooling over 15 minutes. After the addition was complete, the mixture was stirred under ice-cooling for one hour. The reaction mixture was poured into ice-water and extracted with a mixture of ethyl acetate and tetrahydrofuran. The extract was washed with an aqueous solution of sodium chloride, dried over MgSO$_4$ and evaporated in vacuo. The resulting residue was chromatographed on silica gel to give a white solid (4.08 g; 86%). The solid was recrystallized from ethyl acetate-hexane to give yellow needles.

m.p. 214–215° C.

Elemental analysis (%) for $CH_{11}H_{11}N_3O_6S.0.1H_2O$: Calcd.: C 41.93, H 3.58, N 13.34; Found : C 41.90, H 3.88, N 13.24.

$^1$H-NMR (200 MHz, DMSO-$d_6$) δ: 1.35 (3H, t, J=7.1 Hz), 2.95 (3H, s), 4.30 (2H, q, J=7.1 Hz), 4.75 (2H, s), 10.66 (1H, brs).

IR (KBr): 3530, 1760, 1719, 1676, 1549, 1444, 1321 cm$^{-1}$.

Reference Example 8

Production of ethyl 2,4(1H,3H)-dioxo-1-(2-methoxybenzyl)-5-methyl-6-nitrothieno[2,3-d]pyrimidine-3-acetate.

A solution of the compound produced in Reference Example 7 (0.912 g, 5.87 mmoles) in dimethylformamide (6 ml) was added dropwise into a suspension of sodium hydride (0.125. g, 3.13 mmoles, which was washed with n-Hexane) in dimethylformamide (2 ml) under nitrogen stream with ice-cooling. The mixture was stirred with ice-cooling for 20 minutes and a solution of 2-methoxybenzyl chloride (0.92 g, 5.87 mmoles) in dimethylformamide (1 ml) was added dropwise thereinto. The mixture was stirred at room temperature for 12 hours, then at 60° C. for 24 hours. After cooling, the reaction mixture was concentrated and the resulting residue was partitioned between ethyl acetate and an aqueous solution of ammonium chloride. The aqueous layer was extracted with ethyl acetate. The combined extracts were washed with an aqueous solution of sodium chloride, dried over MgSO$_4$ and evaporated in vacuo. The resulting residue was chromatographed on silica gel to give a pale yellow solid (0.70 g; 56%), which was recrystallized from ethyl acetate-hexane to give colorless powders.

m.p. 175–177° C.

Elemental analysis (%) for $C_{19}H_{19}N_3O_7S$: Calcd.: C 52.65 H 4.42, N 9.69; Found : C 52.87, H 4.33, N 9.50.

$^1$H-NMR (200 MHz, CDCl$_3$) δ: 1.31 (3H, t, J=7.2 Hz), 2.97 (3H, s), 3.90 (3H, s), 4.26 (2H, q, J=7.1 Hz), 4.79 (2H, s), 5.24 (2H, s), 6.90–6.97 (2H, m), 7.17–7.37 (2H, m).

IR (KBr): 2970, 1740, 1721, 1678, 1547, 1489 cm$^{-1}$.

Reference Example 9

Production of ethyl 2,4(1H,3H)-dioxo-1-(2-methylthiobenzyl)-5-methyl-6-nitrothieno[2,3-d]pyrimidine-3-acetate.

The same operations as in Reference Example 8 were carried out by using 2-methylthiobenzyl chloride instead of 2-methoxybenzyl chloride to give pale yellow powders (1.33 g; 62%).

$^1$H-NMR (200 MHz, CDCl$_3$) δ: 1.31 (3H, t, J=7.1 Hz), 2.57 (3H, s), 2.98 (3H, s), 4.27 (2H, q, J=7.1 Hz), 4.82 (2H, s), 5.36 (2H, s), 6.99–7.36 (4H, m).

Reference Example 10

Production of ethyl 2,4(1H,3H)-dioxo-1-(2-methylthiobenzyl)-5-methyl-6-acetamidothieno[2,3-d]pyrimidine-3-acetate.

The compound produced in Reference Example 9 (1.10 g; 2.45 mmoles) was dissolved in acetic acid (50 ml). To this solution was added iron powder (0.72 g, 12.3 mmoles) and the resulting mixture was stirred at 80° C. for four hours. The reaction mixture was concentrated and the resulting residue was partitioned between ethyl acetate and a saturated aqueous solution of sodium bicarbonate. The aqueous layer was extracted with ethyl acetate. The combined extracts were washed with an aqueous solution of sodium chloride, dried over MgSO$_4$ and evaporated in vacuo. The resulting residue was chromatographed on silica gel to give a pale yellow solid (1.2 g), which was recrystallized from ethyl acetate-hexane to give yellow plates (0.79 g; 70%).

$^1$H-NMR (200 MHz, CDCl$_3$) δ: 1.31 (3H, t, J=7.1 Hz), 2.16 (3H, s), 2.37 (3H, s), 4.26 (2H, s), 4.82 (2H, q, J=7.1 Hz), 5.30 (2H, s), 6.96–7.36 (4H, m), 7.87 (1H, s).

Reference Example 11

Production of ethyl 2,4(1H,3H)-dioxo-1-(2-methoxybenzyl)-5-methyl-6-acetamidothieno[2,3-d]pyrimidine-3-acetate.

The compound prepared in Reference Example 8 was treated by the same manner as in Reference Example 10 to give colorless powders (0.09 g; 29%).

m.p. 233–234° C.

Elemental analysis (%) for $C_{21}H_{23}N_3O_6S.0.1H_2O$: Calcd.: C 56.39, H 5.23, N 9.39; Found : C 56.30, H 5.18, N 9.34.

$^1$H-NMR (200 MHz, CDCl$_3$) δ: 1.32 (3H, t, J=7.1 Hz), 2.16 (3H, s), 2.34 (3H, s), 3.91 (3H, s), 4.27 (2H, q, J=7.1 Hz), 4.80 (2H, s), 5.18 (2H, s), 6.81–6.90 (2H, m), 7.04–7.08 (1H, m), 7.20–7.28 (1H, m), 8.11 (1H, s).

IR (KBr): 3296, 1760, 1700, 1644, 1586, 1553, 1493 cm$^{-1}$.

Reference Example 12

Production of ethyl 2,4(1H,3H)-dioxo--6-bromo-5-methylthieno[2,3-d]pyrimidine-3-acetate.

A mixture of the compound produced in Reference Example 6 (3.50 g, 13.05 mmoles), N-bromosuccinimide (2.55 g, 14.35 mmoles) and chloroform (360 ml) was refluxed for 3 hours. After cooling, the reaction mixture was partitioned between chlorform and an aqueous solution of sodium chloride. The aqueous layer was extracted with chloroform. The combined extracts were dried over MgSO$_4$ and evaporated in vacuo. The resulting residue was recrystallized from ethyl acetate-hexane to give colorless crystals (3.15 g, 67%).

m.p. 189–190° C.

$^1$H-NMR (200 MHz, CDCl$_3$) δ: 1.34 (3H, t, J=7.2 Hz), 2.40 (3H, s), 4.28 (2H, q, J=7.2 Hz), 4.76 (2H, s), 10.20 (1H, s).

IR (KBr): 1748, 1717, 1657, 1572, 1437 cm$^{-1}$.

Reference Example 13

Production of ethyl 2,4(1H,3H)-dioxo-6-bromo-5-methyl-1-(2-methylthiobenzyl)thieno[2,3-d]pyrimidine-3-acetate.

To a solution of the compound produced in Reference Example 12 (2.00 g, 5.76 mmoles) in dimethylformamide (30 ml) was added potassium carbonate (1.19 g, 8.64 mmoles), potassium iodide (0.19 g, 1.15 mmoles) and 2-methylthiobenzyl chloride (1.99 g, 11.52 mmoles) and the mixture was stirred at room temperature for 16 hours. The reaction mixture was concentrated and the resulting residue was partitioned between ethyl acetate and an aqueous solution of sodium chloride. The aqueous layer was extracted with ethyl acetate. The combined extracts were dried over MgSO$_4$ and evaporated in vacuo. The resulting residue was chromatographed on silica gel to give white powders (2.12 g, 76%).

m.p. 150–151° C.

$^1$H-NMR (200 MHz, CDCl$_3$) δ: 1.30 (3H, t, J=7.1 Hz), 2.44 (3H, s), 2.55 (3H, s), 4.24 (2H, q, J=7.1 Hz), 4.82 (2H, s), 5.29 (2H, s), 6.97–7.34 (4H, m).

IR (KBr): 1746, 1707, 1669, 1475 cm$^{-1}$.

Example 1

Production of ethyl 2,4(1H,3H)-dioxo-6-phenylthieno[2,3-d]pyrimidine-3-acetate (Compound 1).

Ethyl isocyanoacetate (1.4 ml; 12.5 mmoles) was added dropwise into a solution of the compound produced in Reference Example 1 (2.0 g, 8.09 mmoles) in pyridine (8 ml) and the mixture was stirred at 45° C. for 2 hours. The reaction mixture was concentrated in vacuo, the resulting residue was suspended in a mixture of ethanol (20 ml) and sodium ethoxide [prepared from metal sodium (0.38 g, 16.5 mmoles) and ethanol (15 ml)]. The mixture was stirred at room temperature for 3 hours. To the reaction mixture was added 2N hydrochloric acid (10 ml) with ice-cooling and ethanol was evaporated therefrom in vacuo. The resulting solids were washed with water-ethanol and dried over phosphorus pentaoxide to give colorless powders (2.57 g; 96%), which was recrystallized from ethanol to afford colorless crystals.

m.p. 279–280.5° C.

Elemental analysis (%) for C$_{16}$H$_{14}$N$_2$O$_4$S.0.2H$_2$O: Calcd.: C 57.54, H 4.35, N 8.39; Found : C 57.56, H 4.32, N 8.36.

$^1$H-NMR (200 MHz CDCl$_3$-DMSO-d$_6$) δ: 1.29 (3H, t, J=7.2 Hz), 4.23 (2H, q, J=7.2 Hz), 4.75 (2H, s), 7.26–7.55 (6H, m), 12.08 (1H, s).

IR (KBr): 3140, 2986, 1745, 1725, 1659, 1566, 1547, 1483 cm$^{-1}$.

Example 2

The compounds listed in Table 1 were produced starting from the compounds obtained in Reference Examples 1, 2 and 3 by the same method as mentioned in Example 1.

TABLE 1

| Cpd. No. | R$^3$ | R$^{12}$ | R$^2$ | n | Yield (%) | M.p. (° C.) |
|---|---|---|---|---|---|---|
| 2 | Hydrogen | Hydrogen | Ethyl | 2 | 65 | 231–233 |
| 3 | Hydrogen | Hydrogen | Methyl | 3 | 43 | 214–215 |
| 4 | Methyl | Hydrogen | Ethyl | 1 | 41 | 119–120 |
| 5 | Methyl | 4-Methoxy | Ethyl | 1 | 96 | 164–165 |
| 6 | Methyl | 4-Methoxy | Ethyl | 2 | 84 | 185–186 |
| 7 | Methyl | 4-Methoxy | Methyl | 3 | 81 | 179–180 |
| 8 | Methyl | 3,4-Methylenedioxy | Ethyl | 1 | 88 | 204–205 |
| 9 | Methyl | 3,4-Dimethoxy | Ethyl | 1 | 90 | 220–221 |

Compound 5 in Table 1 was also produced by the following method.

A solution of a compound prepared in Reference Example 2 (0.58 g, 2.00 mmoles) and triphosgene (0.42 g, 1.40 mmoles) in dioxan (10 ml) was stirred at 100° C. for 3 hours. The reaction mixture was concentrated to dryness. To the residue were added ethylglycine (0.51 g, 5.00 mmoles) and pyridine (10 ml) and the mixture was stirred at room temperature for 30 minutes. The reaction mixture was concentrated and the resulting residue was partitioned between dichloromethane and an diluted hydrochloric acid. The aqueous layer was extracted with dichloromethane. The combined extracts were dried over MgSO$_4$ and evaporated in vacuo. The resulting residue was suspended in a mixture of ethanol (5 ml) and sodium ethoxide [prepared from metal sodium (0.07 g, 3.00 mmoles) and ethanol (3 ml)]. The mixture was stirred at room temperature for 3 hours. To the reaction mixture was added 2N hydrochloric acid (4 ml) with ice-cooling and ethanol was evaporated therefrom in vacuo. The resulting crystals were washed with aqueous ethanol and dried over phosphorus pentaoxide to give colorless powders (0.53 g; 71%).

Example 3

Production of ethyl 2,4(1H,3H)-dioxo-5-methyl-6-(4-nitrophenyl)thieno[2,3-d]pyrimidine-3-acetate (Compound 10).

A solution of sodium nitrate (0.125 g, 1.45 mmoles) in concentrated sulfuric acid (3.5 ml) was added dropwise into a solution of the compound 4 produced in Example 2 (0.50 g, 1.45 mmloes) in concentrated sulfuric acid (3 ml) with ice-cooling. The mixture was stirred with ice-cooling for one hour. The reaction mixture was poured into ice-water and the mixture was extracted with ethyl acetate. The extract was washed with an aqueous solution of sodium chloride, dried over MgSO$_4$ and evaporated in vacuo. The resulting residue was recrystallized from ethyl acetate to give yellow crystals (0.285 g; 50%).

m.p. 276–278° C.

Elemental analysis (%) for C$_{17}$H$_{15}$N$_3$O$_6$S: Calcd.: C 52.44, H 3.88, N 10.79; Found: C 52.63, H 3.76, N 10.61.

$^1$H-NMR (200 MHz, DMSO-d$_6$) δ: 1.22 (3H, t, J=7.1 Hz), 2.52 (3H, s), 4.16 (2H, q, J=7.1 Hz), 4.61 (2H, s), 7.77 (2H, d, J=8.9 Hz), 8.31 (2H, d, J=8.9 Hz), 12.61 (1H, brs).

IR (KBr): 2928, 1748, 1721, 1659, 1597, 1568, 1520, 1460, 1348 cm$^{-1}$.

Example 4

Production of ethyl 2,4(1H,3H)-dioxo-6-(4-hydroxyphenyl)-5-methylthieno[2,3-d]pyrimidine-3-acetate (Compound 11).

A solution of the compound produced in Example 2 (2.0 g, 5.34 mmoles) in dichloromethane (40 ml) was added dropwise into a mixture of anhydrous aluminum chloride (2.90 g, 21.7 mmoles), methyl sulfide (2.45 ml, 27.2 mmoles) and dichloromethane (60 ml) with ice-cooling. The mixture was stirred at room temperature for 20 hours. The reaction mixture was poured into ice-water and the mixture was evaporated in vacuo. The resulting suspension was extracted with ethyl acetate. The extract was washed with an aqueous solution of sodium chloride, dried over MgSO$_4$ and evaporated in vacuo. The resulting residue was chromatographed on silica gel to give colorless powders (1.64 g; 85%). The resulting powders were recrystallized from ethyl acetate to give colorless crystals.

m.p. 240–242° C.

Elemental analysis (%) for C$_{17}$H$_{16}$N$_2$O$_5$S.0.1H$_2$O: Calcd.: C 56.38, H 4.51, N 7.73; Found: C 56.28, H 4.48, N 7.64.

$^1$H-NMR (200 MHz, DMSO-d$_6$) δ: 1.22 (3H, t, J=7.1 Hz), 2.37 (3H, s), 4.15 (2H, q, J=7..1 Hz), 4.59 (2H, s), 6.85 (2H, d, J=8.6 Hz), 7.26 (2H, d, J=8.6 Hz), 9.73 (1H, s), 12.39 (1H, s).

IR (KBr): 3356, 2992, 1720, 1690, 1667, 1611, 1593, 1568, 1537, 1502 cm$^{-1}$.

Example 5

Production of ethyl 2,4(1H,3H)-dioxo-1-(2-methoxybenzyl)-6-phenylthieno[2,3-d]pyrimidine-3-acetate (Compound 12).

A solution of the compound 1 produced in Example 1 (0.50 g, 1.51 mmoles) in dimethylformamide (6 ml) was added dropwise into a suspension of sodium hydride (61 mg, 1.53 mmoles) in dimethylformamide (3 ml) with ice-cooling under nitrogen atmosphere. The mixture was stirred with ice-cooling for 20 minutes and a solution of 2-methoxybenzyl chloride (0.72 g, 4.60 mmoles) in dimethylformamide (3 ml) was added dropwise to the mixture. The mixture was stirred at room temperature for 22 hours and then concentrated. The resulting residue was partitioned between ethyl acetate-tetrahydrofuran and an aqueous solution of ammonium chloride. The aqueous layer was extracted with ethyl acetate. The combined extracts were washed with an aqueous solution of sodium chloride, dried over MgSO$_4$ and evaporated in vacuo. The resulting residue was chromatographed on silica gel to give pale yellow powders (0.463 g; 68%). The resulting powders were recrystallized from ethyl acetate to give colorless crystals.

m.p 182–183.5° C.

Elemental analysis (%) for C$_{24}$H$_{22}$N$_2$O$_5$S: Calcd.: C 63.99, H 4.92, N 6.22; Found: C 63.82, H 4.96, N 6.25.

$^1$H-NMR (200 MHz, CDCl$_3$) δ: 1.30 (3H, t, J=7.1 Hz), 3.90 (3H, s), 4.25 (2H, q, J=7.2 Hz), 4.83 (2H, s), 5.27 (2H, s), 6.88–6.95 (2H, m), 7.14–7.18 (1H, m), 7.25–7.51 (6H, m), 7.53 (1H, s).

IR (KBr): 2996, 1750, 1709, 1667, 1557, 1526, 1499, 1473 cm$^{-1}$.

Example 6

Production of ethyl 2,4(1H,3H)-dioxo-1-(2,4-dimethoxybenzyl)-6-(4-methoxyphenyl)-5-methylthieno[2,3-d]pyrimidine-3-acetate (Compound 13).

To a solution of the compound 5 produced in Example 2 (0.73 g, 1.95 mmoles) in anhydrous tetrahydrofuran (THF, 25 ml) were added dropwise 2,4-dimethoxybenzyl alcohol (0.49 g, 2.91 mmoles) and tri-n-butylphosphine (0.91 ml, 3.65 mmoles) and the mixture was stirred. To this solution was added azidocarbonyl dipiperidine (0.92 g, 3.55 mmoles) under nitrogen stream. The mixture was stirred under a nitrogen stream at room temperature for six hours and then at 60° C. for 18 hours. After cooling, the reaction mixture was partitioned between ethyl acetate and an aqueous solution of sodium chloride. The aqueous layer was extracted with ethyl acetate. The combined extracts were washed with an aqueous solution of sodium chloride again, dried over MgSO$_4$ and evaporated in vacuo. The resulting residue was chromatographed on silica gel to give colorless powders (0.37 g; 27%). The resulting powders were recrystallized from ethyl ether-n-hexane to give colorless crystals.

m.p. 110–111° C.

Elemental analysis (%) for C$_{27}$H$_{28}$N$_2$O$_7$S: Calcd.: C 61.82, H 5.38, N 5.34; Found: C 61.80, H 5.42, N 5.25.

$^1$H-NMR (200 MHz, CDCl$_3$) δ: 1.30 (3H, t, J 7.2 Hz), 2.48 (3H, s), 3.77 (3H, s), 3.83 (6H s), 4.25 (2H, q, J=7.2 Hz), 4.82 (2H, s), 5.16 (2H, s), 6.40–6.45 (2H, m), 6.93 (2H, d, J=8.9 H), 7.07–7.11 (1H, m), 7.28 (2H, d, J=8.9 HZ).

IR (KBr): 2974, 1754, 1711, 1663, 1613, 1589, 1528, 1510, 1477 cm$^{-1}$.

Example 7

The compounds listed in Tables 2, 3, 4 and 5 were produced by the same method as mentioned in Example 5 starting from the compounds produced in Examples 1, 2, 3, 17, 18, 19, 27 and 29.

TABLE 2

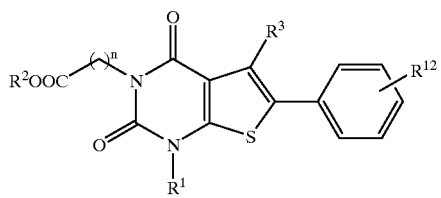

| Cpd. No. | R$^3$ | R$^{12}$ | R$^1$ | R$^2$ | n | Yield (%) | M.p. (° C.) |
|---|---|---|---|---|---|---|---|
| 14 | H | H | 2-(1-Methylindol-3-yl)ethyl | Et | 1 | 15 | 226–227.5 |
| 15 | H | H | 2-Quinolylmethyl | Et | 1 | 56 | 199.5–201.5 |
| 16 | H | H | 3,4-Methylenedioxybenzyl | Et | 1 | 84 | 182–184 |
| 17 | H | H | 2-Methoxybenzyl | Et | 2 | 78 | 142–143 |
| 18 | H | H | 2-Methoxybenzyl | Me | 3 | 69 | 126–127 |
| 19 | H | H | Cyclohexylmethyl | Et | 1 | 75 | 169–170 |
| 20 | H | H | 3-Methoxybenzyl | Et | 1 | 64 | 164–165 |
| 21 | H | H | 4-Methoxybenzyl | Et | 1 | 91 | 143–145 |
| 22 | H | H | 2-Methoxyphenethyl | Et | 1 | 63 | 143–144 |
| 23 | Me | H | 2-Methoxybenzyl | Et | 1 | 89 | 151–152 |
| 24 | Me | H | 2-(1-Methylindol-3-yl)ethyl | Et | 1 | 91 | 179–181 |
| 25 | Me | 4-MeO | 2-Methoxybenzyl | Et | 1 | 78 | 141–142 |

(Me: methyl; Et: ethyl; MeO: methoxy)

TABLE 3

| Cpd. No. | R$^3$ | R$^{12}$ | R$^1$ | R$^2$ | n | Yield (%) | M.p. (° C.) |
|---|---|---|---|---|---|---|---|
| 26 | Me | 4-MeO | 2-(1-Methylindol-3-yl)ethyl | Et | 1 | 85 | 163–164 |
| 27 | Me | 4-NO$_2$ | 2-Methoxybenzyl | Et | 1 | 87 | 178–179 |
| 28 | Me | 4-MeO | Butyl | Et | 1 | 81 | 134.5–136 |
| 29 | Me | 4-MeO | Benzyl | Et | 1 | 81 | 126–128 |
| 30 | Me | 4-MeO | 2-Methylbenzyl | Et | 1 | 78 | 127–128.5 |
| 31 | Me | 4-MeO | 2-Bromobenzyl | Et | 1 | 94 | 144–144.5 |
| 32 | Me | 4-MeO | 2-Nitrobenzyl | Et | 1 | 62 | 154–156 |
| 33 | Me | 4-MeO | 2-Cyanobenzyl | Et | 1 | 80 | 176–177 |
| 34 | Me | 4-MeO | 2-Methylthiobenzyl | Et | 1 | 88 | 144–145 |
| 35 | Me | 4-MeO | 2-Methoxyphenethyl | Et | 1 | 81 | 113–115 |
| 36 | Me | 4-Nitro | 2-Methylthiobenzyl | Et | 1 | 79 | 152–153 |

(Me: methyl; Et: ethyl; MeO: methoxy)

TABLE 4

| Cpd. No. | R³ | R¹² | R¹ | R² | n | Yield (%) | M.p. (° C.) |
|---|---|---|---|---|---|---|---|
| 37 | Me | 4-MeO | 1-Naphthylmethyl | Et | 1 | 76 | 167–170 |
| 38 | Me | 4-MeO | 2-Naphthylmethyl | Et | 1 | 95 | 130.5–132 |
| 39 | Me | 2-MeO | 2-Methoxybenzyl | Et | 1 | 90 | 147–148 |
| 40 | Me | 4-MeO | 2-Methoxybenzyl | Et | 2 | 83 | 156–157 |
| 41 | Me | 4-MeO | 2-Methoxybenzyl | Me | 3 | 93 | 139–140 |
| 42 | Me | 4-MeO | 3-Methoxybenzyl | Et | 1 | 91 | 144–145 |
| 43 | Me | 4-MeO | 4-Methoxybenzyl | Et | 1 | 87 | 167–168 |
| 44 | Me | 4-MeO | 2,3-Dimethoxybenzyl | Et | 1 | 86 | 135–137 |
| 45 | Me | 4-MeO | 2,5-Dimethoxybenzyl | Et | 1 | 76 | 180–181 |
| 46 | Me | 3,4-Methylenedioxy | 2-Methylthiobenzyl | Et | 1 | 87 | 145–147 |
| 47 | Me | 3,4-Dimethoxy | 2-Methylthiobenzyl | Et | 1 | 77 | 144–145 |
| 48 | Me | 4-MeO | 2-Hydroxybenzyl | Et | 1 | 84 | 183–184 |
| 49 | Me | 4-MeO | 2-Ethoxybenzyl | Et | 1 | 71 | 138–139 |
| 50 | Me | 4-MeO | 2-Benzyloxybenzyl | Et | 1 | 76 | 120–127 |
| 51 | Me | 4-MeO | 2'-Cyanobiphenylmethyl | Et | 1 | 93 | 187–188 |
| 52 | Me | 4-MeO | 2-Methoxymethoxybenzyl | Et | 1 | 63 | 108–109 |
| 53 | Me | 4-MeO | 2-Benzimidazolmethyl | Et | 1 | 82 | amorphous |
| 54 | Me | 4-MeO | 2-Picolyl | Et | 1 | 80 | 132–133 |
| 55 | Me | 4-MeO | 2-Fluorobenzyl | Et | 1 | 77 | 125–127 |
| 56 | Me | 4-Butyryl | 2-Methylthiobenzyl | Et | 1 | 91 | 124–125 |
| 57 | Me | 4-Ethythiomethyl | 2-Methylthiobenzyl | Et | 1 | 76 | amorphous |

(Me: methyl; Et: ethyl; MeO: methoxy)

TABLE 5

| Cpd. No. | R³ | W | R¹² | R¹ | R² | n | Yield (%) | M.p. (° C.) |
|---|---|---|---|---|---|---|---|---|
| 58 | Me | Sulfonylpiperazinyl | H | 2-Methoxybenzyl | Et | 1 | 93 | amorphous |
| 59 | Me | Carbonyl | H | 2-Methylthiobenzyl | Et | 1 | 88 | 127–128 |
| 60 | Me | Carbonyl | 4-MeO | 2-Methylthiobenzyl | Et | 1 | 94 | 128–129 |

(Me: methyl; Et: ethyl; Meo: methoxy)

Example 8

Production of 2,4(1H,3H)-dioxo-1-(2-methylsulfinylbenzyl)-6-(4-methoxyphenyl)-5-methylthieno[2,3-d]pyrimidine-3-acetate (Compound 61).

A solution of m-chloroperbenzoic acid (0.26 g, 0.753 mmole) in dichloromethane (10 ml) was added dropwise into a solution of the compound produced in Example 7 (0.35 g, 0.685 mmole) in dichloromethane (10 ml) with ice-cooling. After the addition was complete, the mixture was further stirred at 0° C. for 30 minutes. The reaction mixture was poured into a 5% aqueous solution of sodium bicarbonate, the aqueous layer was extracted with ethyl acetate. The combined organic layers were washed with an aqueous solution of sodium chloride, dried over MgSO₄ and evaporated in vacuo. The resulting residue was chromatographed on silica gel to give colorless amorphous crystals (0.26 g; 72%).

m.p. 90–95° C.

Elemental analysis (%) for $C_{26}H_{26}N_2O_6S_2 \cdot 0.2H_2O$: Calcd.: C 58.89, H 5.01, N 5.28; Found: C 58.89, H 5.04, N 5.22.

¹H-NMR (200 MHz, DMSO-d₆) δ: 1.31 (3H, t, J=7.1 Hz), 2.50 (3H, s), 2.83 (3H, s), 3.83 (3H, s), 4.25 (2H, q, J=7.1 Hz), 4.82 (2H, s), 5.19 (1H, d, J=16.2 Hz), 5.49 (1H, d, J=16.2 Hz), 6.93 (2H, d, J=8.8 Hz), 7.23–7.57 (5H, m), 8.05 (1H, d, J=7.8 Hz).

IR (KBr): 1748, 1709, 1665, 1609, 1564, 1535 cm⁻¹.

Example 9

Production of ethyl 2,4(1H,3H)-dioxo-1-(2-methylsulfonylbenzyl)-6-(4-methoxyphenyl)-5-methylthieno[2,3-d]pyrimidine-3-acetate (Compound 62).

A solution of m-chloroperbenzoic acid (0.52 g, 1.51 mmoles) in dichloromethane (10 ml) was added dropwise into a solution of the compound 34 produced in Example 6 (0.35 g, 0.685 mmole) in dichloromethane (10 ml) with ice-cooling. After the addition was complete, the mixture was stirred at 0C for one hour and then at room temperature for 4 hours. The reaction mixture was poured into a 5% aqueous solution of sodium bicarbonate, the aqueous layer was extracted with ethyl acetate. The combined organic layers were washed with an aqueous solution of sodium chloride, dried over MgSO₄ and evaporated in vacuo. The resulting residue was chromatographed on silica gel to give a pale yellow solid (0.37 g; 99%), which was recrystallized from ethyl acetate-hexane to give 0.25 g (67%) of colorless crystals.

m.p. 141–144° C.

Elemental analysis (%) for $C_{26}H_{26}N_2O_7S_2 \cdot H_2O$: Calcd.: C 57.55, H 4.83, N 5.16; Found: C 57.64, H 4.69, N 5.16.

¹H-NMR (200 MHz, DMSO-d₆) δ: 1.28 (3H, t, J=7.1 Hz), 2.53 (3H, s), 3.26 (3H, s), 3.84 (3H, s), 4.23 (2H, q, J=7.1 Hz), 4.79 (2H, s), 5.64 (2H, s), 6.94 (2H d, J=8.9 Hz), 7.22–7.32 (3H, m), 7.48–7.64 (2H, m), 8.11 (1H, d, J=7.6 Hz).

IR (KBr): 1742, 1705, 1661, 1533, 1477, 1377 cm⁻¹.

Example 10

Production of ethyl 5-bromomethyl-2,4(1H,3H)-dioxo-1-(2-methoxybenzyl)-6-phenylthieno[2,3-d]pyrimidine-3-acetate (Compound 63).

A mixture of the compound 23 produced in Example 7 (0.20 g, 0.431 mmole), N-bromosuccinimide (80 mg, 0.45 mmole), α,α'-azobisisobutyronitrile (7 mg, 0.043 mmole) and carbon tetrachloride (5 ml) was refluxed for two hours. After cooling, the insoluble matter was filtered off and the filtrate was diluted with chloroform. The organic layer was washed with an aqueous solution of sodium chloride, dried over MgSO₄ and evaporated in vacuo. The resulting residue was chromatographed on silica gel to give a solid, which was crystallized from ether-hexane to give colorless crystals (0.204 g; 87%).

m.p. 123–124° C.

Elemental analysis (%) for $C_{25}H_{23}N_2O_5SBr$: Calcd.: C 55.25, H 4.27, N 5.15; Found: C 55.04, H 4.21, N 5.01.

¹H-NMR (200 MHz, CDCl₃) δ: 1.30 (3H, t, J=7.1 HZ), 3.87 (3H, s), 4.25 (2H, q, J=7.1 Hz), 4.80 (2H, s), 4.86 (2H, s), 5.26 (2H, s), 6.88–6.96 (2H, m), 7.15–7.19 (1H, m), 7.25–7.58 (6, m).

IR (KBr): 2974, 1754, 1713, 1663, 1555, 1531, 1493, 1479 cm⁻¹.

Example 11

Production of ethyl 2,4(1H,3H)-dioxo-1-(2-methoxybenzyl)-5-{(N-methyl-N-phenyl)aminomethyl}-6-phenylthieno[2,3-d]pyrimidine-3-acetate (Compound 64).

To a solution of the compound 60 produced in Example 10 (0.72 g, 1.32 mmoles) in dimethylformamide (6 ml) was added triethylamine (0.28 ml, 2.0 mmoles) followed by adding N-methylaniline (0.22 ml, 2.03 mmoles) thereto. The mixture was stirred at room temperature for 4 hours. The reaction mixture was concentrated and the resulting residue was partitioned between ethyl acetate and an aqueous solution of sodium chloride. The aqueous layer was extracted with ethyl acetate. The combined organic layers were washed with an aqueous solution of sodium chloride, dried over MgSO₄ and evaporated in vacuo. The resulting residue was chromatographed on silica gel to give white amorphous powders (0.45 g; 60%).

¹H-NMR (200 MHz, CDCl₃) δ: 1.30 (3H t, J=7.2 Hz), 2.60 (3H, s), 3.86 (3H, s), 4.25 (2H, q, J=7.2 Hz), 4.72 (2H, s), 4.84 (2H, s), 5.26 (2H, s), 6.65–6.72 (3H, m), 6.88–6.96 (2H, m), 7.10–7.37 (9H, m).

IR (KBr): 2966, 1752, 1711, 1667, 1601, 1560, 1531, 1493, 1473 cm⁻¹.

Example 12

Production of ethyl 2,4(1H,3H)-dioxo-6-(4-hydroxyphenyl)-1-(2-methoxybenzyl)-5-methylthieno[2,3-d]pyrimidine-3-acetate (Compound 65).

Acetic anhydride (3 ml; 31.8 mmoles) was added to a solution of the compound 11 produced in Example 4 (0.60 g, 1.66 mmoles) in pyridine (8 ml) and the mixture was stirred at room temperature for three hours. The reaction mixture was concentrated and the residue was partitioned between ethyl acetate and diluted hydrochloric acid. The aqueous layer was extracted with ethyl acetate. The combined organic layers were washed with an aqueous solution of sodium chloride, dried over MgSO₄ and evaporated in vacuo. The residue was chromatographed on silica gel to give white amorphous powders (0.57 g). To a solution of the resulting amorphous powders in dimethylformamide (5 ml) were added potassium carbonate (0.38 g, 2.75 mmoles) and 2-methoxybenzyl chloride (0.65 g, 4.15 mmoles). The mixture was stirred at room temperature for 22 hours. The reaction mixture was concentrated and the residue was partitioned between ethyl acetate and an aqueous solution of sodium chloride. The aqueous layer was extracted with ethyl acetate. The combined organic layers were washed with an aqueous solution of sodium chloride, dried over MgSO₄ and was evaporated in vacuo. The residue was chromatographed on silica gel to give amorphous powders (0.60 g). The amorphous powders were dissolved in a mixture of methanol (18 ml) and tetrahydrofuran (12 ml). To this solution was added dropwise a solution of potassium carbonate (0.313 g, 2.26 mmoles) in water (8 ml). The mixture was stirred at room temperature for 30 minutes, and then 1N hydrochloric acid (5 ml) was added thereto with ice-cooling. The mixture was extracted with ethyl acetate. The extract was washed with an aqueous solution of sodium chloride, dried over MgSO₄ and evaporated in vacuo. The residue was crystallized from ether to give colorless crystals (0.496 g; 62%).

m.p. 207–208° C.

Elemental analysis (%) for $C_{25}H_{24}N_2O_6S$: Calcd.: C 62.49, H 5.03, N 5.83; Found: C 62.50, H 5.21, N 5.85.

¹H-NMR (200 MHz, CDCl₃) δ: 1.32 (3H, t, J=7.1 Hz), 2.43 (3H, s), 3.85 (3H, s), 4.27 (2H, q, J=7.1 Hz), 4.85 (2H, s), 5.19 (2H, s), 5.78 (1H, s), 6.74–6.91 (4H, m), 7.05–7.11 (3H, m), 7.21–7.30 (1H, m).

IR (KBr): 3350, 2976, 1756, 1698, 1649, 1613, 1566, 1537, 1483 cm⁻¹.

Example 13

Production of ethyl 2,4(1H,3H)-dioxo-6-(4-hydroxyphenyl)-1-(2-methylthiobenzyl)-5-methylthieno[2,3-d]pyrimidine-3-acetate (Compound 66).

Acetic anhydride (3 ml; 31.8 mmoles) was added to a solution of the compound 11 produced in Example 4 (0.60 g, 1.66 mmoles) in pyridine (8 ml) and the mixture was stirred at room temperature for three hours. The reaction mixture was concentrated and the residue was partitioned between ethyl acetate and diluted hydrochloric acid. The aqueous layer was extracted with ethyl acetate. The combined organic extracts were washed with an aqueous solution of sodium chloride, dried over MgSO₄ and evaporated in vacuo. The residue was chromatographed on silica gel to give a white amorphous (0.57 g). To a solution of the resulting amorphous in dimethylformamide (5 ml) were added potassium carbonate (0.38 g, 2.75 mmoles) and 2-methylthiobenzyl chloride (0.65 g, 4.15 mmoles). The mixture was stirred at room temperature for 22 hours. The reaction mixture was concentrated and the residue was partitioned between ethyl acetate and an aqueous solution of sodium chloride. The aqueous layer was extracted with ethyl acetate. The combined organic extracts were dried over MgSO₄ and evaporated in vacuo. The residue was chromatographed on silica gel to give a white amorphous (0.60 g). The amorphous was dissolved in a mixture of methanol (18 ml) and tetrahydrofuran (12 ml) and a solution of potassium carbonate (0.313 g, 2.26 mmoles) in water (8 ml)

was added dropwise thereinto. The mixture was stirred at room temperature for 30 minutes. To the reaction mixture was added dropwise 1N hydrochloric acid (5 ml) with ice-cooling and the mixture was extracted with ethyl acetate. The extract was washed with an aqueous solution of sodium chloride, dried over MgSO$_4$ and evaporated in vacuo. The residue was crystallized from ether to give colorless crystals (4.33 g; 78%).

m.p. 177–178° C.

Elemental analysis (%) for $C_{25}H_{24}N_2O_5S_2 \cdot 1/10H_2O$: Calcd.: C 60.25, H 4.89, N 5.62; Found: C 60.09, H 4.66, N 5.57.

$^1$H-NMR (200 MHz, CDCl$_3$) δ: 1.32 (3H, t, J 7.2 Hz), 2.45 (3H, s), 2.52 (3H, s), 4.28 (2H, q, J=7.2 Hz), 4.87 (2H, s), 5.28 (2H, s), 5.75 (1H, s), 6.78 (2H, d, J=8.6 Hz), 6.97–7.14 (4H, m), 7.21–7.34 (2H, m).

IR (KBr): 3346, 2978, 1752, 1700, 1651, 1613, 1591, 1564, 1535, 1481 cm$^{-1}$.

Example 14

Production of ethyl 2,4(1H,3H)-dioxo-6-(4-ethoxyphenyl)-1-(2-methoxybenzyl)-5-methythieno[2,3-d]pyrimidine-3-acetate (Compound 67).

A solution of the compound 62 produced in Example 12 (0.15 g, 0.31 mmole) in dimethylformamide (3 ml) was added dropwise into a suspension of sodium hydride (14 mg, 0.35 mmole) in dimethylformamide (1 ml) with ice-cooling under nitrogen stream. The mixture was stirred with ice-cooling for 30 minutes. To this mixture was added dropwise iodoethane (0.13 ml, 1.63 mmoles). The mixture was stirred at room temperature for 2.5 hours. The reaction mixture was concentrated and the residue was partitioned between ethyl acetate and an aqueous solution of ammonium chloride. The aqueous layer was extracted with ethyl acetate. The combined extracts were washed with an aqueous solution of sodium chloride, dried over MgSO$_4$ and evaporated in vacuo. The resulting residue was recrystallized from ethyl acetate-hexane to give colorless crystals (0.119 g; 75%).

m.p. 133–134° C.

Elemental analysis (%) for $C_{27}H_{28}N_2O_6S$: Calcd.: C 63.76, H 5.55, N 5.51; Found: C 63.48, H 5.62, N 5.37.

$^1$H-NMR (200 MHz, CDCl$_3$) δ: 130 (3H, t, J 7.1 Hz), 1.43 (3H, t, J=7.0 Hz), 2.49 (3H, s), 3.87 (3H, s), 4.05 (2H, q, J=7.0 Hz), 4.25 (2H, q, J=7.1 H), 4.83 (2H, s), 5.24 (2H, s), 6.86–6.94 (4H, m), 7.09–7.14 (1H, m), 7.22–7.31 (3H, m).

IR (KBr): 2984, 1758, 1707, 1665, 1607, 1562, 1535, 1477 cm$^{-1}$.

Example 15

The compounds listed in Table 6 were produced from the compound prodced in Example 12 by the same method as mentioned in Example 14.

TABLE 6

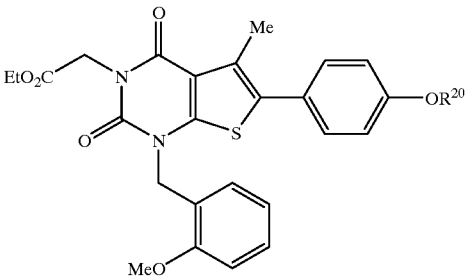

| Cpd. No. | R$^{20}$ | Yield (%) | M.p. (° C.) |
|---|---|---|---|
| 68 | 2-Methoxybenzyl | 92 | 142–143 |
| 69 | 2-Hydroxyethyl | 54 | 116–117 |
| 70 | Isopropyl | 72 | amorphous |
| 71 | Methoxymethyl | 92 | 96–97 |
| 72 | Methoxyethyl | 79 | 134–135 |
| 73 | Methylthiomethyl | 75 | 74–79 |
| 74 | Acetic Acid | 96 | 147–148 |
| 75 | Benzyl | 94 | 60–70 |
| 76 | Carbamoylmethyl | 98 | 170–171 |
| 77 | tert-Butoxycarbonyl | 100 | amorphous |
| 78 | Methylamide | 97 | 156–157 |

Example 16

The compounds listed in Table 7 were produced from the compound produced in Example 13 by the same method as mentioned in Example 14.

TABLE 7

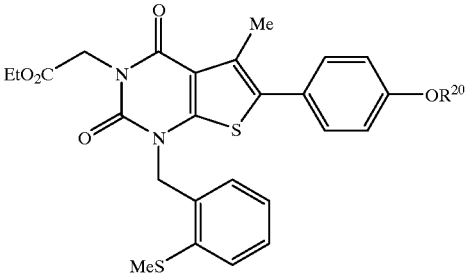

| Cpd. No. | R$^{20}$ | Yield (%) | M.p. (° C.) |
|---|---|---|---|
| 79 | Methoxymethyl | 85 | amorphous |
| 80 | Methylthiomethyl | 77 | 110–111 |
| 81 | n-Propyl | 84 | 122–123 |
| 82 | Methoxyethoxymethyl | 89 | amorphous |
| 83 | 2-Oxopropyl | 48 | 127–128 |
| 84 | n-Butyl | 85 | 85–88 |
| 85 | Allyl | 76 | 115–117 |
| 86 | Acetyl | 67 | amorphous |

Example 17

Production of ethyl 2,4(1H,3H)-dioxo-6-(N'-phenylpiperaznylsulfamoyl)-5-methylthieno[2,3-d]pyrimidine-3-acetate (Compound 87).

To the compound produced in Referential Example 6 (0.54 g; 2.0 moles) was added chlorosulfonic acid (4 ml) and the mixture was stirred at 70° C. for one hour. After cooling, the reaction mixture was poured into ice-water and extracted with ethyl acetate. The combined organic extracts were washed with an aqueous solution of sodium chloride, dried over MgSO$_4$ and evaporated in vacuo. The residue was dissolved in dimethylformamide (6 ml). To the solution were added triethylamine (0.61 ml, 4.38 mmoles) and 1-phenylpiperazine (0.34 ml, 2.23 mmoles) with ice-cooling and the mixture was stirred for one hour. The reaction mixture was concentrated and the residue was partitioned between ethyl acetate-tetrahydrofuran and diluted hydrochloric acid. The aqueous layer was extracted with ethyl acetate-tetrahydrofuran. The combined organic extracts were washed with an aqueous solution of sodium chloride, dried over MgSO$_4$ and evaporated in vacuo to give a solid (0.38 g). The resulting solid was dissolved in ethanol (30 ml). To the solution was added concentrated sulfuric acid (0.1 ml) and the mixture was refluxed for 14 hours. After cooling, the reaction mixture was partitioned between ethyl acetate and a saturated aqueous solution of sodium bicarbonate. The aqueous layer was extracted with ethyl acetate. The combined organic extracts were washed with an aqueous solution of sodium chloride, dried over MgSO$_4$ and evaporated in vacuo. The residue was chromatographed on silica gel to give a white solid (0.135 g; 14%). This was recrystallized from ethyl acetate to give colorless crystals.

m.p. 259–260° C.

Elemental analysis (%) for C$_{21}$H$_{24}$N$_4$O$_6$S$_2$: Calcd.: C 51.21, H 4.91, N 11.37; Found: C 51.20, H 5.03, N 11.26.

$^1$H-NMR (200 MHz, CDCl$_3$) δ: 1.21 (3H, t, J=7.2 Hz), 2.66 (3H, s), 3.23 (8H, s), 4.14 (2H q, J=7.1 Hz), 4.57 (2H, s), 6.77–6.94 (3H, m), 7.16–7.25 (2H, m).

IR (KBr): 3138, 1740, 1721, 1680, 1651, 1603, 1564, 1520, 1497 cm$^{-1}$.

Example 18

Production of ethyl 2,4(1H,3H)-dioxo-6-benzoyl-5-methyl-thi no[2,3-d]pyrimidine-3-acetate (Compound 88).

To a suspension of the compound produced in Reference Example 6 (0.54 g, 2.0 mmoles) in nitromethane (10 ml) were added aluminum chloride (1.13 g, 8.47 mmoles) and benzoyl chloride (0.48 ml, 4.14 mmoles) under nitrogen stream and then stirred 2 hours. The mixture was stirred at 40° C. for 6 hours. After cooling, the reaction mixture was poured into ice-water and extracted with ethyl acetate. The combined organic extracts were washed with an aqueous solution of sodium chloride, dried over MgSO$_4$ and evaporated in vacuo. The resulting residue was recrystallized from ether-ethyl acetate to give colorless crystals (0.56 g; 74%).

m.p. 202–203° C.

Elemental analysis (%) for C$_{18}$H$_{16}$N$_2$O$_5$S: Calcd.: C 58.06, H 4.33, N 7.52; Found: C 57.80, H 4.40, N 7.37.

$^1$H-NMR (200 MHz, CDCl$_3$) δ: 1.22 (3H, t, J 7.2 Hz), 2.45 (3H, s), 4.15 (2H, q, J=7.2 Hz), 4.59 (2H, s), 7.51–7.74 (5H, m).

IR (KBr): 3190, 1734, 1709, 1678, 1609, 1557, 1553 cm$^{-1}$.

Example 19

Production of ethyl 2,4(1H,3H)-dioxo-6-(4-methoxybenzoyl)-5-methylthieno[2,3-d]pyrimidine-3-acetate (Compound 89).

The same operations as in Example 18 were carried out by using 4-methoxybenzoyl chloride (0.515 g, 3.0 mmoles) instead of benzoyl chloride to give colorless plates (0.34 g; 42%).

m.p. 209–211° C.

Elemental analysis (%) for C$_{19}$H$_{18}$N$_2$O$_6$S.0.1H$_2$O: Calcd.: C 56.46, H 4.54, N 6.93; Found: C 56.36, H 4.74, N 6.74.

$^1$H-NMR (200 MHz, CDCl$_3$) δ: 1.31 (3H, t, J=7.1 Hz), 2.51 (3H, s), 3.90 (3H, s), 4.26 (2H, q, J=7.1 Hz), 4.76 (2H, s), 6.97 (2H, d, J=8.9 Hz), 7.77 (2H,d, J=8.9 Hz).

IR (KBr): 3124, 2972, 1734, 1669, 1593, 1562, 1543, 1510 cm$^{-1}$.

Example 20

Production of ethyl 2,4(1H,3H)-dioxo-1-(2-methylthiobenzyl)-6-(4-methoxybenzamido)-5-methylthieno[2,3-d]pyrimidine-3-acetate (Compound 90).

To a solution of the compound produced in Reference Example 10 (0.60 g, 1.30 mmoles) in dichloromethane (35 ml) were added 4-dimethylaminopyridine (0.027 g; 0.23 mmole) and triethylamine (0.35 ml, 2.5 mmoles). To this solution was added dropwise a solution of 4-methoxybenzoyl chloride (0.3 ml, 2.6 mmoles) in dichloromethane (5 ml). After the addition was complete, the mixture was stirred at room temperature for 1.5 hours. The reaction mixture was partitioned between dichloromethane and a saturated aqueous solution of sodium chloride. The aqueous layer was extracted with dichloromethane. The combined organic extracts were washed with an aqueous solution of sodium chloride, dried over MgSO$_4$ and evaporated in vacuo. The residue was chromatographed on silica gel to give white amorphous powders (0.46 g). The amorphous powders (0.3 g; 0.52 mmole) were dissolved in a mixture of methanol (6 ml) and tetrahydrofuran (6 ml). To the mixture was added a solution of potassium carbonate (0.15 g) in water (3 ml) and the mixture was stirred at room temperature for 10 minutes. To the reaction mixture was added 1N hydrochloric acid (1.5 ml) at 0C and the mixture was extracted with ethyl acetate. The combined organic extracts were washed with an aqueous solution of sodium chloride, dried over MgSO$_4$ and evaporated in vacuo. The residue was chromatographed on silica gel to give white powdery crystals (0.20 g; 70%), which were recrystallized from ethyl acetate-hexane.

m.p. 199–200° C.

Elemental analysis (%) for C$_{27}$H$_{27}$N$_3$O$_6$S$_2$: Calcd.: C 58.57, H 4.92, N 7.59; Found: C 58.58, H 5.06, N 7.36.

$^1$H-NMR (200 MHz, CDCl$_3$) δ: 1.30 (3H, t, J=7.2 Hz), 2.53 (3H, s), 2.58 (3H, s), 3.88 (3H, s), 4.25 (2H, q, J=7.2 Hz), 4.84 (2H, s), 5.34 (2H, s), 6.94–7.33 (7H, m), 7.80 (1H, d).

IR (KBr): 3358, 2982, 1746, 1702, 1661, 1607, 1493 cm$^{-1}$.

Example 21

Production of ethyl 2,4(1H,3H)-dioxo-1-(2-methoxybenzyl)-6-benzamido-5-methylthieno[2,3-d]pyrimidine-3-acetate (Compound 91).

The same operations as in Example 20 were carried out with the compound obtained in Reference Example 11 instead of 4-methoxybenzoyl chloride to give colorless powdery crystals (0.06 g; 53%).

$^1$H-NMR (200 MHz, CDCl$_3$) δ: 1.29 (3H, t, J=7.1 Hz), 2.51 (3H, s), 3.91 (3H, s), 4.24 (2H, q, J=7.1 Hz), 4.81 (2H, s), 5.25 (2H, s), 6.83–6.91 (2H, m), 7.05–7.09 (1H, m) 7.21–7.30 (1H, m), 7.46–7.59 (3H, m), 7.82–7.87 (2H, m), 8.05 (1H, s).

Example 22

Production of 2,4(1H,3H)-dioxo-1-(2-methoxybenzyl)-6-phenylthieno[2,3-d]pyrimidine-3-acetic acid (Compound 92).

The compound 12 (0.20 g; 0.44 mmole) produced in Example 5 was dissolved in a mixture of methanol (6 ml) and tetrahydrofuran (12 ml). To the solution was added dropwise 1N sodium hydroxide solution (2 ml, 2 mmoles). After stirring the mixture at room temperature for three hours, 1N hydrochloric acid (3 ml) was added to the reaction mixture with ice-cooling and the mixture was extracted with ethyl acetate. The extract was washed with an aqueous solution of sodium chloride, dried over $MgSO_4$ and evaporated in vacuo. The residue was recrystallized from ethanol to give pale yellow crystals (0.153 g; 82%).

m.p. 272–273° C.

Elemental analysis (%) for $C_{22}H_{18}N_2O_5S$: Calcd.: C 62.55, H 4.29, N 6.63; Found: C 62.52, H 4.37, N 6.89.

$^1$H-NMR (200 MHz, DMSO-$d_6$) δ: 3.88 (3H, s), 4.62 (2H, s), 5.18 (2H, s), 6.86–6.94 (1H, m), 706–7.10 (2H, m), 7.28–7.45 (4H, m),7.62–7.66 (2H, m), 7.72 (1H, s).

IR (KBr): 3128, 1730, 1710, 1659, 1560, 1526, 1497, 1475 cm$^{-1}$.

Example 23

The compounds listed in Tables 8, 9, 10, 11 and 12 were produced by the same manner as mentioned in Example 22 from the compounds produced in Examples 2, 6, 7, 8, 9, 10, 11, 12, 13, 14, 16, 19, 20, 21, 30, 31, 33, 34, 35 and 36.

TABLE 8

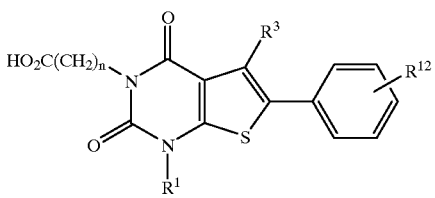

| Cpd. No. | $R^3$ | $R^{12}$ | $R^1$ | n | Yield (%) | M.p. (° C.) |
|---|---|---|---|---|---|---|
| 93 | H | H | 2-(1-Methylindol-3-yl)ethyl | 1 | 60 | 269–271 |
| 94 | H | H | 2-Quinolylmethyl | 1 | 57 | >300 |
| 95 | H | H | 3,4-Methylenedioxybenzyl | 1 | 67 | 215–218 |
| 96 | H | H | 2-Methoxybenzyl | 2 | 85 | 240–241 |
| 97 | H | H | 2-Methoxybenzyl | 3 | 59 | 186–188 |
| 98 | H | H | Cyclohexylmethyl | 1 | 79 | 249–251 |
| 99 | H | H | 3-Methoxybenzyl | 1 | 91 | 240–243 |

TABLE 8-continued

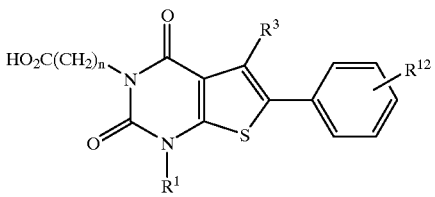

| Cpd. No. | $R^3$ | $R^{12}$ | $R^1$ | n | Yield (%) | M.p. (° C.) |
|---|---|---|---|---|---|---|
| 100 | H | H | 4-Methoxybenzyl | 1 | 90 | 209–211 |
| 101 | H | H | 2-Methoxyphenethyl | 1 | 67 | 220–221 |
| 102 | Methyl | H | 2-Methoxybenzyl | 1 | 79 | 252–255 |

TABLE 9

| Cpd. No. | $R^3$ | $R^{12}$ | $R^1$ | n | Yield (%) | M.p. (° C.) |
|---|---|---|---|---|---|---|
| 103 | Me | H | 2-(1-Methylindol-3-yl)ethyl | 1 | 75 | 254–255 |
| 104 | * | H | 2-Methoxybenzyl | 1 | 90 | 180–185 |
| 105 | Me | 4-MeO | 2-Methoxybenzyl | 1 | 93 | 216–218 |
| 106 | Me | 4-Meo | 2-(1-Methylindol-3-yl)ethyl | 1 | 88 | 249–251 |
| 107 | Me | 4-Nitro | 2-Methoxybenzyl | 1 | 78 | >300 |
| 108 | Me | 4-MeO | H | 1 | 58 | 271–273.5 |
| 109 | Me | 4-MeO | Butyl | 1 | 96 | 195–197 |
| 110 | Me | 4-MeO | Benzyl | 1 | 78 | 194–194.5 |
| 111 | Me | 4-MeO | 2-Methylbenzyl | 1 | 87 | 239–240 |
| 112 | Me | 4-MeO | 2-Bromobenzyl | 1 | 86 | 231–233 |

(Me: methyl; MeO: methoxy; *: (N-Methyl-N-phenyl)aminomethyl)

TABLE 10

| Cpd. No. | $R^3$ | $R^{12}$ | $R^1$ | n | Yield (%) | M.p. (° C.) |
|---|---|---|---|---|---|---|
| 113 | Me | 4-MeO | 2-Nitrobenzyl | 1 | 58 | 190–191 |
| 114 | Me | 4-MeO | 2-Cyanobenzyl | 1 | 71 | 260–262 |
| 115 | Me | 4-MeO | 2-Methylthiobenzyl | 1 | 87 | 185–189 |
| 116 | Me | 4-MeO | 2-Methoxyphenethyl | 1 | 82 | 201.5–203 |
| 117 | Me | 4-MeO | 1-Naphthylmethyl | 1 | 83 | 209–210.5 |
| 118 | Me | 4-MeO | 2-Naphthylmethyl | 1 | 68 | 254–258 |
| 119 | Me | 2-MeO | 2-Methoxybenzyl | 1 | 67 | 216–217.5 |
| 120 | Me | 4-MeO | 2-Methoxybenzyl | 2 | 84 | 231–233 |
| 121 | Me | 4-MeO | 2-Methoxybenzyl | 3 | 86 | 190–191 |
| 122 | Me | 4-MeO | 3-Methoxybenzyl | 1 | 54 | 181–182 |

TABLE 11

| Cpd. No. | $R^3$ | $R^{12}$ | $R^1$ | n | Yield (%) | M.p. (° C.) |
|---|---|---|---|---|---|---|
| 123 | Me | 4-Methoxy | 4-Methoxybenzyl | 1 | 81 | 193–195 |
| 124 | Me | 4-Methoxy | 2,3-Dimethoxybenzyl | 1 | 59 | 192–914 |
| 125 | Me | 4-Methoxy | 2,5-Dimethoxybenzyl | 1 | 73 | 176–178 |
| 126 | Me | 4-Hydroxy | 2-Methoxybenzyl | 1 | 69 | 232–234 |
| 127 | Me | 4-(2-Methoxybenzyloxy) | 2-Methoxybenzyl | 1 | 82 | 123–124.5 |
| 128 | Me | 4-Ethoxy | 2-Methoxybenzyl | 1 | 66 | 227–228 |
| 129 | Me | 4-iso-Propoxy | 2-Methoxybenzyl | 1 | 80 | 220–223 |
| 130 | Me | 4-(2-Hydroxyethoxy) | 2-Methoxybenzyl | 1 | 67 | 198–200 |
| 131 | Me | 4-Methoxymethoxy | 2-Methoxybenzyl | 1 | 88 | 149–151 |
| 132 | Me | 4-Methoxy | 2-Hydroxybenzyl | 1 | 64 | 250–254 |

TABLE 11-continued

| Cpd. No. | R³ | R¹² | R¹ | n | Yield (%) | M.p. (° C.) |
|---|---|---|---|---|---|---|
| 133 | Me | 4-Methoxy | 2-Ethoxybenzyl | 1 | 88 | 167–170 |
| 134 | Me | 4-Methoxy | 2-Benzyloxybenzyl | 1 | 62 | 200–202 |
| 135 | Me | 4-Methoxy | 2'-Cyanobiphenyl-methyl | 1 | 84 | 214–215 |
| 136 | Me | 4-Methoxy | 2-Methoxymethoxy-benzyl | 1 | 76 | 151–153 |
| 137 | Me | 4-Methoxy | 2-Benzimidazol-methyl | 1 | 54 | >300 |
| 138 | Me | 4-Methoxy | 2-Picolyl | 1 | 83 | 262–265 |
| 139 | Me | 4-Methoxy-ethoxy | 2-Methoxybenzyl | 1 | 86 | 192–193 |
| 140 | Me | 4-Methyl-thiomethoxy | 2-Methoxybenzyl | 1 | 82 | 164–168 |
| 141 | Me | 4-Carboxyl-methoxy | 2-Methoxybenzyl | 1 | 65 | 212–215 |
| 142 | Me | 4-Benzyloxy | 2-Methoxybenzyl | 1 | 76 | 206–207 |
| 143 | Me | 4-Carbamoyl-methoxy | 2-Methoxybenzyl | 1 | 76 | 243–248 |
| 144 | Me | 4-Methoxy-methoxy | 2-Methylthiobenzyl | 1 | 79 | 142–144 |
| 145 | Me | 4-Methyl-thiomethoxy | 2-Methylthiobenzyl | 1 | 79 | 152–154 |
| 146 | Me | 4-n-Propoxy | 2-Methylthiobenzyl | 1 | 78 | 185–188 |
| 147 | Me | 4-Methoxyeth-oxymethoxy | 2-Methylthiobenzyl | 1 | 86 | 150–155 |
| 148 | Me | 4-(2-Oxoprop-oxy) | 2-Methylthiobenzyl | 1 | 78 | 285–290 |
| 149 | Me | 4-Methoxy | 2-Methylsulfinyl-benzyl | 1 | 67 | 223–224 |
| 150 | Me | 4-Methoxy | 2-Methylsulfonyl-benzyl | 1 | 96 | 142–145 |
| 151 | Me | 4-n-Butoxy | 2-Methylthiobenzyl | 1 | 72 | 178–180 |
| 152 | Me | 4-Methoxy | 2-Fluorobenzyl | 1 | 59 | 196–197 |
| 153 | Me | 4-Allyloxy | 2-Methylthiobenzyl | 1 | 81 | 198–200 |
| 154 | Me | 4-Methoxy | 2-tert-Butoxycarb-onylbenzyl | 1 | 95 | 140–144 |
| 155 | Me | 4-Methoxy | 2-Carboxybenzyl | 1 | 86 | 289–291 |
| 156 | Me | 3,4-Methylene-dioxy | 2-Methylthiobenzyll | 1 | 94 | 205–210 |
| 157 | Me | 3,4-Dimethoxy | 2-Methilthiobenzyl | 1 | 78 | 203–205 |
| 158 | Me | 4-Methoxy | 2,4-Dimethoxybenzyl | 1 | 82 | 203–204 |
| 159 | Me | 4-Butyryl | 2-Methylthiobenzyl | 1 | 54 | 197–199 |
| 160 | Me | 4-Etylthio-methyl | 2-Methylthiobenzyl | 1 | 43 | 286–289 |
| 161 | Me | 4-Methoxy | 2-Aminobenzyl | 1 | 48 | 209–212 |
| 162 | Me | 4-Methoxy | 2-Methylaminobenzyl | 1 | 58 | 204–206 |
| 163 | * | 4-Methoxy-methoxy | 2-Methoxybenxyl | 1 | 91 | 220–225 |
| 164 | Me | 4-Hydroxyl | 2-Methylthiobenzyl | 1 | 72 | 244–246 |
| 165 | Me | 4-Phenyl | 2-Methylthiobenzyl | 1 | 53 | 270–273 |
| 166 | Me | 4-Methoxyethyl | 2-Methylthiobenzyl | 1 | 73 | 186–187 |

(Me: methyl, *: hydroxymethyl)

TABLE 12

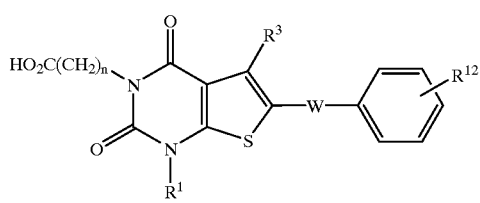

| Cpd. No. | R³ | W | R¹² | R¹ | n | Yield (%) | M.p. (° C.) |
|---|---|---|---|---|---|---|---|
| 167 | Me | Sulfo-piper-azinyl | H | 2-Methoxy-benzyl | 1 | 58 | 239–242 |
| 168 | Me | Carbonyl | H | 2-Methylthio-benzyl | 1 | 27 | 214–216 |

TABLE 12-continued

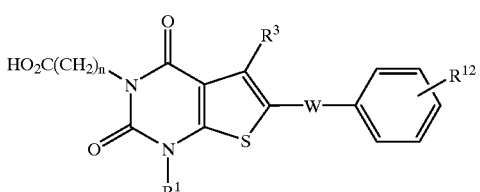

| Cpd. No. | R³ | W | R¹² | R¹ | n | Yield (%) | M.p. (° C.) |
|---|---|---|---|---|---|---|---|
| 169 | Me | Carbonyl | 4-MeO | 2-Methylthio-benzyl | 1 | 58 | 202–206 |
| 170 | Me | Amide | 4-MeO | 2-Methylthio- | 1 | 83 | >300 |

TABLE 12-continued

[Structure: HO₂C(CH₂)ₙ-N attached to thieno[2,3-d]pyrimidine-2,4-dione core with R³ at position 5, W-phenyl-R¹² at position 6, and R¹ on N1]

| Cpd. No. | R³ | W | R¹² | R¹ | n | Yield (%) | M.p. (° C.) |
|---|---|---|---|---|---|---|---|
| benzyl | | | | | | | |

(Me: methyl)

Example 24

Production of ethyl 2,4(1H,3H)-dioxo-1-(2-methylthiobenzyl)-6-(4-aminophenyl)-5-methylthieno[2,3-d]pyrimidine-3-acetate (Compound 171).

To a solution of the compound produced in Example 7 (Compound 36, 3.0 g, 6.48 mmoles) in ethanol (40 ml) were added iron powder (1.2 g) and concentrated hydrochloric acid (2.0 ml). The mixture was refluxed for 30 minutes. After cooling, the reaction mixture was filtered through cellite (10 g), the filtrate was concentrated to dryness. The residue was partitioned between ethyl acetate (100 ml) and a saturated aqueous solution of sodium bicarbonate (30 ml). The aqueous layer was extracted with ethyl acetate. The combined organic extracts were washed with an aqueous solution of sodium chloride, dried over MgSO₄ and evaporated in vacuo. The residue was recrystalized from ethyl acetate-isopropylether to give colorless prisms (2.08 g, 69%).

M.p. 172–173° C.

Elemental analysis (%) for $C_{25}H_{25}N_3O_4S_2$: Calcd.: C 60.59, H 5.08, N 8.48 Found: C 60.56, H 4.93, N 8.49.

¹H-NMR (500 MHz, CDCl₃) δ: 1.30 (3H, t, J=7.0 Hz), 2.49 (3H, s), 2.52 (3H, s), 3.80 (2H br s), 4.25 (2H, q, J=7.1 Hz), 4.84 (2H, s), 5.33 (2H, s), 6.66(2H, d, J=8.3 Hz), 7.02 (1H, d, J=7.7 Hz), 7.12 (2H, d J=8.3 Hz), 7.14 (1H, t, J=8.1 Hz), 7.25 (1H, t, J=8.1 Hz), 7.33 (1H, d, J=7.8 Hz).

Example 25

Production of ethyl 2,4(1H,3H)-dioxo-6-benzoyl-1-(2-methylbenzyl)-6-[4-(1-pyroryl)phenyl]-5-methylthieno[2,3-d]pyrimidine-3-acetate (Compound 172).

To a suspension of the compound produced in Example 6 (0.3 g, 0.65 mmoles) in acetic acid (5 ml) were added 2,5-dimethoxytetrahydrofurane (0.086 g) and sodium acetate (53 mg) and the mixture was refluxed for 30 minutes. The reaction mixture was concentrated and the residue was partitioned between ethy acetate (50 ml) and a saturated aqueous solution of ammonium chloride (30 ml). The aqueous layer was extracted with ethyl acetate (30 ml). The combined organic extracts were washed with an aqueous solution of sodium chloride, dried over MgSO₄ and evaporated in vacuo. The resulting residue was chromatographed on silica gel to give a white solid which was recrystallized from ether-ethyl acetate to give colorless prisms (0.28 g; 80%).

m.p. 156–158° C.

Elemental analysis (%) for $C_{29}H_{27}N_3O_4S_2$: Calcd.: C 63.83, H 4.99, N 7.70; Found: C 63.64, H 4.99, N 7.59.

¹H-NMR (500 MHz, CDCl₃) δ: 1.31 (3H, t, J=7.0 Hz), 2.53 (3H, s), 2.60 (3H, s), 4.26 (2H, q, J=7.1 Hz), 4.85 (2H, s), 5.35 (2H, s), 6.36 (2H, s), 7.03 (1H, d, J=7.7 Hz), 7.09 (2H, d J=8.3 Hz), 7.15 (1H, t, J=7.6 Hz), 7.28 (1H, t, J=7.4 Hz), 7.34 (1H, d, J=7.7 Hz), 7.35–7.50 (4H, m).

Example 26

Production of 2,4(1H,3H)-dioxo-1-(2-methylthiobenzyl)-6-[4-(1-pyroryl)phenyl]-5-methylthieno[2,3-d]pyrimidine-3-acetic acid (Compound 173).

To a solution of the compound produced in Example 25 (0.10 g, 0.18 mmole) in a mixture of methanol (10 ml) and tetrahydrofuran (10 ml) was added 1N aqueous sodium hydroxide (2 ml) and the solution was stirred at room temperature for 3 hours. The reaction mixture was concentrated and the residue was partitioned between ethy acetate (50 ml) and 1N hydrochloric acid (3 ml). The aqueous layer was extracted with ethyl acetate (30 ml). The combined organic extracts were washed with an aqueous solution of sodium chloride, dried over MgSO₄ and evaporated in vacuo. The resulting residue was chomatographed on silica gel to give a white solid which was recrystallized from ether-ethyl acetate to give pale yellow crystals (0.05 g, 53%).

m.p. 192–197° C.

Elemental analysis (%) for $C_{27}H_{23}N_3O_4S_2 \cdot 1.5 \ H_2O$: Calcd.: C 59.54, H 4.81, N 7.72; Found: C 56.58, H 4.56, N 7.73.

¹H-NMR (500 MHz, CDCl₃) δ: 2.52 (3H, s), 2.55 (3H, s), 4.59 (2H, s), 5.21 (2H, s), 6.28 (2H, s), 7.00 (2H, d, J=7.6 Hz), 7.14 (1H, t, J=7.0 Hz), 7.33 (1H, t, J=7.98 Hz), 7.40 (2H,s), 7.46 (2H, d, J=8.3 Hz), 7.46 (2H, d, J=8.3 Hz).

Example 27

Production of ethyl 2,4(1H,3H)-dioxo-6-(4-butyrylphenyl)-5-methylthieno[2,3-d]pyrimidine-3-acetate (Compound 174).

To a solution of the compound produced in Example 4 (0.39 g, 1.10 mmoles) in nitrobenzene (10 ml) was added aluminum chloride (0.63 g, 4.75 mmoles) with ice-cooling under nitrogen stream. After stirring with ice-cooling for 30 minutes, to the solution was added dropwise butyryl chloride (0.21 ml, 2.20 mmoles). The mixture was stirred at 50° C. for 3 days. The reaction mixture was poured into ice-water and the resulting mixture was partinioned between ethyl acetate and an aqueous solution of sodium chloride. The aqueous layer was extracted with ethyl acetate. The combined organic extracts were washed with an aqueous solution of sodium chloride, dried over MgSO₄ and evaporated in vacuo. The residue was chromatographed on silica gel to give white amorphous powders (0.05 g, 11%).

¹H-NMR (200 MHz, CDCl₃) δ: 1.03 (3H, t, J=7.2 Hz), 1.32 (3H, t, J=7.2 Hz), 1.77 (2H, sext, J=7.2 Hz), 2.54 (3H, s), 2.98 (2H, t, J=7.2 Hz), 4.27 (2H, q, J=7.2 Hz), 4.78 (2H, s), 7.51 (2H, d, J=8.4 Hz), 8.02 (2H, d, J=8.4 Hz), 10.20 (1H, s).

FAB-MS m/z: 415.1 (MH)⁺

Example 28

Production of ethyl 2,4(1H,3H)-dioxo-6-(4-chloromethylphenyl)-5-methylthieno[2,3-d]pyrimidine-3-acetate (Compound 175).

To a solution of the compound produced in Example 4 (1.60 g, 4.65 mmoles) in nitromethane (40 ml) was added aluminum chloride (2.60 g, 19.5 mmoles) with ice-cooling under nitrogen stream. After stirring with ice-cooling for 30 minutes, to the solution was added dropwise methoxyacetyl chloride (0.64 ml, 7.00 mmoles). The mixture was stirred with ice-cooling for one hour and at 50° C. for 24 hours. The reaction mixture was poured into ice-water and the resulting mixture was partitioned between ethyl acetate and an aqueous solution of sodium chloride. The aqueous layer was extracted with ethyl acetate. The combined organic extracts were washed with an aqueous solution of sodium chloride, dried over $MgSO_4$ and evaporated in vacuo. The residue was chromatographed on silica gel to give a white solid (0.74 g, 41%).

m.p. 177–179° C.

$^1$H-NMR (200 MHz, $CDCl_3$) δ: 1.31 (3H, t, J=7.1 Hz), 2.50 (3H, s), 4.26 (2H, q, J=7.1 Hz), 4.63 (2H, s), 4.78 (2H, S), 7.39 (2H, d, J=8.1 Hz), 7.47 (2H, d, J=8.1 Hz), 9.92 (1H, s).

IR (KBr): 3242, 3004, 1738, 1659, 1560, 1526, 1493 $cm^{-1}$.

Example 29

Production of ethyl 2,4(1H,3H)-dioxo-6-(4-ethylthiomethylpheny)-5-methylthieno[2,3-d]pyrimidine-3-acetate (Compound 176).

To a solution of the compound produced in Example 28 (0.30 g; 0.76 mmole) in dimethylformamide (10 ml) were added potassium iodide (0.13 g, 0.76 mmole), ethanthiol (1.00 ml, 11.9 mmoles) and ethyldiisopropylamine (0.16 ml, 0.92 mmole) with ice-cooling. The solution was stirred ice-cooling for 30 minutes and at room temperature for 4 hours. The reaction mixture was concentrated and the residue was partitioned between ethyl acetate and an aqueous solution of ammonium chloride. The aqueous layer was extracted with ethyl acetate. The combined organic extracts were washed with an aqueous solution of sodium chloride, dried over $MgSO_4$ and evaporated in vacuo. The resulting residue was chromatographed on silica gel to give an oily product (0.16 g, 50%).

$^1$H-NMR (200 MHz, DMSO-$d_6$) δ: 1.21–1.29 (6H, m), 2.41–2.52 (5H, m), 3.73 (2H, s), 4.21 (2H, q, J=7.1 Hz), 4.78 (2H, s), 7.29 (2H, q, J=8.5 Hz), 7.35 (2H, d, J=8.5 Hz), 11.18 (1H, s).

FAB-MS m/z: 419.1 (MH)$^+$

Example 30

Production of ethyl 2,4(1H,3H)-dioxo-1-(2-aminobenzyl)-5-methyl-6-(4-methoxyphenyl)thieno[2,3-d]pyrimidine-3-acetate (Compound 177).

To a solution of the Compound 32 produced in Example 7 (0.60 g, 1.18 mmoles) in acetic acid (25 ml) was added iron powder (0.37 g, 5.89 mmoles). The mixture was stirred at 80° C. for 2 hours. After cooling, the reaction mixture was concentrated and the residue was partitioned between ethyl acetate and a saturated aqueous solution of sodium bicarbonate. The aqueous layer was extracted with ethyl acetate. The combined organic extracts were washed with an aqueous solution of sodium chloride, dried over $MgSO_4$ and evaporated in vacuo. The residue was recrystalized from ethyl acetate-hexane to give colorless prisms (0.45 g, 80%).

m.p. 138–140° C.

Elemental analysis (%) for $C_{25}H_{25}N_3O_5S.0.2C_4H_8O_2$: Calcd.: C 62.32, H 5.39, N 8.45 Found: C 62.36, H 5.21, N 8.25.

$^1$H-NMR (200 MHz, $CDCl_3$) δ: 1.31 (3H, t, J=7.1 Hz), 2.47 (3H, s), 3.85 (3H, s), 4.25 (2H, q, J=7.1 Hz), 4.77 (2H, br s), 4.82 (2H, s), 5.16 (2H, s), 6.63–6.73 (2H, m), 6.94–7.36 (6H, m).

IR (KBr): 1754, 1705, 1636, 1562, 1528, 1502 $cm^{-1}$.

FAB-MS m/z: 480 (MH$^+$)

Example 31

Production of ethyl 2,4(1H,3H)-dioxo-1-[2-(N-methylamino)benzyl]-5-methyl-6-(4-methoxyphenyl)thieno[2,3-d]pyrimidine-3-acetate (Compound 178).

To acetic anhydride (1.00 ml, 1.06 mmoles) was added dropwise formic acid (0.50 ml, 13.3 mmoles) with ice-cooling, the mixture was stirred at 55° C. for 2 hours and then allowed to cool to −20° C. the compound produced in Example 30 (0.30 g, 0.62 mmole) was added thereto and the mixture was stirred at −20° C. for 30 minutes. The reaction mixture was concentrated in vacuo to give white powders (0.45 g, 80%). To a solution of these white powders (0.30 g, 0.59 mmole) in tetrahydrofuran (15 ml) was added dropwise dimethylsulfide-boric acid (0.25 ml, 2.50 mmoles) with ice-cooling. The mixture was stirred with ice-cooling for 30 minutes and then refluxed for 2 hours. The reaction mixture was cooled to 0° C. and added methanol (1 ml) thereto and then the mixture was stirred at room temperature for one hour. To this solution was added a solution of hydrogen chloride in methanol (10N, 0.50 ml) and the mixture was refluxed for 30 minutes. The reaction mixture was concentrated and the residure was partitioned between ethyl acetate and a saturated aqueous solution of sodium bicarbonate. The aqueous layer was extracted with ethyl acetate. The combined organic extracts were washed with an aqueous solution of sodium chloride, dried over $MgSO_4$ and evaporated in vacuo. The residue was chromatographed on silica gel to give a curde product which was recrystalized from ethyl acetate-hexane to give white crystals (0.16 g, 55%).

m.p. 188–189° C.

Elemental analysis (%) for $C_{26}H_{27}N_3O_5S$: Calcd.: C 63.27, H 5.51, N 8.51; Found: C 63.20, H 5.69, N 8.63.

$^1$H-NMR (200 MHz, $CDCl_3$) δ: 1.32 (3H, t, J=7.1 Hz), 2.46 (3H, s), 2.82 (3H, s), 3.85 (3H, s), 4.26 (2H, q, J=7.1 Hz), 4.83 (2H, s), 5.15 (2H, s), 6.59–6.69 (2H, m), 6.95 (2H, q, J=8.8 Hz), 7.21–7.36 (4H, m).

IR (KBr): 1742, 1696, 1647, 1607, 1570, 1535 $cm^{-1}$.

FAB-MS m/z: 494 (MH$^+$).

Example 32

Production of ethyl 2,4(1H,3H)-dioxo-5-bromomethyl-1-(2-methoxybenzyl)-6-(4-methoxymethoxypheny)thieno[2,3-d]pyrimidine-3-acetate (Compound 179).

A mixture of the Compound 68 produced in Example 15 (0.69 g, 1.32 mmoles), N-bromosuccinimide (0.234 g, 1.32 mmoles), α,α'-azobisisobutyronitrile (22 mg, 0.13 mmole) and carbontetrachloride (30 ml) was refluxed for 1.5 hours. After cooling, insoluble material was filtered off, the filtrate was diluted with chloroform and washed with an aqueous solution of sodium chloride, dried over $MgSO_4$ and evaporated in vacuo. The resulting residue was recrystalized from ethyl acetate-hexane to give white crystals (0.93 g, 82%).

m.p. 102–105° C.

Elemental analysis (%) for $C_{27}H_{27}N_2O_7SBr.0.2C_4H_8O_2.0.3H_2O$: Calcd.: C 53.29, H 4.69, N 4.47; Found: C 53.13, H 4.43, N 4.19.

$^1$H-NMR (200 MHz, $CDCl_3$) δ: 1.30 (3H, t, J=7.2 Hz), 3.50 (3H, s), 3.88 (3H, s), 4.25 (2H, q, J=7.2 Hz), 4.79 (2H, s), 4.86 (2H, s), 5.22 (2H, s), 5.25 (2H, s), 6.88–7.50 (8H, m).

IR (KBr): 1746, 1707, 1665, 1607, 1528, 1479 cm$^{-1}$.

Example 33

Production of ethyl 2,4(1H,3H)-dioxo-5-acetoxymethyl-1-(2-methoxybenzyl)-6-(4-methoxyphenyl)thieno[2,3-d]pyrimidine-3-acetate (Compound 180).

To a solution of the compound produced in Example 32 (0.30 g, 0.50 mmole) in dimethylformamide (10 ml) were added potassium carbonate (0.10 g, 0.74 mmole) and potassium acetate (0.10 g, 0.99 mmole) and the mixture was stirred at room temperature for 17 hours. The reaction mixture was concentrated and the residue was partitioned between ethyl acetate and a saturated aqueous solution of sodium chloride. The aqueous layer was extracted with ethyl acetate. The combined organic extracts were washed with an aqueous solution of sodium chloride, dried over MgSO$_4$ and evaporated in vacuo. The residue was chromatographed on silica gel to give white amorphous powders (0.24 g, 83%).

$^1$H-NMR (200 MHz, CDCl$_3$) δ: 1.30 (3H, t, J=7.1 Hz), 2.07 (3H, s), 3.49 (3H, s), 3.88 (3H, s), 4.24 (2H, q, J=7.1 Hz), 4.83 (2H, s), 5.20 (2H, s), 5.24 (4H, s), 6.88–7.30 (8H, m).

IR (KBr): 1744, 1711, 1667, 1539, 1483 cm$^{-1}$.

Example 34

Production of ethyl 2,4(1H,3H)-dioxo-6-(4-trifluoromethansulfonyloxyphenyl)-5-methyl-1-(2-methylthiobenzyl)thieno[2,3-d]pyrimidine-3-acetate (Compound 181).

To a solution of the Compound 63 produced in Example 13 (1.00 g, 2.01 mmoles) and ethyldiisopropylamine (0.42 ml, 2.41 mmoles) in dichloromethane (20 ml) was added trifluoromethansulonic anhydride (0.37 ml, 2.21 mmoles) with ice-cooling. The mixture was stirred with ice-cooling for 30 minutes and then at room temperature for 4 hours. The reaction mixture was partitioned between dichloromethane and an aqueous saturated solution of sodium chloride. The aqueous layer was extracted with dichloromethane. The combined organic extracts were washed with an aqueous solution of sodium chloride, dried over MgSO$_4$ and evaporated in vacuo. The residue was chromatographed on silica gel to give white amorphous powders (1.05 g, 83%).

$^1$H-NMR (200 MHz, CDCl$_3$) δ: 1.32 (3H, t, J=7.2 Hz), 2.53 (3H, s), 2.54 (3H, s), 4.26 (2H, q, J=7.2 Hz), 4.85 (2H, s), 5.35 (2H, s), 7.01–7.44 (8H, m).

IR (KBr): 1750, 1711, 1669, 1562, 1528, 1475 cm$^{-1}$.

FAB-MS m/z: 628.9 (MH$^+$)

Example 35

Production of ethyl 2,4(1H,3H)-dioxo-6-(4-biphenyl)-5-metyl-1-(2-methylthiobenzyl)thieno[2,3-d]pyrimidine-3-acetate (Compound 182).

Under argon stream, to a solution of the compound produced in Example 34 (0.40 g, 0.64 mmloe), phenylboric acid (0.08 g, 0.64 mmole) and 2M aqueous solution of sodium carbonate (1.60 ml, 3.20 mmoles) in 1,2-dimethoxyethane (20 ml) was added tetrakis (triphenylphosphine)palladium (0.11 g, 0.10 mmole) and the mixture was refluxed for 4 hours. The reaction mixture was diluted with ethyl acetate and an insoluble material was filtered off. The filtrate was partitioned between ethyl acetate and a saturated aqueous solution of sodium chloride. The aqueous layer was extracted with ethyl acetate. The combined organic extracts were washed with an aqueous solution of sodium chloride, dried over MgSO$_4$ and evaporated in vacuo. The residue was chromatographed on silica gel to give a curde product which was recrystalized from ethyl acetate-hexane to give white crystals (0.24 g, 67%).

m.p. 159–160° C.

Elemental analysis (%) for C$_{31}$H$_{28}$N$_2$O$_4$S$_2$.0.5C$_4$H$_8$O$_2$.0.35CHCl$_3$: Calcd.: C 62.34, H 5.07, N 4.35; Found: C 62.34, H 4.88, N 4.17.

$^1$H-NMR (200 MHz, CDCl$_3$) δ: 1.32 (3H, t, J=7.2 Hz), 2.55 (3H, s), 2.59 (3H, s), 4.27 (2H, q, J=7.2 Hz), 4.87 (2H, s), 5.37 (2H, s), 7.03–7.64 (13H, m).

IR (KBr): 1742, 1709, 1661, 1533, 1475, 1446 cm$^{-1}$.

FAB-MS m/z: 557.2 (MH$^+$).

Example 36

Production of ethyl 2,4(1H,3H)-dioxo-5-methyl-1-(2-methylthiobenzyl)-6-(4-methoxyethylphenyl)thieno[2,3-d]pyrimidine-3-acetate (Compound 183).

Under argon stream, to a solution of the compound produced in Reference Example 13 (0.40 g, 0.83 mmloe), 4-methoxyphenylboric acid (0.22 g, 1.24 mmoles) and 2M aqueous solution of sodium carbonate (2.10 ml, 4.20 mmoles) in 1,2-dimethoxyethane (20 ml) was added tetrakis (triphenylphosphine)palladium (0.14 g, 0.13 mmole) and the mixture was refluxed for 5 hours. The reaction mixture was diluted with ethyl acetate and an insoluble material was filtered off. The filtrate was partitioned between ethyl acetate and a saturated aqueous solution of sodium chloride. The aqueous layer was extracted with ethyl acetate. The combined organic extracts were washed with an aqueous solution of sodium chloride, dried over MgSO$_4$ and evaporated in vacuo. The residue was chromatographed on silica gel to give a curde product which was recrystalized from ethyl acetate-hexane to give white crystals (0.19 g, 43%).

m.p. 126–128° C.

Elemental analysis (%) for C$_{28}$H$_{30}$N$_2$O$_5$S$_2$: Calcd.: C 62.43, H 5.61, N 5.20; Found: C 62.32, H 5.39, N 5.09.

$^1$H-NMR (200 MHz, CDCl$_3$) δ: 1.30 (3H, t, J=7.2 Hz), 2.51 (3H, s), 2.54 (3H, s), 2.89 (2H, t, J=6.9 Hz), 3.35 (3H, s), 3.61 (2H, t, J=6.9 Hz), 4.26 (2H, q, J=7.2 Hz), 4.86 (2H, s), 5.34 (2H, s), 7.05–7.40 (8H, m).

IR (KBr): 1754, 1709, 1663, 1477 cm$^{-1}$.

FAB-MS m/z: 539.2 (MH$^+$).

Example 37

Production of ethyl 2,4(1H,3H)-dioxo-6-thienyl-5-methyl-1-(2-methylthiobenzyl)thieno[2,3-d]pyrimidine-3-acetate (Compound 184).

3-Thiopeneboric acid (0.32 g, 1.24 mmoles) was used instead of 4-methoxyphenylboric acid and the same operations as mentioned in Example 36 were carried out by using the compound produced in Reference Example 13 (0.40 g, 0.83 mmoles), 2M aqueous solution of sodium carbonate (2.1 ml, 4.2 mmoles), dimethoxyethane (20 ml) and tetraxis (triphenylphoshine)palladium (0.20 g, 0.17 mmole) to give Compound 184 (yield: 45%).

m.p. 119–121° C.

$^1$H-NMR (200 MHz, CDCl$_3$) δ: 1.31 (3H, t, J=7.1 Hz), 2.54 (3H, s), 2.57 (3H, s), 4.25 (2H, q, J=7.1 Hz), 4.85 (2H, s), 5.34 (2H, s), 7.00–7.35 (2H, m).

IR (KBr): 1709, 1665, 1541, 1477 cm$^{-1}$.

FAB-MS m/z: 494 (MH$^+$)

Example 38

Production of ethyl 2,4(1H,3H)-dioxo-6-[4-(3-thienyl)phenyl]-5-methyl-1-(2-methylthiobenzyl)thieno[2,3-d]pyrimidine-3-acetate (Compound 185).

3-Thiopeneboric acid (0.14 g, 1.09 mmoles) was used instead of phenylboric acid and the same operations as mentioned in Example 35 were carried out by using the compound produced in Example 34 (0.33 g, 0.53 mmoles), 2M aqueous solution of sodium carbonate (1.3 ml, 2.6 mmoles), dimethoxyethane (15 ml) and tetrakis(triphenylphoshine)palladium (0.11 g, 0.10 mmole) to give Compound 185 (yield: 50%).

m.p. 166–168° C.

Elemental analysis (%) for $C_{29}H_{26}N_2O_4S_3.0.5H_2O$: Calcd.: C 61.47, H 4.79, N 4.89; Found: C 61.82, H 4.81, N 4.60.

$^1$H-NMR (200 MHz, $CDCl_3$) δ: 1.31 (3H, t, J=7.1 Hz), 2.54 (3H, s), 2.57 (3H, s), 4.26 (2H, q, J=7.1 Hz), 4.86 (2H, s), 5.36 (2H, s), 7.01–7.64 (11H, m).

IR (KBr): 1736, 1707, 1665, 1475 $cm^{-1}$.

Example 39.

Production of ethyl 2,4(1H,3H)-dioxo-5-methyl-1-(2-methylthiobenzyl)-6-(4-propyonylaminophenyl)thieno[2,3-d]pyrimidine-3-acetate (Compound 180).

To a solution of the compound produced in Example 24 (0.30 g, 0.61 mmole) in dichloromethane (10 ml) was added triethylamine (0.10 g, 0.73 mmole) and then added N,N-dimethylaminopyridine (15 mg, 0.12 mmole) and propionyl lchloride (0.11 ml, 1.22 mmoles). The mixture was stirred at room temperature for one hour. The reaction mixture was partitioned between aq. sat. $NH_4Cl$ solution water and dichloromethane. The aqueous layer was extracted with dichloromethane. The combined organic extracts were washed with an aqueous solution of sodium chloride, dried over $MgSO_4$ and evaporated in vacuo. The residue was chromatographed on silica gel to give colorless crystals (0.25 g, 74%).

m.p. 218–219

Elemental analysis (%) for $C_{26}H_{25}N_3O_5S_2.0.5H_2O$: Calcd.: C 58.63, H 4.92, N 7.89; Found: C 58.71, H 4.90, N 7.79.

$^1$H-NMR (200 MHz, $CDCl_3$) δ: 1.22–1.34 (6H, m), 2.41 (2H, q, J=7.5 Hz), 2.51 (3H, s), 2.53 (3H, s), 4.26 (2H, q, J=7.1 Hz), 4.85 (2H, s), 5.32 (2H, s), 7.00–7.56 (8H, m).

IR (KBr): 1707, 1661, 1537, 1479 $cm^{-1}$.

Example 40

Production of 2,4(1H,3H)-dioxo-6-thienyl-5-methyl-1-(2-methylthiobenzyl)thieno[2,3-d]pyrimidine-3-acetic acid (Compound 187).

The same operations as mentioned in Example 22 were carried out by using the compound produced in Example 37 (0.10 g, 0.21 mmole), 1N aqueous solution of sodium hydroxide (1.03 ml, 1.03 mmoles), tetrahydrofuran (3 ml) and ethanol (3 ml) to give Compound 187 (yield: 59%).

m.p. 255–257° C.

Elemental analysis (%) for $C_{21}H_{18}N_2O_4S_3$: Calcd.: C 55.00, H 3.96, N 6.11; Found: C 54.78, H 3.87, N 6.14.

$^1$H-NMR (200 MHz, $CDCl_3$) δ: 2.53 (3H, s), 2.58 (3H, s), 4.64 (2H, s), 6.98 (1H, d, J=7.5 Hz), 7.15 (1H, t, J=7.5 HZ), 7.23–7.45 (3H, m), 7.67–7.71 (2H, m).

IR (KBr): 1696, 1659, 1635, 1477 $cm^{-1}$.

Example 41

A tablets was prepared by a conventional method using 100 mg of the compound 131 produced in Example 23, 165 mg of lactose, 25 mg of corn starch, 4 mg of polyvinyl alcohol and 1 mg of magnesium stearate.

Example 42

The compound 131 (5 g) produced in Example 23 was dissolved in a distilled water for injection to make the total volume 100 ml. The solution was subjected to an aseptic filtration using a membrane filter of 0.22 micrometer (manufactured by Sumitomo Electric, Japan or by Saltorius, Germany). Each 2 ml of the filtrate was placed in a washed and sterilized vial and dried by freezing by a conventional method to prepare a freeze-dried injection of 100 mg/vial.

Example 43

A tablet was prepared by a conventional method using 100 mg of the compound 115 produced in Example 23, 165 mg of lactose, 25 mg of corn starch, 4 mg of polyvinyl alcohol and 1 mg of magnesium stearate.

Example 44

The compound 115 (5 g) produced in Example 23 was dissolved in a distilled water for injection to make the total volume 100 ml. The solution was subjected to an aseptic filtration using a membrane filter of 0.22 micrometer (manufactured by Sumitomo Electric, Japan or by Saltorius, Germany). Each 2 ml of the filtrate was placed in a washed and sterilized vial and dried by freezing by a conventional method to prepare a freeze-dried injection of 100 mg/vial.

Example 45

A tablet was prepared by a conventional method using 100 mg of the compound 144 produced in Example 23, 165 mg of lactose, 25 mg of corn starch, 4 mg of polyvinyl alcohol and 1 mg of magnesium stearate.

Example 46

The compound 144 (5 g) produced in Example 23 was dissolved in a distilled water for injection to make the total volume 100 ml. The solution was subjected to an aseptic filtration using a membrane filter of 0.22 micrometer (manufactured by Sumitomo Electric, Japan or by Saltorius, Germany). Each 2 ml of the filtrate was placed in a washed and sterilized vial and dried by freezing to prepare a freeze-dried injection of 100 mg/vial.

Example 47

A tablet was prepared by a conventional method using 100 mg of the compound 145 produced in Example 23, 165 mg of lactose, 25 mg of corn starch, 4 mg of polyvinyl alcohol and 1 mg of magnesium stearate.

Example 48

The compound 145 (5 g) produced in Example 23 was dissolved in a distilled water for injection to make the total volume 100 ml. The solution was subjected to an aseptic filtration using a membrane filter of 0.22 micrometer (manufactured by Sumitomo Electric, Japan or by Saltorius, Germany). Each 2 ml of the filtrate was placed in a washed and sterilized vial and dried by freezing by a conventional method to prepare a freeze-dried injection of 100 mg/vial.

Test Example 1

Endothelin Receptor Assay:

A pig ventricular muscle membrane fraction for an endothelin-A receptor assay and a bovine cerebral membrane fraction for an endothelin-B receptor assay were diluted with an assay buffer [comprising 20 mM of Tris-HCl, 2 mM of EGTA (ethylene glycol bis(2-aminoethyl ether) tetraacetic acid), 5 mM of magnesium acetate, 0.1% of BSA (bovine serum albumin), 0.03% of NaN$_3$, 0.5 mM of PMSF (phenylmethylsulfonyl fluoride), 20 micrograms/ml of leupeptin, 4 micrograms/ml of E-64 (manufactured by the Peptide Institute, Japan) and 1 microgram/ml of pepstatin; pH 7.2] to 12 µg/ml and 180 µg/ml, respectively.

To each 100 microliter of them was added 5 nM [$^{125}$I] endothelin-1 (2 microliters). A solution (3 microliters) of the sample was added and the mixture was incubated at 25° C. for 60 minutes. In order to measure the maximum binding (B$_0$) and the nonspecific bonding (NSB), a lot to which dimethyl sulfoxide (3 microliters) or a solution (3 microliters) of 10–5M of endothelin in dimethyl sulfoxide was added was incubated as well. An assay buffer supplemented with 0.05% CHAPS (3-[(3-cholamidopropyl)dimethylammonio]-1-propanesulfonate, 1.5 ml) was added thereto and the mixture was filtered through a GF/F glass fiber filter (a trade name of Whatman, England) and further washed with 1.5 ml of the same buffer. The radioactivity of the filter was counted by a γ-counter and a calculation was conducted in accordance with the following formula (1) whereby a percent maximum binding (hereinafter, referred to as PMB) was determined. In addition, the concentration wherein the PMB was 50% (IC$_{50}$) was calculated as well. The IC$_{50}$ values for the compounds of the present invention are shown in the following Table 13.

$$PMB=[(B-NSB)/(B_0-NSB)]\times 100 \qquad (1)$$

TABLE 13

| Compound Number | IC$_{50}$ (micromoles) | |
|---|---|---|
| | Endothelin-A Receptor (pigs) | Endothelin-B Receptor (bovine) |
| Compd. No. 102 | 1.3 | 7.5 |
| Compd. No. 99 | 12 | 39 |

Test Example 2

Endothelin Assay Test:

Endothelin (ET) receptors were prepared as follows. An insect cell (Sf9) membrane fraction wherein human endothelin-A (ETA) was expressed and that wherein endothelin-B (ETB) was expressed were diluted with an assay buffer [comprising 20 mM of Tris-HCl, 2 mM of EGTA (ethylene glycol bis(2-aminoethyl ether)tetraacetic acid), 5 mM of magnesium acetate, 0.1% of BSA (bovine serum albumin), 0.03% of NaN$_3$, 0.5 mM of PMSF (phenylmethylsulfonyl fluoride), 20 micrograms/ml of leupeptin, 4 micrograms/ml of E-64 (manufactured by the Peptide Institute, Japan) and 1 microgram/ml of pepstatin; pH 7.2] to make 1.4 micrograms/ml and 0.7 microgram/ml for the insect cell (Sf 9) membrane fraction wherein a human ETA receptor was expressed and for that wherein a human ETB receptor was expressed, respectively. Each 100 microliters of them were taken out and 2 microliters of 5 nM [$^{125}$I]endothelin-1 was added thereto. A dimethyl sulfoxide solution (3 microliters) of the sample was added thereto and the mixture was incubated at 25° C. for 60 minutes. Further, in order to measure the maximum binding (B$_0$) and the nonspecific binding (NSB), a lot to which 3 ml of dimethyl sulfoxide or 3 ml solution of 10–5M of endothelin-1 in dimethyl sulfoxide was added was incubated as well. An assay buffer suspended with 0.05% CHAPS (3-[(3-cholamidopropyl)di-methylammonio]-1-propanesulfonate, 1.5 ml) was added and the mixture was filtered through a GF/F glass fiber filter (trade name of Whatman, England) followed by washing with 1.5 ml of the same buffer.

The radioactivity of the filter was counted by a γ-counter and determined PMB by the same way described in Test Example 1. The value wherein PMB=50% was calculated and expressed as an IC$_{50}$. The IC$_{50}$ values of the compounds of the present invention are shown in the following Table 14.

TABLE 14

| Compound Number | IC$_{50}$ (micromoles) | |
|---|---|---|
| | Endothelin-A Receptor (human) | Endothelin-B Receptor (human) |
| 105 | 1.9 | 12 |
| 111 | 1.8 | 14 |
| 115 | 0.71 | 6.8 |
| 125 | 2.9 | 26 |
| 130 | 1.2 | 12 |
| 131 | 0.30 | 2.4 |
| 140 | 0.24 | 15 |
| 143 | 2.5 | 33 |
| 144 | 0.085 | 0.92 |
| 145 | 0.066 | 0.66 |
| 146 | 0.25 | 2.6 |
| 148 | 0.40 | 7.1 |
| 156 | 2.6 | 16 |
| 173 | 2.1 | 2.5 |

(Effect of the Invention)

The pharmaceutical composition for antagonizing endothelin containing the thienopyrimidine derivatives of the present invention can be advantageously used for preventing or treating acute rental insufficiency, myocardial infarction, liver insufficiency, angina pectoris, cerebral infarction, subarachnoid heamorrhage (SAH), hypertension, renal insufficiency, asthma, variant form of angina, Raynaud's syndrome, pulmonary hypertension, surgery shock, chronic cardiac insufficiency, cardiac hypertrophy, arteriosclerosis, migraine and the like, furthermore, for treating or preventing a hypofunction of an organ caused by its surgery or transplant insufficient microcirculation, still furthermore, for preventing restenosis after PTCA.

The substituent designations of the formulae of the second embodiment are specific to the first embodiment and may be the same or different than the substituent designations according to the first embodiment.

Technical Field of the Second Embodiment

The second embodiment of the present invention relates to thienopyrimidine derivatives and salts thereof. The second embodiment of the present invention further relates to methods for manufacturing the thienopyrimidine derivatives and the salts thereof, and pharmaceutical compositions containing the thienopyrimidine derivatives.

Background Art of the Second Embodiment

The possibility has been suggested that, among adult diseases which are being encountered with increasing frequencies in these years, ischemia-associated-diseases such as cerebral infarction, angina pectoris, myocardial infarction, renal failure and hepatic disorder are mediated by endothelin. Endothelin is a peptide of 21 amino acid residues as produced and released from endothelial cells and endothelin-1, endothelin-2 and endothelin-3 have so far been identified. Throughout this specification, these endothelin species are collectively referred to as "endothelin".

Endothelin reportedly is a substance having the most potent and lasting vasoconstrictive, pressor and heart muscle contractility-increasing actions of all the physiological substances and synthetic substances so far known. It is suspected that these actions of this particular peptide are manifested through the endothelin receptors suspected to exist in the vascular smooth muscle fascia and elsewhere. As the endothelin receptors, endothelin-A and endothelin-B receptors (both are collectively referred to as endothelin receptors) are already known.

Therefore, any compound having an affinity for the endothelin receptors and showing endothelin antagonizing activity is likely to be effective in the prevention and treatment of ischemia-associated diseases (for example, cerebral infarction, angina pectoris, myocardial infarction, renal failure, and hepatic disorder) and the development of a drug of this type has been awaited in earnest. As synthetic compounds having endothelin receptor antagonist activity, the compounds described typically in EP-A-510526, EP-A-526708, PCT.WO-9308799, and Journal of Medicinal Chemistry, 37, 1553–1557, 1994 are known.

Recently, it has been pointed out that a thienopyrimidine derivative has endothelin receptor antagonist activity (European Patent Publication No. 640,606).

During the study of thienopyrimidine compounds, the present inventors have found that a thienopyrimidine compound which has a carboxyl group and a group capable of forming an anion in the molecule has particularly potent endothelin receptor antagonist activity. The inventors did further research on the basis of the above finding and have completed the present invention.

Disclosure of Invention of the Second Embodiment

The present invention provides:

(1) A thieno[2,3-d]pyrimidine derivative, i.e. compound (I), wherein it has (i) a carboxyl group or an ester thereof and (ii) a group other than a carboxyl group which is capable of forming an anion or a group convertible thereinto in its molecule;

(2) A compound according to the item (1), wherein the group other than a carboxyl group which is capable of forming an anion or a group convertible thereinto is tetrazolyl, an optionally substituted sulfonamido group, a phosphono group or a sulfo group, each of which may optionally be substituted by alkyl or acyl;

(3) A compound (I') of the formula:

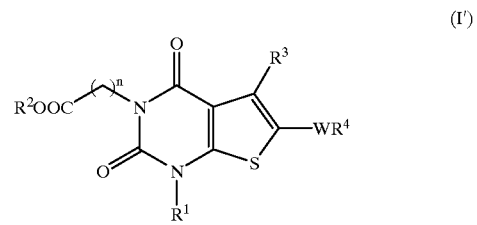

wherein each of $R^1$ and $R^2$ are hydrogen or an optionally substituted hydrocarbon residue, $R^3$ is a $C_{1-6}$ alkyl group which is substituted by a $C_{1-6}$ alkoxy-carbonyl group or a group of the formula: —NH—$SO_2$—$R^5$ wherein $R^5$ is (1) a $C_{1-6}$ alkyl group which may optionally be substituted by halogen or (2) a $C_{6-14}$ aryl group, $R^4$ is an optionally substituted hydrocarbon residue or an optionally substituted heterocyclic group, W denotes a chemical bond or a spacer group and n denotes an integer of 1 to 3, or a salt thereof;

(4) A compound according to the item (3), wherein $R^1$ is an optionally substituted $C_{1-20}$ hydrocarbon residue;

(5) A compound according to the item (4), wherein the $C_{1-20}$ hydrocarbon residue is a $C_{1-10}$ alkyl, $C_{3-10}$ cycloalkyl, $C_{2-10}$ alkenyl, $C_{6-14}$ aryl or $C_{7-20}$ aralkyl group;

(6) A compound according to the item (4), wherein $R^1$ is an optionally substituted $C_{7-20}$ aralkyl group;

(7) A compound according to the item (3), wherein $R^1$ is a hydrocarbon residue optionally substituted with (1) halogen, (2) nitro, (3) cyano, (4) an optionally substituted hydroxyl group, (5) a group of the formula: —S(O)f—$R^6$, wherein f denotes an integer of 0 to 2, and $R^6$ is a hydrogen atom or an optionally substituted hydrocarbon residue, (6) an optionally substituted amino group or (7) an optionally substituted 5- or 6-membered heterocyclic group which contains 1 to 4 heteroatom(s) of oxygen, sulfur or nitrogen;

(8) A compound according to the item (3), wherein $R^1$ is a hydrocarbon residue optionally substituted with halogen or a $C_{1-4}$ alkylthio group;

(9) A compound according to the item (3), wherein $R^2$ is an optionally substituted $C_{1-20}$ hydrocarbon residue;

(10) A compound according to the item (9), wherein $R^2$ is an optionally substituted $C_{1-10}$ alkyl, $C_{3-10}$ cycloalkyl, $C_{2-10}$ alkenyl, $C_{6-14}$ aryl or $C_{7-20}$ aralkyl group;

(11) A compound according to the item (3), wherein $R^2$ is an optionally substituted $C_{1-10}$ alkyl;

(12) A compound according to the item (3), wherein $R^2$ is a hydrocarbon residue optionally substituted with (1) halogen, (2) nitro, (3) cyano, (4) an optionally substituted hydroxyl group, (5) a group of the formula: —S(O)f—$R^6$, wherein f denotes an integer of 0 to 2, and $R^6$ is a hydrogen atom or an optionally substituted hydrocarbon residue, (6) an optionally substituted amino group or (7) an optionally substituted 5- or 6-membered heterocyclic group which contains 1 to 4 heteroatom(s) of oxygen, sulfur or nitrogen;

(13) A compound according to the item (3), wherein $R^2$ is a hydrocarbon residue optionally substituted with (1) halogen, (2) nitro, (3) hydroxyl, (4) cyano, (5) $C_{1-4}$ alkylthio, (6) $C_{1-4}$ alkoxy, (7) $C_{1-6}$ alkylcarbonyloxy or (8) $C_{3-6}$ cycloalkyl-oxycarbonyloxy;

(14) A compound according to the item (3), wherein $R^2$ is hydrogen or a $C_{1-6}$ alkyl group which may optionally be substituted by $C_{1-6}$ alkyl-carbonyloxy or $C_{3-6}$ cycloalkyl-oxycarbonyloxy;

(15) A compound according to the item (3), wherein $R^3$ is a $C_{1-6}$ alkyl group which is substituted by a $C_{1-6}$ alkoxy-carbonyl group or a group of the formula: —NH—$SO_2$—$R^{5'}$, wherein $R^{5'}$ is a $C_{1-6}$ alkyl group or a $C_{6-14}$ aryl group;

(16) A compound according to the item (3), wherein $R^3$ is a $C_{1-6}$ alkyl group which is substituted by a group of the formula: —NH—SO$_2$—R$^5$, wherein $R^5$ is (1) a $C_{1-6}$ alkyl group which may optionally be substituted by halogen or (2) a $C_{6-14}$ aryl group;

(17) A compound according to the item (3), wherein $R^3$ is a $C_{1-6}$ alkyl group which is substituted by a group of the formula: —NH—SO$_2$—R$^{5'}$, wherein $R^{5'}$ is a $C_{1-6}$ alkyl group or a $C_{6-14}$ aryl group;

(18) A compound according to the item (3), wherein $R^4$ is optionally substituted $C_{1-20}$ hydrocarbon residue or an optionally substituted 5- to 13-membered heterocyclic group which contains 1 to 4 heteroatom(s) of oxygen, sulfur or nitrogen;

(19) A compound according to the item (3), wherein $R^4$ is an optionally substituted $C_{6-14}$ aryl group;

(20) A compound according to the item (3), wherein $R^4$ is a hydrocarbon residue optionally substituted with (1) halogen, (2) nitro, (3) cyano, (4) $C_{1-6}$ alkoxy which may optionally be substituted by $C_{1-6}$ alkoxy, carboxyl, halogen, $C_{1-6}$ alkyl-carbamoyl or 5 to 7 membered nitrogen-containing heterocyclic group-carbonyl, (5) $C_{7-13}$ aralkyloxy, (6) $C_{1-4}$ alkyl which may be substituted by $C_{1-3}$ alkoxy, (7) $C_{1-6}$ alkanoyl, (8) $C_{1-4}$ alkylthio, (9) $C_{2-6}$ alkenyloxy, (10) $C_{1-6}$ alkoxy-carbonyl or (11) $C_{1-6}$ alkyl-carbamoyl;

(21) A compound according to the item (3), wherein the $R^4$ is a hydrocarbon residue optionally substituted with $C_{1-6}$ alkoxy which may optionally be substituted by $C_{1-6}$ alkoxy, carboxyl, halogen, $C_{1-6}$ alkyl-carbamoyl, a 5 to 7 membered nitrogen-containing heterocyclic group-carbonyl;

(22) A compound according to the item (3), wherein W is a spacer group selected from the group consisting of (1) $C_{1-4}$ alkylene, (2) $C_{2-6}$ alkenylene, (3) a group of the formula —(CH$_2$)cNR$^7$—, where c represents an integer of 0–3, $R^7$ represents hydrogen or $C_{1-6}$ alkyl, (4) —CO—, (5) a group of the formula —CONR$^7$—, where R is as defined above, (6) —O—, (7) a group of the formula: —S(O)f—, where f represents an integer of 0 to 2, and (8) a group of the formula: —NR$^7$S(O)e—, where e represents an integer of 0–2; $R^7$ is as defined above;

(23) A compound according to the item (3), wherein W is a chemical bond;

(24) A compound according to the item (3), wherein $R^1$ is benzyl group which may optionally be substituted by (1) halogen or (2) $C_{1-4}$ alkylthio, $R^2$ is a hydrogen atom or a $C_{1-4}$ alkyl group which may optionally be substituted by (1) $C_{1-6}$ alkyl-carbonyloxy or (2) $C_{3-6}$ cycloalkyl-oxycarbonyloxy, $R^3$ is a $C_{1-6}$ alkyl group which is substituted by (1) a $C_{1-6}$ alkoxy-carbonyl group or (2) a group of the formula: —NH—SO$_2$—R$^{5''}$ (wherein $R^{5''}$ is (1) a $C_{1-3}$ alkyl group which may optionally be substituted by halogen or (2) a phenyl group, W is a chemical bond, $R^4$ is a phenyl group which is substituted by (1) $C_{1-4}$ alkoxy, which may be substituted by $C_{1-6}$ alkoxy, carboxyl, $C_{1-6}$ alkyl-carbamoyl, piperazinecarbonyl or halogen, (2) $C_{7-8}$ aralkyloxy, (3) $C_{1-4}$ alkyl which may be substituted by $C_{1-3}$ alkoxy, (4) $C_{1-6}$ alkanoyl, (5) $C_{2-4}$ alkenyloxy, (6) $C_{1-6}$ alkoxy-carbonyl or (7) $C_{1-6}$ alkyl carbamoyl;

(25) 2,4(1H,3H)-dioxo-6-(4-methoxymethoxyphenyl)-1-(2-methylthiobenzyl)-5-(methanesulfonamidomethyl)-thieno[2,3-d]pyrimidine-3-acetic acid or its salt;

(26) 2,4(1H,3H)-dioxo-6-(4-methoxymethoxyphenyl)-1-(2-methylthiobenzyl)-5-(ethanesulfonamidomethyl)-thieno[2,3-d]pyrimidine-3-acetic acid or its salt;

(27) 2,4(1H,3H)-dioxo-6-(4-methoxyphenyl)-1-(2-methylthiobenzyl)-5-(methanesulfonamidomethyl)-thieno[2,3-d]pyrimidine-3-acetic acid or its salt;

(28) Ethyl 2,4(1H,3H)-dioxo-6-(4-methoxyphenyl)-1-(2-methylthiobenzyl)-5-(carboxymethyl)thieno[2,3-d]pyrimidine-3-acetate;

(29) A method for producing a compound as defined in the item (3), which comprises subjecting a compound (II) of the formula:

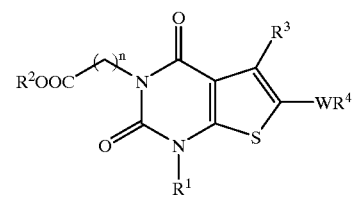

wherein, $R^1$, $R^2$, W and $R^4$ have the same meaning as defined in the item (3) and $R^3$ is a $C_{1-6}$ alkyl group which is halogenated or cyanated, to (1) a nucleophilic substitution reaction with a sulfonamide compound when the alkyl of $R^{3'}$ is halogenated or (2) alkalihydrolysis and then esterification when the alkyl of $R^{3'}$ is cyanated;

(30) A pharmaceutical composition, which comprises a compound as defined in the item (1), (3) or (28) and a carrier, excipient or diluent therefor;

(31) A pharmaceutical composition according to the item (30), which is a therapeutic drug for treating vasoconstriction in a mammal;

(32) A pharmaceutical composition according to the item (31), wherein the vasoconstriction is in a coronary artery, coronary vein, cerebrovascular system or pulmonary vascular system; and

(33) A pharmaceutical composition according to the item (30), which is for antagonizing endothelin activity;

(34) A pharmaceutical composition according to the item (33), which is a therapeutic drug for acute renal insufficiency, cardiac infarction or liver insufficiency;

(35) A pharmaceutical composition according to the item (33), which is a treapeutic drug for hypofunction of an organ caused by a surgery or transplant;

(36) A pharmaceutical composition according to the item (35), wherein the organ is liver;

(37) A method for treating a mammal suffering from vasoconstriction, which comprises administering an effective amount of a compound as defined in the item (1), (3) or (28) to the mammal; and

(38) A method for treating a mammal suffering from acute renal insufficiency, cardiac infarction or liver insufficiency, which comprises administering an effective amount of a compound as defined in the item (1), (3) or (28) to the mammal.

(39) Use of a compound as defined in item (1), (3) or (28) for producing a pharmaceutical composition for the manufacture of a medicament for therapeutic application on vasoconstriction.

(40) Use of a compound as defined in item (1), (3) or (28) for producing a pharmaceutical composition for the manufacture of a medicament for therapeutic application on acute renal insufficiency, cardiac infarction or liver insufficiency.

The nucleus of the present compound, 2,4(1H,3H)-dioxo-thieno[2,3-d]pyrimidine, is shown below:

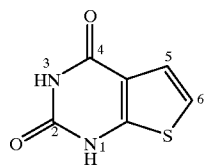

The esterified carboxyl group in the thienopyrimidine derivatives includes a group represented by the formula: —CO—D, wherein D denotes (1) hydroxyl group, (2) a group of the formula: —O—$R^8$, wherein $R^8$ is an optionally substituted hydrocarbon residue or an optionally substituted amino group.

The group which is capable of forming an anion or a group convertible thereinto except carboxyl group includes tetrazolyl, an optionally substituted sulfonamide group, e.g. a group of the formula: —NH—$SO_2$—$R^5$ wherein $R^5$ is (1) a $C_{1-6}$ alkyl group which may optionally be substituted by halogen or (2) a $C_{6-14}$ aryl group, phosphono group and sulfo group, each of which may optionally be substituted by one or 2 of $C_{1-6}$ alkyl or acyl, e.g. $C_{2-5}$ alkanoyl, e.g. acetyl, propionyl, butyryl, valeryl, or $C_{6-14}$ arylcarbonyl, e.g. benzoyl.

As preferred example of the compound (I), mention is made of a compound (I') of the formula:

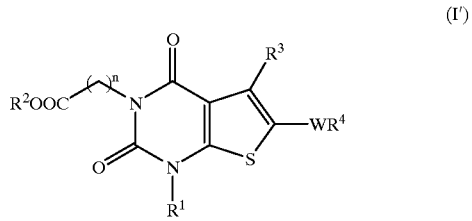

(I')

wherein each of $R^1$ and $R^2$ are hydrogen or an optionally substituted hydrocarbon residue, $R^3$ is a $C_{1-6}$ alkyl group which is substituted by a $C_{1-6}$ alkoxy-carbonyl group or a group of the formula: —NH—$SO_2$—$R^5$ wherein $R^5$ is (1) a $C_{1-6}$ alkyl group which may optionally be substituted by halogen or (2) a $C_{6-14}$ aryl group, $R^4$ is an optionally substituted hydrocarbon residue or an optionally substituted heterocyclic group, W denotes a chemical bond or a spacer group and n denotes an integer of 1 to 3, or a salt thereof.

The hydrocarbon residue in the optionally substituted hydrocarbon residue for the group $R^8$ in the group D, the group $R^{1,}$ the group $R^2$, the group $R^4$ in the formula (I') and the group $R^6$ mentioned below includes a hydrocarbon residue having one to 20 carbon atoms. As examples of the $C_{1-20}$ hydrocarbon residue, mention is made of $C_{1-10}$ alkyl, e.g. methyl, ethyl, propyl, isopropyl, n-butyl, isobutyl, t-butyl, pentyl, hexyl, heptyl, octyl, nonyl, decyl, etc, and among others, $C_{1-6}$ alkyl is preferable, $C_{3-10}$ cycloalkyl, e.g. cyclopropyl, cyclobutyl, cyclopentyl, cyclohexyl, cycloheptyl, cyclooctyl, cyclononyl, etc, and among others, $C_{3-6}$ cycloalkyl is preferable, $C_{7-10}$ bicycloalkyl, e.g. bicyclo[2,2,1]heptyl, bicyclo[2,2,2]octyl, bicyclo[3,2,1]octyl, bicyclo[3,3,1]nonyl, bicyclo[4,2,1]nonyl and bicyclo[4,3,1]decyl, etc, $C_{2-10}$ alkenyl, e.g. vinyl, allyl, isopropenyl, 1-butenyl, 2-butenyl, butadienyl, hexatrienyl, etc, and among others, $C_{2-6}$ alkenyl is preferable, $C_{6-14}$ aryl e.g. phenyl, naphthyl, anthryl, phenanthryl, acenaphthyl, anthracenyl, etc., among others, phenyl, 1-naphthyl, 2-naphthyl are preferable, and $C_{7-20}$ aralkyl, e.g. benzyl, phenethyl, benzhydryl, trityl, etc, and among others, $C_{7-8}$ aralkyl, e.g. benzyl and phenethyl are preferable.

The substituent which said hydrocarbon residue may optionally have includes but is not limited to (1) halogen, e.g. fluorine, chlorine, bromine, iodine, (2) nitro, (3) nitroso, (4) cyano, (5) hydroxyl group which may optionally be substituted by (i) $C_{1-6}$ alkyl, which may optionally be substituted by hydroxyl, $C_{1-6}$ alkoxy, $C_{1-3}$ alkoxy-$C_{1-3}$ alkoxy, $C_{1-3}$ alkylthio, oxy-$C_{1-3}$ alkoxy, carboxyl, carbamoyl, $C_{1-6}$ alkyl-carbamoyl, 5 to 7 membered nitrogen containing heterocyclic group—carbonyl or halogen, (ii) $C_{1-6}$ acyl, (iii) $C_{7-20}$ aralkyl, which may optionally be substituted by halogen, $C_{1-3}$ alkoxy or $C_{1-4}$ alkyl, (iv) $C_{6-14}$ aryl, which may optionally be substituted by halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkyl-amino, (ix) $C_{1-3}$ alkoxy-carbonyl, (x) $C_{1-6}$ alkyl-carbonyl, (xi) $C_{3-6}$ cycloalkyloxycarbonyl or (xii) trifluorosulfonyl, (6) a group of the formula: —S(O)f—$R^6$, wherein f is an integer of 0 to 2, $R^6$ represents a hydrogen atom or a hydrocarbon residue which may optionally be substituted, the hydrocarbon residue has the same meaning as defined above, among others, $C_{1-6}$ alkyl, $C_{6-14}$ aryl, $C_{7-20}$ aralkyl are preferable, and as examples of the substituent to the hydrocarbon residue, mention is made of halogen, nitro, cyano, hydroxy, oxo, thioxo, carboxyl, cyano-$C_{6-14}$ aryl, halogeno-$C_{6-14}$ aryl, etc, (7) an optionally substituted amino group, which is represented by the formula: —$NR^9R^{10}$, wherein each of $R^9$ and $R^{10}$ are hydrogen, hydrocarbon residue, which has the same meaning as defined above, $C_{1-6}$ acyl or a 5 to 13 membered heterocyclic group which is mentioned below, (8) an optionally substituted carboxyl group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) an optionally substituted amino group which is defined above or (vix) an optionally substituted 5- to 13-membered heterocyclic group which is mentioned below, (9) a 5- through 13-membered heterocyclic group containing 1–4 hetero-atom(s) selected from oxygen (O), sulfur (S) and nitrogen (N) as ring members, the heterocyclic group being optionally substituted by (i) halogen, (ii) $C_{1-4}$ alkyl, (iii) $C_{1-3}$ alkoxy, (iv) $C_{1-4}$ alkylthio, (v) phenoxy which may optionally be substituted by a halogen, (10) sulfo, (11) $C_{6-14}$ aryl, e.g. phenyl, naphthyl, anthryl, phenanthryl, acenaphthyl, anthracenyl, etc, (12) $C_{3-7}$ cycloalkyl, (13) $C_{1-6}$ alkylenedioxy, e.g. methylenedioxy, ethylenedioxy, propylenedioxy, 2,2 dimethylenedioxy, etc, (14) oxo, (15) thioxo, (16) $C_{2-4}$ alkenyl, (17) $C_{3-4}$ alkynyl, e.g. propagyl, 2-butenyl, etc, (18) $C_{3-10}$ cycloalkyl, (19) $C_{2-10}$ alkenyl, e.g. vinyl, allyl, isopropenyl, 1-butenyl, 2-butenyl, butadienyl, hexatrienyl, etc., and among others, $C_{2-6}$ alkenyl is preferable, (20) $C_{7-20}$ aralkyl, which has the same meaning as defined above, (21) amidino, and (22) azido.

When the hydrocarbon residue is cycloalkyl, cycloalkenyl, aryl or aralkyl, each of the group may have one to three of $C_{1-6}$ alkyl, e.g. methyl, ethyl, propyl, isopropyl, butyl, as a substituent. The $C_{1-6}$ alkyl group may further substituted by one to three of hydroxy, oxo, $C_{1-3}$ alkoxy, e.g. methoxy, ethoxy, n-propoxy, isopropoxy, $C_{1-3}$ alkylthio, halogen or carbamoyl.

The examples of the substituted alkyl, mention is made of (1) formyl, i.e. methyl is substituted by oxo, (2) carboxyl, i.e. methyl is substituted by oxo and hydroxy, (3) $C_{1-6}$ alkoxy-carbonyl, i.e. methyl is substituted by oxo and alkoxy, e.g. methoxycarbonyl, ethoxycarbonyl, t-butoxycarbonyl, hydroxy-$C_{1-6}$ alkyl, e.g. hydroxymethyl, hydroxyethyl, hydroxypropyl, hydroxybutyl, (4) $C_{1-3}$ alkoxy-$C_{1-6}$ alkyl, e.g. methoxymethyl, ethoxyethyl, ethoxybutyl, propoxymethyl, propoxyhexyl.

In the above optionally substituted hydrocarbon residue, the number of the substituent(s) is preferably 1 to 6, more preferably 1 to 5, and still preferably 1 to 3 and most preferably 1 to 2. The number of the substituent(s) which is substituted on the substituent is preferably 1 to 3, more preferably 1 or 2.

In the formula (I), n denotes 1 to 3, preferably 1 or 2, more preferably 1.

The $C_{1-6}$ alkyl group in the $C_{1-6}$ alkyl group which is substituted by a $C_{1-6}$ alkoxy-carbonyl group or a group of the formula: —NH—$SO_2$—$R^5$ mentioned for $R^3$ includes methyl, ethyl, n-propyl, isopropyl, n-butyl, isobutyl, sec-butyl, t-butyl, pentyl, hexyl, etc. Particularly preferred is methyl or ethyl.

The $C_{1-6}$ alkoxy in $C_{1-6}$ alkoxy-carbonyl group of $R^3$ includes methoxy, ethoxy, propoxy, isopropoxy, n-butoxy, isobutoxy, t-butoxy, pentoxy, hexyloxy. In particular, $C_{1-4}$ alkoxy is preferable.

The $C_{1-6}$ alkyl group of the $C_{1-6}$ alkyl which may optionally be substituted by halogen of $R^5$ includes the same groups as mentioned above. In particular, methyl or ethyl, is preferred.

The halogen includes fluorine, chlorine, bromine, iodine. Among others, fluorine and chloride is preferable.

The number of the substituent is preferably 1 to 3.

The $C_{6-14}$ aryl group of $R^5$ includes phenyl, naphthyl, anthryl. Among others, phenyl is preferable.

The heterocyclic group of the optionally substituted heterocyclic group mentioned for $R^4$ includes 3- through 13-membered, preferably 5- through 13-membered, heteroaromatic groups and non-aromatic saturated or unsaturated heterocyclic groups containing 1–4 hetero-atoms selected from among oxygen (O), sulfur (S) and nitrogen (N) as ring members.

The preferred heteroaromatic group includes mono-cyclic heteroaromatic groups such as furyl, thienyl, pyrrolyl, pyrrolinyl, oxazolyl, isoxazolyl, thiazolyl, isothiazolyl, imidazolyl, imidazolinyl, pyrazolyl, pyrazolinyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, triazinyl, 1,2,3-triazolyl, triazolidinyl, 1,2,4-triazolyl, tetrazolyl, pyridyl, pyridazinyl, pyrimidinyl, pyrazinyl, triazinyl, etc., and fused heteroaromatic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.

The preferred nonaromatic heterocyclic group includes oxiranyl, azetidinyl, oxetanyl, thietanyl, thiazolidinyl, pyrrolidinyl, pyrazolidinyl, imidazolidinyl, tetrahydrofuryl, thioranyl, piperidyl, piperidinyl, tetrahydropyranyl, morpholinyl, thiomorpholinyl, piperazinyl, oxazolino, hexamethyleneamino, etc.

As the heterocyclic group, a 5 to 7 membered heretocyclic group is prefereble, and a 5 to 6 membered heterocyclic group is more prefereble.

The above heterocyclic groups may each have 1 or more, preferably 1–3, suitable substituents, which can be the same as the above-mentioned substituents for hydrocarbon residue.

The spacer group mentioned for W includes $C_{1-4}$ alkylene, e.g. methylene, ethylene, etc, $C_{2-6}$ alkenylene, e.g. vinylene, butadienylene, etc, groups of the formula —($CH_2$)$cNR^7$—, where c represents an integer of 0–3, $R^7$ represents hydrogen or $C_{1-6}$ alkyl, e.g. methyl, ethyl, propyl, butyl, etc, —CO—, groups of the formula —$CONR^7$—, where $R^7$ is as defined above, —O—, —S(O)f—, where f represents an integer of 0 to 2, and —$NR^7S(O)e$—, where e represents an integer of 0–2; $R^7$ is as defined above, among other groups.

The optionally substituted hydrocarbon residue of $R^1$ is preferably $C_{1-20}$ hydrocarbon residue. Among others, $C_{1-10}$ alkyl, $C_{3-10}$ cycloalkyl, $C_{2-10}$ alkenyl, $C_{6-14}$ aryl and $C_{7-20}$ aralkyl are preferable.

As $R^1$, an optionally substituted $C_{7-20}$ aralkyl is most preferable.

As preferable examples of the substituent in the optionally substituted hydrocarbon residue of $R^1$ is (1) halogen, (2) nitro, (3) cyano, (4) an optionally substituted hydroxyl group, (5) a group of the formula: —S(O)f—$R^6$ wherein f denotes an integer of 0 to 2, and $R^6$ is a hydrogen atom or an optionally substituted hydrocarbon residue, (6) an optionally substituted amino group or (7) an optionally substituted 5- or 6-membered heterocyclic group which contains 1 to 4 heteroatom(s) of oxygen, sulfur or nitrogen.

The group $R^1$ is preferably the group of the formula: —($CH_2$)$_m$Q, wherein m is an integer of 0 to 3 and Q is an optionally substituted $C_{6-14}$ aryl group, an optionally substituted $C_{3-10}$ cycloalkyl group or an optionally substituted 5 to 13-membered heterocyclic group.

As the above optionally substituted $C_{6-14}$ aryl group, a $C_{6-14}$ aryl group which may have one to three substituent(s) of halogen, nitro, cyano, amino, carboxyl which may be optionally substituted, $C_{1-6}$ alkylenedioxy, $C_{1-6}$ alkoxy, $C_{1-6}$ alkylthio or a group of the formula: —A—$R^{12}$, wherein A is a spacer group having the same meaning as W, and $R^{12}$ is $C_{1-6}$ alkyl. The optionally substituted carboxyl has the same meaning of the above group of the formula: —CO—$R^{11}$.

In particular, Q is preferably $C_{6-14}$ aryl group optionally substituted by (1) halogen, (2) $C_{1-6}$ alkoxy, (3) $C_{1-6}$ alkylthio, (4) a group of the formula: —A—$R^{12}$ (wherein A and $R^{12}$ have the same meaning as defined above. Furthermore, Q is more preferably $C_{6-14}$ aryl which may be substituted by (1) halogen, (2) $C_{1-6}$ alkylthio or (3) $C_{1-6}$ alkoxy. As the aryl, phenyl is most preferable.

As the preferable group of $R^1$, mention is made of a $C_{7-20}$ aralkyl which is optionally substituted. As the preferable example of the substituent, mention is made of (1) halogen, (2) nitro, (3) hydroxy, (4) cyano, (5) $C_{1-4}$ alkyl, (6) $C_{1-4}$ alkylthio, (7) $C_{1-4}$ alkoxy. Among others, (1) halogen and (2) $C_{1-4}$ alkylthio is preferable, and $C_{1-4}$ alkylthio is most preferable. As the $C_{7-20}$ aralkyl, benzyl is most preferable.

As the optionally substituted amino group represented by $R^8$, mention is made of a group of the formula: —$NR^9R^{10}$, wherein $R^9$ and $R^{10}$ are the same or different hydrogen, hydrocarbon residue, which has the same meaning as defined above, $C_{1-6}$ acyl or heterocyclic group which is mentioned below.

As the preferred group of $R^2$, mention is made of those of $R^1$.

Further, as the group $R^2$, hydrogen or an optionally substituted $C_{1-10}$ alkyl is preferable. As the alkyl, an optionally substituted $C_{1-6}$ alkyl is more preferable, and furthermore an optionally substituted $C_{1-4}$ alkyl is most preferable.

As the substituent on the alkyl of $R^2$, preferred examples are (1) halogen, (2) nitro, (3) cyano, (4) an optionally substituted hydroxyl group, (5) a group of the formula: —S(O)f—$R^6$, wherein f denotes an integer of 0 to 2, and $R^6$ is a hydrogen atom or an optionally substituted hydrocarbon residue, (6) an optionally substituted amino group or (7) an optionally substituted 5- or 6-membered heterocyclic group which contains 1 to 4 heteroatoms of oxygen, sulfur or nitrogen. Among others, as substituents, (1) halogen, (2) nitro, (3) hydroxy, (4) cyano, (5) $C_{1-4}$ alkylthio, (6) $C_{1-4}$ alkoxy, (7) $C_{1-6}$ alkyl-carbonyloxy, (8) $C_{3-6}$ cycloalkyl-oxycarbonyloxy are preferred. In these groups, (1) $C_{1-6}$ alkyl-carbonyloxy or (2) $C_{3-6}$ cycloalkyl-oxycarbonyloxy is most preferable.

As the group $R^3$, preferable examples include (a) a $C_{1-6}$ alkyl group which is substituted by (1) a $C_{1-6}$ alkoxy-carbonyl group or (2) a group of the formula: —NH—$SO_2$—$R^{5'}$, wherein $R^{5'}$ is a $C_{1-6}$ alkyl group or a $C_{6-14}$ aryl group, (b) a $C_{1-6}$ alkyl group which is substituted by a group of the formula: —NH—$SO_2$—$R^5$, wherein $R^5$ is (1) a $C_{1-6}$ alkyl group which may optionally substituted by halogen or (2) or $C_{6-14}$ aryl group, (c) a $C_{1-6}$ alkyl group which is substituted by a group of the formula: —NH—$SO_2$—$R^{5'}$, wherein $R^{5'}$ is a $C_{1-6}$ alkyl group or a $C_{6-14}$ aryl group, (d) a $C_{1-6}$ alkyl group which is substituted by a group of the formula: —NH—$SO_2$—$R^{5''}$, wherein $R^{5''}$ is a $C_{1-3}$ alkyl group which may-optionally be substituted by halogen or a phenyl group, (e) a $C_{1-6}$ alkyl group which is substituted by a group of the formula: —NH—$SO_2$—$R^{5'''}$, wherein $R^{5'''}$ is a $C_{1-3}$ alkyl group or a phenyl group, (f) a $C_{1-6}$ alkyl group which is substituted by a group of the formula: —NH—$SO_2$—$R^{5''''}$, which $R^{5''''}$ is a $C_{1-6}$ alkyl group, and (g) a $C_{1-6}$ alkyl group which is substituted by a group of the formula: —NH—$SO_2$—$R^{5''''}$, wherein $R^{5''''}$ is a $C_{1-3}$ alkyl group.

As the group $R^4$, an optionally substituted $C_{6-14}$ aryl group, an optionally substituted $C_{7-20}$ aralkyl group, an optionally substituted $C_{3-7}$ cycloalkyl group, an optionally substituted carboxyl group of the formula —CO—$R^{11}$ as mentioned above or an optionally substituted 5- to 13-membered heterocyclic group which contains 1 to 4 heteroatoms of oxygen, sulfur or nitrogen (5- or 6-membered heterocyclic group is preferable), are preferable.

The substituent of the above groups are the same as those of hydrocarbon residue as mentioned above.

As preferred examples of the substituents, mention is made of (1) halogen, (2) nitro, (3) cyano, (4) $C_{1-6}$ alkoxy which may optionally be substituted by $C_{1-6}$ alkoxy, carboxyl, halogen, $C_{1-6}$ alkyl-carbamoyl, 5 to 7 membered nitrogen-containing heterocyclic group, (5) $C_{7-13}$ aralkyloxy, (6) $C_{1-4}$ alkyl which may be substituted by hydroxy, oxo or $C_{1-3}$ alkoxy, (7) $C_{1-6}$ alkanoyl, (8) $C_{1-4}$ alkylthio, (9) $C_{2-6}$ alkenyloxy, (10) $C_{1-6}$ alkoxy-carbonyl or (11) $C_{1-6}$ alkyl-aminocarbonyl.

As the group $R^4$, preferred examples are a $C_{6-14}$ aryl group, a $C_{3-10}$ cycloalkyl group, a 5 to 13 membered heterocyclic group, or carboxyl group, each of these groups being optionally substituted, and an optionally substituted $C_{6-14}$ aryl group is more preferable.

In the group $R^4$, as preferred examples of the substituents, mention is also made of $C_{1-6}$ alkoxy which may optionally substituted by a $C_{1-6}$ alkoxy, carboxyl, halogen, $C_{1-6}$ alkyl-carbamoyl or 5 to 7 membered nitrogen-containing heterocyclic group. Additional preferred examples of $R^4$ are $C_{6-14}$ aryl which may be substituted by (1) $C_{1-6}$ alkoxy, which may be substituted by halogen or $C_{1-6}$ alkoxy or (2) $C_{1-6}$ alkylthio. A most preferred example of the group $R^4$ is $C_{6-14}$ aryl which may optionally be substituted by an optionally substituted $C_{1-6}$ alkoxy, especially $C_{1-6}$ alkoxy which may optionally be substituted by $C_{1-6}$ alkoxy.

Still other preferred examples of the group $R^4$ are phenyl which may be substituted by (1) $C_{1-4}$ alkoxy which may be substituted by $C_{1-6}$ alkoxy, carboxy, $C_{1-6}$ alkyl-carbamoyl, piperazinecarbonyl or halogen, (2) $C_{7-8}$ aralkyloxy, (3) $C_{1-4}$ alkyl which may optionally be substituted by hydroxy, oxo or $C_{1-3}$ alkoxy, especially $C_{1-4}$ alkyl which may optionally be substituted by $C_{1-3}$ alkoxy, (4) $C_{1-6}$ alkanoyl, (5) $C_{2-4}$ alkenyloxy, (6) $C_{1-6}$ alkoxy-carbonyl or (7) $C_{1-6}$ alkyl-carbamoyl.

W is preferably a chemical bond or an spacer group of the formula —S(O)f—, wherein f represents an integer of 0–2, the formula —CO—, or the formula —CONR$^7$—, where $R^7$ represents $C_{1-4}$ alkyl such as methyl, ethyl, propyl, butyl, etc. W is most preferably a chemical bond.

In the above definitions, $C_{2-6}$ alkenyl is exemplified by vinyl, allyl, isopropenyl, butenyl, hexatrienyl, $C_{2-4}$ alkenyl is exemplified by vinyl, allyl, isopropenyl, butenyl.

$C_{6-14}$ aryl is exemplified by phenyl, naphthyl, anthryl, phenanthryl, acenaphthyl, anthracenyl, especially phenyl is most preferable.

$C_{7-8}$ aralkyl is exemplified by benzyl and phenethyl.

$C_{1-6}$ alkoxy is exemplified by methoxy, ethoxy, propoxy, isopropoxy, n-butoxy, isobutoxy, s-butoxy, t-butoxy, pentyloxy, hexyloxy, $C_{1-4}$ alkoxy is exemplified by methoxy, ethoxy, propoxy, isopropoxy, n-butoxy, isobutoxy, s-butoxy, t-butoxy. $C_{1-3}$ alkoxy is exemplified by methoxy, ethoxy, propoxy, isopropoxy.

Halogen is exemplified by fluorine, chlorine, bromine, iodine.

$C_{1-6}$ alkyl is exemplified by methyl, ethyl, n-propyl, isopropyl, n-butyl, isobutyl, t-butyl, pentyl, hexyl. $C_{1-4}$ alkyl is exemplified by methyl, ethyl, n-propyl, isopropyl, n-butyl, isobutyl, t-butyl. $C_{1-3}$ alkyl is exemplified by methyl, ethyl, n-propyl, isopropyl.

$C_{3-10}$ cycloalkyl is exemplified by cyclopropyl, cyclobutyl, cyclopentyl, cyclohexyl, cycloheptyl, cyclooctyl, cyclononyl. $C_{3-7}$ cycloalkyl is exemplified by cyclopropyl, cyclobutyl, cyclopentyl, cyclohexyl, cycloheptyl. $C_{3-6}$ cycloalkyl is exemplified by cyclopropyl, cyclobutyl, cyclopentyl, cyclohexyl.

$C_{1-6}$ acyl is exemplified by formyl and $C_{1-6}$ alkanoyl of the formula: —CO—$R^{13}$, wherein $R^{13}$ is methyl, ethyl, propyl, isopropyl, n-butyl, isobutyl, s-butyl, t-butyl, pentyl.

$C_{2-6}$ alkanoyl is exemplified by the formula: —CO—$R^{13}$, wherein $R^{13}$ has the same meaning as defined above. $C_{1-4}$ acyl is exemplified by formyl and the formula: —CO—$R^{13'}$ (wherein $R^{13'}$ is methyl, ethyl, n-propyl, isopropyl.).

Preferable five to seven-membered heterocyclic groups which contain 1 to 4 heteroatoms of oxygen, sulfur or nitrogen are exemplified by thienyl, furyl, pyrrolyl, pyrazolyl, thiazolyl, isothiazolyl, oxazolyl, isoxazolyl, imidazolyl, triazolyl, tetrazolyl, furazanyl, tetrahydrofuryl, pyridyl, pyrimidinyl, pyridazynyl, oxadiazolyl, tetrahydropyranyl, morpholinyl, thiomorpholinyl, pyrrolidinyl, pyrrolinyl, pyrazolidinyl, pyrazolinyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, hexamethyleneaminyl, oxazolidinyl or thiazolidinyl. As more preferable heterocyclic groups, mention is made of 5 to 6 membered heterocyclic groups. In particular, pyrrolidinyl, pyrazolinyl, pyrazolyl, piperidinyl, piperazinyl, morpholinyl and thiomorpholinyl are preferable.

In the above definition, the number of the substituent(s) is preferably 1 to 3.

The present compound (I) and their salts can be produced by per se known methods. Typically, the present compound can be produced by the processes described below.

(a) The compound (I') in which $R^1$ is hydrogen and $R^2$ is an optionally substituted hydrocarbon residue, that is to say compound (IV') or a salt thereof can be produced by cyclizing a compound of the following general formula (II') or a salt thereof with a base.

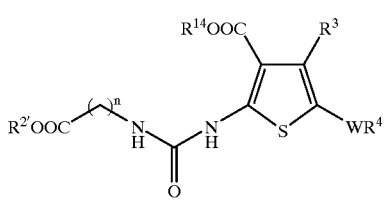

(II')

wherein $R^{2'}$ represents an optionally substituted hydrocarbon residue; $R^3$, $R^4$, W and n are as defined hereinbefore; $R^{14}$ represents hydrogen or an optionally substituted hydrocarbon residue being the same as above.

This reaction is carried out in a solvent that does not interfere with the reaction. The solvent that can be used includes but is not limited to alcohols such as methanol, ethanol, isopropyl alcohol, etc. and ethers such as dioxane, tetrahydrofuran, etc.

The base mentioned above may for example be an alkali metal alkoxide, e.g. sodium methoxide, sodium ethoxide, sodium isopropoxide, etc., or an alkali metal hydride, e.g. sodium hydride.

The amount of the base with respect to compound (II') is about 1.1–5 molar equivalents, preferably about 1.5–3 equivalents.

The reaction temperature may range from about 10° C. to the boiling point of the solvent used and is preferably about 25° C. to the boiling point of the solvent.

The reaction time is several minutes to a few days and preferably about 10 minutes to 2 days.

(b) Compound (IV') or a salt thereof can be produced by cyclizing a compound of the following general formula (III) or a salt thereof in the presence of a base and subjecting the cyclization product to electrophilic substitution reaction for introducing a group of the formula —$WR^4$, where W and $R^4$ are as defined hereinbefore.

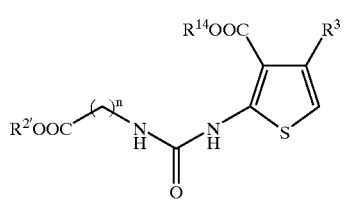

(III)

wherein $R^{2'}$ represents an optionally substituted hydrocarbon residue; $R^3$ is as defined hereinbefore; $R^{14}$ represents hydrogen or an optionally substituted hydrocarbon residue; n represents a whole number of 1–3.

This cyclization reaction is conducted in a solvent that does not interfere with the reaction. The solvent that can be used includes but is not limited to alcohols such as methanol, ethanol, isopropyl alcohol, etc. and ethers such as dioxane, tetrahydrofuran, etc.

The base that can be used includes alkali metal alkoxides such as sodium methoxide, sodium ethoxide, sodium isopropoxide, etc. and alkali metal hydrides such as sodium hydride etc.

The proportion of the base with respect to compound (III) is about 1.1–5 molar equivalents and preferably about 1.5–3 equivalents.

The reaction temperature may range from about 10° C. to the boiling point of the solvent used and is preferably about 25° C. to the boiling point of the solvent.

The reaction time is several minutes to a few days and preferably about 10 minutes to 2 days.

This electrophilic substitution can be achieved by a per se known electrophilic substitution reaction. Specific examples of such reaction are the nitration reaction, e.g. the reaction using fuming nitric acid-concentrated sulfuric acid or sodium nitrate-concentrated sulfuric acid, acylation reaction, e.g. the reaction using an acid chloride-aluminum chloride, formylation reaction, e.g. the reaction using phosphorus oxychloride-N,N-dimethylformamide or N-methylformanilide, and halogenation reaction, e.g. the reaction using N-bromosuccinimide, bromine-pyridine, or sulfuryl chloride.

The electrophilic substitution reaction can be carried out under per se known reaction conditions. Typical sets of conditions are as follows. The nitration reaction is conducted in fuming nitric acid-concentrated sulfuric acid, sodium nitrate-concentrated sulfuric acid, or potassium nitrate-concentrated sulfuric acid at about 0–80° C. The acylation reaction is carried out using an alkanoyl chloride, e.g. acetyl chloride, propionyl chloride, etc, in a solvent that does not interfere with the reaction, e.g. nitrobenzene, nitromethane, carbon disulfide, etc, in the presence of a Lewis acid catalyst, e.g. aluminum chloride, titanium tetrachloride, etc, at about 0–100° C. The formylation reaction is carried out using phosphorus oxychloride-N,N-dimethylformamide/N-methylformanilide, oxalyl chloride-N,N-dimethylformamide/N-methylformanilide, thionyl chloride-N,N-dimethylformamide/N-methylformanilide in a solvent that does not interfere with the reaction, e.g. benzene, toluene, xylene, tetrahydrofuran, dioxane, 1,2-dichloroethane, etc, or in the absence of a solvent at about 15–130° C. The halogenation reaction is carried out using sulfuryl chloride, N-chlorosuccinimide, N-bromosuccinimide, bromine, chlorine, or iodine in a solvent that does not interfere with the reaction, e.g. dichloromethane, chloroform, carbon tetrachloride, 1,2-dichloroethane, pyridine, benzene, toluene, xylene, etc, at about 15–130° C.

The substituent group introduced by the above electrophilic substitution reaction can be subjected, where desired, to a functional group transformation reaction. This functional group transformation reaction can be carried out by the per se known transformation reaction. Specific examples of the reaction are reduction reaction, acylation reaction, sulfonylation reaction, alkylation reaction, diazo coupling reaction, Wittig reaction, halogenation reaction, halide-Grignard reaction, and coupling reaction with an organozinc reagent, an organoboron reagent or an organotin reagent.

(c) The compound (I') wherein $R^1$ represents an optionally substituted hydrocarbon residue and $R^2$ represents an optionally substituted hydrocarbon residue, that is to say compound (VI), or a salt thereof can be produced by reacting the compound (IV') or a salt thereof as prepared by the above procedure (a) or (b) with a compound of the general formula (V'): $R^1$—X (V'), wherein $R^1$ represents an optionally substituted hydrocarbon residue; X represents halogen, or a salt thereof.

The optionally substituted hydrocarbon residue mentioned for $R^1$ has the same meaning as defined hereinbefore. The halogen mentioned for X includes fluorine, chlorine, bromine, and iodine.

This reaction is conducted in a solvent that does not interfere with the reaction. The solvent that can be used includes ethers such as tetrahydrofuran, dioxane, etc., aromatic hydrocarbons such as benzene, toluene, xylene, etc., amides such as N,N-dimethylformamide, N,N-dimethylacetamide, etc., dimethyl sulfoxide, and so on. This reaction is preferably carried out under basic conditions, e.g. in the presence of potassium carbonate, sodium hydride, potassium hydride, potassium t-butoxide, or the like.

The proportion of compound (V') with respect to compound (IV') is about 1–5 molar equivalents and preferably about 1.1–2.5 equivalents.

When a base is used, its proportion is about 1–5 equivalents, preferably 1.1–3 equivalents, based on compound (IV').

The reaction temperature may range from about 10° C. to the boiling point of the solvent used and is preferably about 20° C.–130° C.

The reaction time ranges from several minutes to a few days and preferably from about 15 minutes to about 2 days.

(d) The hydroxyl group in the starting compound can be substituted by various kinds of groups. The reaction is carried out in an appropriate solvent, e.g. dimethylformamide (DMF), acetonitrile, acetone. To the solution of the starting compound is added halide such as alkyl halide, e.g. propyl iodide, isobutyl iodide, ethybromo acetate, or aralkyl halide, e.g. benzylchlolide. The mixture is stirred at 0 to 40° C. for 2 to 18 hours.

For example, in the case of ethyl bromoacetate, the obtained acetic acid ester is hydrolyzed in an adequate solvent and base, e.g. iN NaOH solution in ethyl alcohol, at room temperature for 2 to 12 hours. The acetic acid compound is dissolved in an adequate solvent, e.g. tetrahydrofuran (THF). To the solution is added isobutyl chloroformate in the presence of an adequate base, e.g. $Et_3N$, and the reaction is carried out at 0° C. for 1 to 4 hours. To the solution is added adequate amine derivatives, e.g. methylamine, propylamine, piperidine. The reaction is carried out at 0° C. to room temperature for 1 to 12 hours.

Said starting compound which has a hydroxyl group is produced by acid-hydrolysis of a compound such as one having an alkoxy group. The acid hydrolysis is carried out in a conventional manner such as by adding 1N hydrochloric acid in an appropriate solvent such as tetrahydrofuran or alcohol, e.g. methanol, ethanol, at 0° C. to room temperature for one to 10 hours.

(e) The present compound (I'), wherein $WR^4$ is an alkanoyl- phenyl group can be produced by the introduction of a alkanoyl-phenyl group to the halogenated compound ($WR^4$=Br). The halogenated compound is obtained by the halogenation reaction with the starting compound ($WR^4$=H). The halogenation is carried out in an adequate solvent, e.g. carbontetrachloride or chloroform. To the solution is added N-bromosuccinimide and catalytic amount of 2,2'-azobis(isobutyronitrile). The reaction is carried out at 100 to 120° C. for 1 to 4 hours. The introduction reaction of alkanoyl phenyl group is carried out in an appropriate degased solvent, e.g. dimethoxyethane (DME). To the solution is added alkanoyl phenyl borate, palladium compound, e.g. $Pd(PPh_3)_4$(Ph=phenyl) and sodium carbonate (2M, $Na_2CO_3$). The alkanoyl phenyl borate is synthesized by the reaction of alkanoyl phenyl bromide with adequate borate, e.g. (i-PrO)$_3$B(Pro=propyl) in the presence of adequate base, e.g. BuLi (Bu=butyl). The introduction reaction is carried out at room temperature to 120° C. for 1 to 12 hours under inert gas atmosphere.

(f) The present compound (I'), wherein $WR^4$ is alkylphenyl group can be produced by the similar manner as shown in (e) with alkyl phenyl-borates instead of alkanoyl phenyl borates.

Any other group in the compound can be introduced by any known per se known methods.

(g) The present compound (I), wherein $R^3$ is an alkoxycarbonyl group, can be produced by introducing a cyano group, and then subjecting the obtained compound to esterification.

In the reaction of the introduction of cyano group, the starting compound is dissolved in an appropriate solvent, e.g. dimethylsulfoxide (DMSO), and to the solution is added sodium cyanide. The reaction is carried out at 40 to 60° C. for 2 to 12 hours.

The esterification reaction is carried out in an appropriate solvent such as ethyl alcohol. The reaction is conducted by mixing the starting compound and alcohol solution, e.g. ethyl alcohol, saturated with hydrochloric acid. The reaction is carried out at 80 to 120° C. for 12 to 48 hours.

(h) The present compound (I'), wherein $R^3$ is an alkyl group which is substituted by a group —NH—$SO_2$—$R^5$, wherein $R^5$ is the same meaning as defined above, can be synthesized by (i) halogenation of this alkyl group and (ii) nucleophilic substitution of this halogen with a sulfonamide compound in the presence of appropriate base, e.g. sodium hydride.

The halogenation is carried out in an appropriate solvent, e.g. carbon tetrachloride. To the solution is added N-bromosuccinimide or catalytic amount of 2,2'-azobis (isobutyronitrile). The reaction is carried out at 100 to 120° C. for 1 to 4 hours.

The nucleophilic substitution reaction is carried out in a similar manner as described in the above process (P) on the reaction of the compound (IV') and (V'). Particularly, in an appropriate solvent such as N,N-dimethylformamide (DMF). To the solution is added sodium hydride washed with n-hexane and sulfonamide derivatives, e.g. methanesulfonamide, ethanesulfonamide, benzenesulfonamide. The reaction is carried out at 0 to 40° C. for 1 to 24 hours.

(i) The compound (I') wherein $R^2$ is hydrogen, that is to say compound (VII) or (VII'), or a salt thereof, can be obtained by subjecting the compound (IV') or (VI), or a salt thereof, as produced in the above manner to a reaction for conversion of $R^2$ to hydrogen.

The reaction for converting $R^2$ to hydrogen or from esters to carboxylic groups may for example be a alkali-hydrolysis reaction. This hydrolysis reaction is conducted by reacting compound (IV') or (VI), or a salt thereof, with a base in a solvent that does not interfere with the reaction. The solvent that can be used for this reaction includes alcohols such as methanol, ethanol, isopropyl alcohol, etc., ethers such as tetrahydrofuran, dioxane, etc., amides such as N,N-dimethylformamide, N,N-dimethylacetamide, etc., and dimethyl sulfoxide, among others. The base that can be used includes alkali metal hydroxides such as lithium hydroxide, sodium hydroxide, potassium hydroxide, etc., alkaline earth metal hydroxides such as calcium hydroxide, barium hydroxide, etc., and alkali metal carbonates such as potassium carbonate, sodium carbonate, etc. The proportion of the base to compound (IV') or (VI) is about 1–10 molar equivalents and preferably about 1.5–5 equivalents. The reaction temperature may range from about 10° C. to the boiling point of the solvent used and is preferably about 15°–100° C. The reaction time is several minutes to a few days and preferably about 15 minutes to two days.

The compound of the item (28) aforementioned can be produced by subjecting a starting compound (I') in which $R^3$ is alkoxycarbonyl-methyl to an alkali-hydrolysis as mentioned above.

(j) The present compound (I'), wherein $R^2$ is the optionally substituted hydrocarbon residue such as pivaloyloxymethyl or 1-(cyclohexyloxycarbonyloxy) ethyl can be synthesized by the condensation reaction of the compound (I', $R^2$=H) with chloride agents (e.g. pivaloyloxymethyl chloride, 1-(cyclohexyloxycarbonyloxy)ethyl-1-chloride) or acid anhydride agents, e.g. pivalic anhydride, in an appropriate solvent, e.g. dimethylformamide (DMF), in the presence of adequate base (e.g. $K_2CO_3$) and potassium iodide (KI). The reaction is carried out at 0° C. to room temperature for 2 to 24 hours.

The starting compounds (II') and (III), as well as salts thereof, which are to be employed in the above production processes can be produced typically by the following alternative processes A and B.

1. Process A

In this process, either a compound of the general formula (VIII) or a salt thereof or a compound of the general formula (VIII') or a salt thereof is reacted with an isocyanic acid ester derivative.

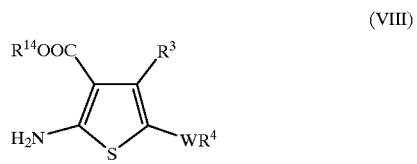

(VIII)

wherein $R^3$, $R^4$, $R^{14}$, W, and n are as defined hereinbefore,

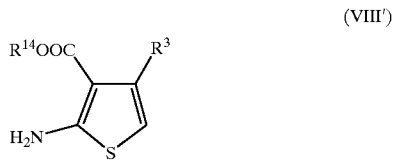

(VIII')

wherein $R^3$ and $R^{14}$ are as defined as hereinbefore.

The isocyanic acid derivative mentioned above may for example be an isocyanate derivative of the formula $R^7OOC-(CH_2)_n-NCO$, wherein $R^7$ and n are as defined hereinbefore.

The reaction of compound (VIII) or compound (VIII'), or a salt thereof, with said isocyanate derivative is carried out in a solvent which does not interfere with the reaction, e.g. tetrahydrofuran, pyridine, dioxane, benzene, dichloromethane, 1,2-dichloroethane, toluene, xylene, etc, at about 15–130° C. and preferably at about 25–130° C.

The isocyanate derivative is used in a proportion of about 1–5, preferably about 1.1–2.5 molar equivalents, relative to compound (VIII) or (VIII').

The reaction time is several minutes to a few days and preferably about 15 minutes to about 2 days.

2. Process B

This process comprises reacting compound (VIII) or (VIII'), or a salt thereof, with phosgene or the equivalent, e.g. triphosgene of bis(trichloromethyl) carbonate or the like, diphosgene of trichloromethyl chloroformate or the like, etc, to give the isocyanate derivative and adding an amine, e.g. a compound of the formula $R^{14}OOC-(CH_2)$ n—$NH_2$, where $R^{14}$ and n are as defined hereinbefore.

The reaction between compound (VIII) or (VIII'), or a salt thereof, and phosgene or the equivalent is conducted in a solvent that does not interfere with the reaction, e.g. dioxane, tetrahydrofuran, benzene, toluene, xylene, 1,2-dichloroethane, chloroform, etc, at about 15–130° C. and preferably at about 25–130° C.

Phosgene or the equivalent thereof is used in a proportion of about 0.5–2 molar equivalents, preferably about 0.9–1.1 equivalents, with respect to compound (VIII) or (VIII').

The reaction time is several minutes to a few days and preferably about 15 minutes to about two days.

The amine addition reaction is carried out in a solvent that does not interfere with the reaction, e.g. pyridine, tetrahydrofuran, dioxane, benzene, dichloromethane, 1,2-dichloroethane, toluene, xylene, etc, at about 15–130° C. and preferably at about 25–130° C.

The amine is used in a proportion of about 1–5 molar equivalents, preferably about 1.1–3 equivalents, with respect to compound (VIII) or (VIII').

The reaction time is several minutes to a few days and preferably about 15 minutes to about two days.

The compound (VIII) or a salt thereof for use in the above reaction can be produced by the following process.

A ketone having an active methylene group, e.g. a compound (IX) of the formula $R^3-CO-CH_2-WR^4$, where $R^3$, $R^4$ and W are as defined hereinbefore, is reacted with a cyanoacetic ester derivative and sulfur according to the method of K. Gewald, E. Schinke and H. Bettcher, Chem. Ber., 99, 94–100, 1966, to give compound (VIII) or a salt thereof. Thus, the above-mentioned ketone and the cyanoacetate derivative are heated together under reflux in a solvent that does not interfere with the reaction, e.g. benzene, toluene, etc, in the presence of acetic acid and ammonium acetate to give the alkylidenecyanoacetate derivative which is then heated in a solvent that does not interfere with the reaction, e.g. methanol, ethanol, etc, in the presence of sulfur and a base, e.g. an organic base such as triethylamine, ethyldiisopropylamine, dimethyl-aminopyridine, etc, at a temperature of about 50–80° C. to give 2-aminothiophene derivative i.e. Compound (VIII).

Compound (VIII') can be synthesized by the method of K. Gewald (Chem. Ber., 98, 3571–3577 (1965) (K. Gewald) and Chem. Ber., 99, 2712–2715 (1966) (K. Gewald and E. Schinke).

In this specification, "the present compound" means the compounds of this invention, such as the compound (I), the compound (I') and the compound of the above item (28).

The salt of the present compound thus obtained is preferably a physiologically acceptable acid addition salt. Such addition salt may for example be any of salts with inorganic acids, e.g. hydrochloric acid, hydrobromic acid, nitric acid, sulfuric acid, phosphoric acid, etc, and salts with organic acids, e.g. formic acid, acetic acid, trifluoroacetic acid, fumaric acid, oxalic acid, tartaric acid, maleic acid, citric acid, succinic acid, malic acid, methanesulfonic acid, benzenesulfonic acid, etc. Where the present compound of the invention has an acidic group such as —COOH, the present compound may form salts with inorganic bases, e.g. alkali metals or alkaline earth metals such as sodium, potassium, calcium, magnesium, etc, or ammonia, or organic bases, e.g. trimethylamine, triethylamine, pyridine, picoline, ethanolamine, diethanolamine, triethanolamine, dicyclohexylamine, N,N'-dibenzylethylenediamine, etc.

The compound or salt of the invention as produced by the above-described technology can be isolated and purified by the conventional procedures such as recrystallization, distillation, and chromatography, among other fractionation techniques. Where the present compound is obtained as a free compound, it can be converted to a salt by a per se known method or any method analogous therewith. Conversely where a salt is obtained, it can be converted to the free compound or a different salt by a per se known method or any method analogous therewith.

The salts of the compounds (II) to (IX) can also be salts similar to the salts of compound (I).

Where the present compound or salt of the invention is an optically active compound, it can be fractionated into the d- and l-compounds by a conventional optical resolution technique.

The present compound has only a low toxic potential and can, therefore, be safely used.

The endothelin antagonist composition of the present invention has remarkably potent endothelin receptor antagonist activity and can be administered as an endothelin antagonist to mammals, e.g. rat, mouse, rabbit, cat, dog, bovine, equine, and human being. Specifically, it can be used safely as a therapeutic drug for acute renal failure, myocardial infarction, liver disorder, angina pectoris, cerebral infarction, cerebrovasospasm, hypertension, kidney disease, asthma, ectopic angina, Raynaud's syndrome, pulmonary hypertension, surgical shock, chronic cardiac insufficiency, atherosclerosis, cardiac hypertrophy and migraine, among other diseases, as a prophylactic or therapeutic drug for organ, e.g. liver, surgery- or transplant-associated organic hypofunction, or as a prophylactic agent for post-PTCA vascular restenosis. Particularly, the composition is of great use as a therapeutic drug for acute renal failure, myocardial infarction, hepatic disorder, hypertension, and pulmonary hypertension, as a prophylactic or therapeutic drug for organ, e.g. liver, surgery- or transplant-associated organic hypofunction, or as a prophylactic drug for post-PTCA vascular restenosis. Furthermore, the compound of the present invention can be used as an inhibitor for vasoconstriction, such as an inhibitor for vasoconstriction of coronary artery, coronary vein, cerebrovascular system or pulmonary vascular system.

When the present compound or a salt thereof is to be administered to a human being, the compound as such or in the form of a pharmaceutical composition formulated with a suitable pharmacologically acceptable carrier, excipient or diluent can be safely administered orally or non-orally.

The pharmaceutical composition mentioned above may be provided in various dosage forms such as oral dosage forms, e.g. powders, granules, capsules, tablets, etc., injections, drip injections, dosage forms for external application, e.g. nasal dosage forms and transdermal drug delivery systems, and suppositories, e.g. rectal suppositories, vaginal suppositories.

These dosage forms can be manufactured by the established pharmaceutical procedures.

The present compound or salt of the invention can be formulated with a dispersant, e.g. Tween 80, Atlas Powder Co., U.S.A., HOC 60, Nikko Chemicals Co., polyethylene glycol, carboxymethylcellulose, sodium alginate, etc., a preservative, e.g methyl p-hydroxybenzoate, propyl p-hydroxybenzoate, benzyl alcohol, etc., an isotonizing agent, e.g. sodium chloride, mannitol, sorbitol, glucose, etc., and other additives to provide an aqueous injection, or dissolved, suspended or emulsified in vegetable oil, e.g. olive oil, sesame oil, cottonseed oil, corn oil, etc., propylene glycol, or the like to provide an oily injection.

For the manufacture of oral dosage forms, the present compound or salt of the invention is formulated with, for example, an excipient, e.g. lactose, sucrose, starch, etc., a disintegrator, e.g. starch, calcium carbonate, etc., a binder, e.g. starch, gum arabic, carboxymethylcellulose, polyvinylpyrrolidone, hydroxypropylcellulose, etc., and/or a lubricant, e.g. talc, magnesium stearate, polyethylene glycol 6000, etc., and compressed in the per se conventional manner. Where necessary, for masking the taste or insuring enteric or sustained release, the compressed composition can be coated by the per se known technique to provide an oral dosage form. The coating agent that can be used includes but is not limited to hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit, Rohm & Haas Co., Germany; methacrylic-acrylic acid copolymer, and pigments, e.g. red iron oxide, titanium dioxide, etc.. In the manufacture of an enteric release dosage form, it is preferable to provide an intermediate phase between an enteric phase and a drug-containing phase for phase-to-phase isolation.

For the manufacture of dosage forms for external application, the present compound or salt of the invention can be processed into solid, semisolid or liquid preparations. To provide a solid preparation, for instance, the present compound or a salt thereof is used as it is or in the form of a powdery composition formulated with an excipient, e.g. glycol, mannitol, starch, microcrystalline cellulose, etc., a thickener, e.g. natural gums, cellulose derivatives, acrylic polymers, etc., and other additives. A liquid preparation can be substantially similar to the injection mentioned above and may be an oily or aqueous suspension. The semisolid preparation can be an aqueous or oleaginous gel or ointment. To any of these preparations, a pH control agent, e.g. carbonic acid, phosphoric acid, citric acid, hydrochloric acid, sodium hydroxide, etc. and an antiseptic, e.g. p-hydroxybenzoic esters, chlorobutanol, benzalkonium chloride, etc. can be added.

For the production of suppositories, the present compound or salt of the invention can be processed into oleaginous or hydrous solid, semisolid or liquid suppositories in accordance with per se known production procedures. The oleaginous base that can be used for the above composition includes higher fatty acid glycerides, e.g. caccao butter, witepsols, Dynamite Nobel, Germany, medium fatty acid glycerides, e.g. miglyols, Dynamite Nobel, Germany, etc., and vegetable oils, e.g. sesame oil, soybean oil, cottonseed oil, etc.. The water-soluble base includes polyethylene glycols, propylene glycol, and the hydrogel base that can be used includes natural gums, cellulose derivatives, vinyl polymers, acrylic polymers, and so on.

The daily dosage of the present compound varies with the severity of illness, the recipient's age, sex, body weight, and sensitivity, administration time and interval, the property, recipe, and type of dosage form, and species of active ingredient, among other variables, and cannot be stated in general terms. Usually, however, the recommended dosage is about 0.01–10 mg, preferably about 0.03–3 mg, per kilogram body weight of the mammal and the above amount is usually administered once or in up to 4 divided doses a day.

The compound of the present invention has particularly high endothelin receptor antagonist activity. Moreover, the compound is highly amenable to oral administration and features a sustained action.

The following examples are intended to describe the present invention in further detail and should by no means be construed as defining the scope of the invention.

The $^1$H-NMR spectra shown were determined with a Varian Gemini 200 (200 MHz) spectrometer or Bruker AM-500 (500 MHz) spectrometer using tetramethylsilane as internal standard and all δ values were expressed in ppm.

The symbols used have the following meanings.

s: singlet, d: doublet, t: triplet, q: quartet, dt: double triplet, m: multiplet, br: broad, J: coupling constant.

Reference Example 1

Production of ethyl 2-amino-4-methyl-5-(4-methoxyphenyl) thiophene-3-carboxylate:

A mixture of 4-methoxyphenylacetone (16.5 g, 0.10 mol), ethyl cyanoacetate (12.2 g, 0.10 mol), ammonium acetate (1.55 g, 20 mmol), acetic acid (4.6 ml, 80 mmol), and benzene (20 ml) was refluxed for 24 hours, with the byproduct water being removed with a Dean-Stark trap. After cooling, the reaction mixture was concentrated under reduced pressure and the residue was distributed between dichloromethane and sodium hydrogen carbonate-water. The organic layer was washed with NaCl-water and dried ($MgSO_4$) and the solvent was distilled off under reduced pressure. The residue was dissolved in ethanol (30 ml), and sulfur (3.21 g, 0.10 mol) and diethylamine (10.4 ml, 0.10 mol) were added. This mixture was stirred at 50–60° C. for 2 hours and then concentrated and the residue was extracted with ethyl acetate. The extract was washed with NaCl-water and dried ($MgSO_4$) and the solvent was distilled off under reduced pressure. The residue was purified by silica gel column chromatography and crystallized from ether-hexane to provide light-yellow platelets (11.5 g, 40%). m.p. 79–80° C. Elemental analysis for $C_{15}H_{17}NO_3S$ C (%) H (%) N (%) S (%)
Calcd.: 61.83; 5.88; 4.81; 11.01
Found : 61.81; 5.75; 4.74; 10.82
$^1$H-NMR (200 MHz, $CDCl_3$) δ: 1.37 (3H, t, J=7.1 Hz), 2.28 (3H, s), 3.83 (3H, s), 4.31 (2H, q, J=7.1 Hz), 6.05 (2H, br s), 6.91 (2H, d, J=8.8 Hz), 7.27 (2H, d, J=8.8 Hz).
IR (KBr): 3426, 3328, 1651, 1586, 1550, 1505, 1485 $cm^{-1}$.
FAB-MS m/z: 291 ($M^+$).

Reference Example 2

(1) Production of ethyl 2,4(1H,3H)-dioxo-6-(4-methoxyphenyl) thieno[2,3-d]pyrimidine-3-acetate:

To a pyridine solution (30 ml) of the ethyl 2-amino-4-methyl-5-(4-methoxyphenyl) thiophene-3-carboxylate obtained in Reference Example 1 (8.00 g, 27.0 mmol) was added ethyl isocyanatoacetate (4.54 ml, 40.5 mmol) dropwise and the mixture was stirred at 50° C. for 2 hours. This reaction mixture was concentrated to dryness and the residue was distributed between ethyl acetate and ammonium chloride-water. The aqueous layer was extracted with ethyl acetate. The extracts were combined, washed with NaCl-water, and dried ($MgSO_4$) and the solvent was distilled off under reduced pressure. The residue was suspended in ethanol (100 ml) and following addition of potassium tert-butoxide (6.06 g, 54.0 mmol), the suspension was stirred at room temperature for 3 hours. To this reaction mixture was added 1N-HCl (50 ml) with ice-cooling and the ethanol was distilled off under reduced pressure. The resulting crystals were collected by filtration, rinsed with water-ethanol, and dried in vacuo over phosphorus pentoxide to provide white powders (11.0 g, 96%). For use as a sample for elemental analysis, the above powders were recrystallized from ethanol to provide colorless crystals. m.p. 164–165° C.

(2) Using ethyl 2-amino-4-methylthiophene-3-carboxylate, the procedure of Reference Example 2 (1) was repeated to provide ethyl 2,4(1H,3H)-dioxo-5-methylthieno[2,3-d]pyrimidine-3-acetate. Yield 94%, amorphous.

(3) To a solution of ethyl 2,4(1H,3H)-dioxo-5-methylthieno[2.3-d]pyrimidine-3-acetate obtained in the above item (2) in chloroform was added N-bromosuccinimide. Then the mixture was refluxed for 2 hours to provide ethyl 2,4(1H,3H)-dioxo-5-methyl-6-bromothieno[2,3-d]pyrimidine-3-acetate. Yield 86%, amorphous.

Reference Example 3

Production of ethyl 2,4(1H,3H)-dioxo-6-(4-hydroxyphenyl)-5-methylthieno[2,3-d]pyrimidine-3-acetate:

To an ice-cooled mixture of aluminum chloride (2.90 g, 21.7 mmol), methyl disulfide (2.45 ml, 27.2 mmol), and dichloromethane (60 ml) was added a solution of the compound obtained in Reference Example 2 (2.0 g, 5.34 mmol) in dichloromethane (40 ml) dropwise and the mixture was stirred at room temperature for 20 hours. The reaction mixture was then poured in ice-water and the dichloromethane was distilled off under reduced pressure. This suspension was extracted with ethyl acetate and the extract was washed with NaCl-water and dried ($MgSO_4$). The solvent was then distilled off under reduced pressure and the residue was purified by silica gel column chromatography to provide white powders (1.64 g, 85%). For use as a sample for elemental analysis, the powders were recrystallized from ethyl acetate to provide colorless crystals. m.p. 240–242° C. Elemental analysis for $C_{17}H_{16}N_2O_5S \cdot 0.1H_2O$ C (%) H (%) N (%)
Calcd.: 56.38; 4.51; 7.73
Found : 56.28; 4.48; 7.64
$^1$H-NMR (200 MHz, DMSO-$d_6$) δ: 1.22 (3H, t, J=7.1 Hz), 2.37 (3H, s), 4.15 (2H, q, J=7.1 Hz), 4.59 (2H, s), 6.85 (2H, d, J=8.6 Hz), 7.26 (2H, d, J=8.6 Hz), 9.73 (1H, s), 12.39 (1H, s).
IR (KBr): 3356, 2992, 1720, 1690, 1667, 1611, 1593, 1568, 1537, 1502 $cm^{-1}$.

Reference Example 4

Production of ethyl 2,4(1H,3H)-dioxo-6-(4-hydroxyphenyl)-1-(2-methylthiobenzyl)-5-methylthieno[2,3-d]-pyrimidine-3-acetate:

To a solution of the compound obtained in Reference Example 3 (0.60 g, 1.66 mmol) in pyridine (8 ml) was added acetic anhydride (3 ml, 31.8 mmol) and the mixture was stirred at room temperature for 3 hours. This reaction mixture was concentrated and the residue was distributed between ethyl acetate and diluted hydrochloric acid. The aqueous layer was extracted with ethyl acetate. The organic layers were combined, washed with NaCl-water, and dried ($MgSO_4$) and the solvent was distilled off under reduced pressure. The residue was purified by silica gel column chromatography to provide a white amorphous solid (0.57 g). To a solution of this amorphous solid in dimethylformamide (5 ml) were added potassium carbonate (0.38 g, 2.75 mmol) and 2-methylthiobenzyl chloride (0.65 g, 4.15 mmol) and the mixture was stirred at room temperature for 22 hours. This reaction mixture was concentrated and the residue was distributed between ethyl acetate and NaCl-water. The aqueous layer was extracted with ethyl acetate. The organic layers were combined, washed with NaCl-water, and dried ($MgSO_4$) and the solvent was distilled off under reduced pressure. The residue was purified by silica gel column chromatography to provide a white amorphous solid (0.60 g). This amorphous solid was dissolved in methanol (18 ml)-tetrahydrofuran (12 ml) and a solution of potassium carbonate (0.313 g, 2.26 mmol) in water (8 ml) was added dropwise. The mixture was stirred at room temperature for 30 minutes and after 1N-hydrochloric acid (5 ml) was added under ice-cooling, the mixture was extracted with ethyl acetate. The extract was washed with NaCl-water and dried ($MgSO_4$), and the solvent was distilled off under reduced pressure. The residue was crystallized from ether to provide colorless crystals (4.33 g, 78%). m.p. 177–178° C. Elemental analysis for $C_{25}H_{24}N_2O_5S_2 \cdot 1/10H_2O$ C (%) H (%) N (%)
Calcd.: 60.25; 4.89; 5.62
Found : 60.09; 4.66; 5.57

$^1$H-NMR (200 MHz, CDCl$_3$) δ: 1.32 (3H, t, J=7.2 Hz), 2.45 (3H, s), 2.52 (3H, s), 4.28 (2H, q, J=7.2 Hz), 4.87 (2H, s), 5.28 (2H, s), 5.75 (1H, s), 6.78 (2H, d, J=8.6 Hz), 6.97–7.14 (4H, m), 7.21–7.34 (2H, m).

IR (KBr): 3346, 2978, 1752, 1700, 1651, 1613, 1591, 1564, 1535, 1481 cm$^{-1}$.

Reference Example 5

(1) Using the compound obtained in Reference Example 3, the procedure of Reference Example 4 was repeated except that 2-chloro-6-fluorobenzyl chloride was used in lieu of 2-methylthiobenzyl chloride to provide ethyl 2,4(1H,3H)-dioxo-6-(4-hydroxyphenyl)-1-(2-chloro-6-fluorobenzyl)-5-methylthieno[2,3-d]pyrimidine-3-acetate. Yield 59%, amorphous.

(2) Using the compound obtained in Reference Example 2 (3), the procedure of Reference Example 4 was repeated to provide ethyl 2,4(1H,3H)-dioxo-1-(2-methylthiobenzyl)-5-methylthieno[2,3-d]pyrimidine-3-acetate. Yield 87%, amorphous.

Reference Example 6

Production of ethyl 2,4(1H,3H)-dioxo-6-(4-methoxymethoxyphenyl)-1-(2-methylthiobenzyl)-5-methylthieno[2,3-d]pyrimidine-3-acetate:

To a suspension of sodium hydride (60% in oil, 500 mg, 12.5 mmol) in dimethylformamide (20 ml) was added a solution of the compound obtained in Reference Example 4 (2.0 g, 3.7 mmol) in dimethylformamide (30 ml) dropwise in a nitrogen gas stream under ice-cooling. The mixture was stirred at the same temperature for 30 minutes and, then, chloromethyl methyl ether (1.0 g, 12.4 mmol) was added dropwise. This mixture was stirred at room temperature for 16 hours and then concentrated, and the residue was distributed between ethyl acetate and aqueous ammonium chloride solution. The aqueous layer was extracted with ethyl acetate. The extracts were combined, washed with NaCl-water, and dried (MgSO$_4$) and the solvent was distilled off under reduced pressure. The residue was purified by silica gel column chromatography and recrystallized from ethyl acetate-hexane to provide colorless crystals (1.05 g, 59%). m.p. 133–134° C. Elemental analysis for C$_{27}$H$_{28}$N$_2$O$_6$S C (%) H (%) N (%)
Calcd.: 63.76; 5.55; 5.51
Found : 63.48; 5.62; 5.37

$^1$H-NMR (300 MHz, CDCl$_3$) δ: 1.30 (3H, t, J=7.1 Hz), 1.43 (3H, t, J=7.0 Hz), 2.49 (3H, s), 3.87 (3H, s), 4.05 (2H, q, J=7.0 Hz), 4.25 (2H, q, J=7.1 Hz), 4.83 (2H, s), 5.24 (2H, s), 6.86–6.94 (4H, m), 7.09–7.14 (1H, m), 7.22–7.31 (3H, m).

IR (KBr): 2984, 1758, 1707, 1665, 1607, 1562, 1535, 1477 cm$^{-1}$.

Reference Example 7

The compound obtained in Reference Example 5 was reacted with 2-chloro-6-fluorobenzyl chloride in lieu of chloromethyl methyl ether to provide ethyl 2,4(1H,3H)-dioxo-6-(4-isobutoxyphenyl)-1-(2-chloro-6-fluorobenzyl)-5-methylthieno[2,3-d]pyrimidine-3-acetate. Yield 29%, amorphous.

Reference Example 8

Production of ethyl 2,4(1H,3H)-dioxo-5-bromomethyl-1-(2-methylthiobenzyl)-6-(4-methoxymethoxyphenyl)thieno[2,3-d]pyrimidine-3-acetate:

A mixture of the compound obtained in Reference Example 6 (1.20 g, 2.22 mmol), N-bromosuccinimide (0.4 g, 2.25 mmol), α,α'-azobisisobutyronitrile (50 mg), and carbon tetrachloride (50 ml) was refluxed for 4 hours. After cooling, the insolubles were filtered off and the filtrate was diluted with dichloromethane. The organic layer was washed with NaCl-water and dried (MgSO$_4$) and the solvent was distilled off under reduced pressure to provide a yellow amorphous solid (2.0 g).

$^1$H-NMR (300 MHz, CDCl$_3$) δ: 1.28 (3H, t, J=7.2 Hz), 2.53 (3H, s), 3.50 (3H, s), 4.26 (2H, q, J=7.2 Hz), 4.80 (2H, s), 4.89 (2H, s), 5.22 (2H, s), 5.36 (2H, s), 7.00–7.50 (8H, m).

Reference Example 9

Production of ethyl 2,4(1H,3H)-dioxo-6-(4-methoxyphenyl)-1-(2-methylthiobenzyl)-5-methylthieno[2,3-d]-pyrimidine-3-acetate:

To a solution of the compound obtained in Reference Example 2 (2.0 g, 5.35 mmol) in dimethylformamide (25 ml) were added potassium carbonate (1.1 g, 7.98 mmol), potassium iodide (catalyst amount), and 2-methylthiobenzyl chloride (1.2 g, 6.96 mmol) and the mixture was stirred at room temperature for 18 hours. This reaction mixture was concentrated and the residue was distributed between ethyl acetate and NaCl-water. The aqueous layer was extracted with ethyl acetate. The organic layers were combined, washed with NaCl-water, and dried (MgSO$_4$) and the solvent was distilled off under reduced pressure. The residue was purified by silica gel column chromatography to provide a light-yellow amorphous solid (1.8 g, 66%). Recrystallization from ether gave colorless crystals. m.p. 144–145° C.

Reference Example 10

Starting with the compound obtained in Reference Example 2, the procedure of Reference Example 9 was otherwise repeated to provide ethyl 2,4(1H,3H)-dioxo-6-(4-methoxyphenyl)-1-(2-chloro-6-fluorobenzyl)-5-methylthieno[2,3-d]pyrimidine-3-acetate. Yield 95%, amorphous.

Reference Example 11

Starting with the compounds obtained in Reference Examples 9 and 10, respectively, the procedure of Reference Example 8 was repeated to provide the following compounds. Compound 1: Ethyl 2,4(1H,3H)-dioxo-6-(4-methoxyphenyl)-1-(2-methylthiobenzyl)-5-bromomethylthieno[2,3-d]pyrimidine-3-acetate. Yield 95%, amorphous. Compound 2: Ethyl 2,4(1H,3H)-dioxo-6-(4-methoxyphenyl)-1-(2-chloro-6-fluorobenzyl)-5-bromomethylthieno[2,3-d]pyrimidine-3-acetate. Yield 100%, amorphous. Compound 3: Ethyl 2,4(1H,3H)-dioxo-6-(4-isobutoxyphenyl)-1-(2-chloro-6-fluorobenzyl)-5-bromomethylthieno[2,3-d]pyrimidine-3-acetate. Yield 60%, amorphous.

Reference Example 12

In accordance with the similar manner of Reference Examples 6 and 8 the following compounds were obtained.
Compound 1: Ethyl 2,4(1H,3H)-dioxo-5-bromomethyl-1-(2-methylthiobenzyl)-6-(4-propoxyphenyl)thieno[2,3-d]pyrimidine-3-acetate. amorphous.

Reference Example 13

Production of ethyl {2,4(1H,3H)-dioxo-5-methyl-1-(2-methylthiobenzyl)-6-(4-(2-methoxyethyl)phenyl)-thieno[2,3-d]pyrimidine-3-acetate:

To a mixture of ethyl {2,4(1H,3H)-dioxo-6-bromo-5-methyl-1-(2-methylthiobenzyl)thieno[2,3-d]pyrimidine-3-acetate (1.0 g, 2.07 mmol) obtained in Reference Example 5(2), 4-(methoxyethylphenyl)boronic acid (1.0 g, 5.56 mmol), and 2M sodium carbonate (5.2 ml, 10.4 mmol) in 1,2-dimethoxyethane (50 ml) was added Pd(PPh$_3$)$_4$(Ph denotes phenyl) (358 mg, 0.31 mmol) under argon atmosphere. The mixture was stirred under reflux for 5 hour and filtered through celite. The filterate was partitioned between ethyl acetate and brine. The aqueous phase was separated and extracted with ethyl acetate. The combined extracts were washed with brine, dried over MgSO$_4$ and concentrated in vacuo. The residue was chromatographed on silica gel with ethyl acetate and n-hexane (1:5–1:3) to give the product (860 mg, 77%) as colorless amorphous solid. Recrystallization from ethyl acetate and nhexane gave product (594 mg) as colorless powder, m.p. 126–128° C.

Reference Example 14

Production of ethyl 2,4(1H,3H)-dioxo-5-bromomethyl-1-(2-methylthiobenzyl)-6-(4-(2-methoxyethyl)phenyl)thieno[2,3-d]pyrimidine-3-acetate:

A mixture of ethyl 2,4(1H,3H)-dioxo-5-methyl-1-(2-methylthiobenzyl)-6-(4-(2-methoxyethyl)phenyl)thieno[2,3-d]pyrimidine-3-acetate (600 mg, 1.11 mmol) obtained in Reference Example 13, N-bromosuccinimide (198 mg, 1.11 mmol) and 2,2'-azobisisobutyronitrile (18 mg, 0.11 mmol) in chloroform (30 ml) was stirred under reflux for 1.5 hour. The mixture was partitioned between CH$_2$Cl$_2$+brine. The organic layer was separated and washed with brine, dried over MgSO$_4$ and concentrated in vacuo to afford a pale yellow amorphous (730 mg, 44% purity).

Reference Example 15

Production of ethyl 2,4(1H,3H)-dioxo-6-(4-methoxyphenyl)-1-(2-methylthiobenzyl)-5-(cyanomethyl)thieno[2,3-d]pyrimidine-3-acetate:

In dimethyl sulfoxide (DMSO) (3 ml) was dissolved the compound obtained in Reference Example 11 (1) (0.67 g, 1.0 mmol) followed by addition of sodium cyanide (50 mg, 1.0 mmol) and the mixture was stirred at 60° C. for 6 hours. After cooling, this reaction mixture was poured in iced water (100 ml) and extracted with ethyl acetate (50 ml) and methylene chloride (100 ml, twice). The extracts were pooled, washed with NaCl-water, and dried (MgSO$_4$) and the solvent was distilled off under reduced pressure. The residue was purified by silica gel column chromatography to provide a light-yellow amorphous solid (0.20 g, 38%).

$^1$H-NMR (300 MHz, CDCl$_3$) δ: 1.33 (3H, t, J=7.1 Hz), 2.52 (3H, s), 3.82 (3H, s), 3.94 (2H, s), 4.25 (2H, q, J=7.1 Hz), 4.88 (2H, s), 5.38 (2H, s), 6.95 (2H, d), 7.05 (1H, d), 7.17 (1H, t), 7.34 (2H, d), 7.20–7.40 (2H, m).

IR (KBr): 2978, 2254, 1676, 1607, 1568, 1539, 1483, 1257 cm$^{-1}$.

The compounds shown in the above Reference Examples are listed in the Table 1.

TABLE 1

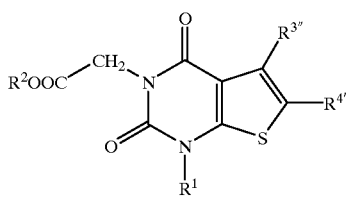

| Reference Example No. | R$^1$ | R$^2$ | R$^{3"}$ | R$^{4'}$ |
|---|---|---|---|---|
| 2(1) | H | ethyl | H | methoxyphenyl |
| 2(2) | H | ethyl | methyl | H |
| 2(3) | H | ethyl | methyl | bromo |
| 3 | H | ethyl | methyl | 4-hydroxyphenyl |
| 4 | 2-methylthio-benzyl | ethyl | methyl | 4-hydroxyphenyl |
| 5(1) | 2-chloro-6-fluorobenzyl | ethyl | methyl | 4-hydroxyphenyl |

TABLE 1-continued

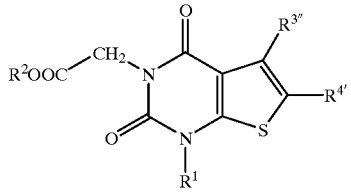

| Reference Example No. | R$^1$ | R$^2$ | R$^{3"}$ | R$^{4'}$ |
|---|---|---|---|---|
| 5(2) | 2-methylthio-benzyl | ethyl | methyl | bromo |
| 6 | 2-methylthio-benzyl | ethyl | methyl | 4-methoxy-methoxyphenyl |
| 7 | 2-chloro-6-fluorobenzyl | ethyl | methyl | 4-isobutoxyphenyl |
| 8 | 2-methylthio-benzyl | ethyl | bromomethyl | 4-methoxy-methoxyphenyl |
| 9 | 2-methylthio-benzyl | ethyl | methyl | 4-methoxyphenyl |
| 10 | 2-chloro-6-fluorobenzyl | ethyl | methyl | 4-methoxyphenyl |
| 11(1) | 2-methylthio-benzyl | ethyl | bromomethyl | 4-methoxyphenyl |
| 11(2) | 2-chloro-6-fluorobenzyl | ethyl | bromomethyl | 4-methoxyphenyl |
| 11(3) | 2-chloro-6-fluorobenzyl | ethyl | bromomethyl | 4-isobutoxyphenyl |
| 12 | 2-methylthio-benzyl | ethyl | bromomethyl | 4-propoxyphenyl |
| 13 | 2-methylthio-benzyl | ethyl | methyl | 4-(2-methoxyethyl)-phenyl |
| 14 | 2-methylthio-benzyl | ethyl | bromomethyl | 4-(2-methoxyethyl)-phenyl |
| 15 | 2-methylthio-benzyl | ethyl | cyanomethyl | 4-methoxyphenyl |

EXAMPLE 1

Production of ethyl 2,4(1H,3H)-dioxo-6-(4-methoxyyphenyl)-1-(2-methylthiobenzyl)-5-(methanesulfonethyl)thieno[2,3-d]pyrimidine-3-acetate:

To a suspension of sodium hydride (60% in oil; 60 mg, 1.5 mmol) in dimethylformamide (10 ml) was added the compound obtained in Reference Example 8 (0.6 g, 1.0 mmol) as well as methanesulfonamide (0.11 g, 1.2 mmol). The mixture was stirred at room temperature for 16 hours, at the end of which time it was concentrated. The residue was distributed between ethyl acetate and aqueous ammonium chloride solution and the aqueous layer was extracted with ethyl acetate. The extracts were combined, washed with NaCl-water, and dried (MgSO$_4$), and the solvent was distilled off under reduced pressure. The residue was purified by silica gel column chromatography to provide a light-yellow amorphous solid (0.36 g, 59%).

$^1$H-NMR (300 MHz, CDCl$_3$) δ: 1.33 (3H, t, J=7.1 Hz), 2.53 (3H, s), 2.88 (3H, s), 3.48 (3H, s), 4.28 (2H, q, J=7.1 Hz), 4.37 (2H, d, J=6.3 Hz), 4.85 (2H, s), 5.19 (2H, s), 5.36 (2H, s), 6.07 (1H, t), 7.0–7.20 (4H, m), 7.25–7.40 (4H, m).

EXAMPLE 2

Production of ethyl 2,4(1H,3H)-dioxo-6-(4-methoxy-methoxyphenyl)-1-(2-methylthiobenzyl)-5-(benzenesulfonamidomethyl)thieno[2,3-d]pyrimidine-3-acetate:

The compound obtained in Reference Example 8 (0.6 g) was reacted with benzenesulfonamide in lieu of methanesulfonamide in otherwise the same manner as Example 1 to provide a light-yellow amorphous solid (0.56 g, 83%).

$^1$H-NMR (300 MHz, CDCl$_3$) δ: 1.34 (3H, t, J=7.1 Hz), 2.52 (3H, s), 3.50 (3H, s), 4.30 (2H, q, J=7.1 Hz), 4.27 (2H, m), 4.82 (2H, s), 5.21 (2H, s), 5.26 (2H, s), 6.63 (1H, t), 6.97 (1H, d), 7.08 (2H, d), 7.17 (1H, dt), 7.25–7.45 (6H, m), 7.51 (1H, t), 7.66 (2H, dd), 7.94 (1H, d).

EXAMPLE 3

Using the compound obtained in Reference Example 8, 11, 12, 13 and 14, the similar procedure as in Example 1 was otherwise repeated to provide the following compounds. Compound 1: Ethyl 2,4(1H,3H)-dioxo-6-(4-methoxyphenyl)-1-(2-methylthiobenzyl)-5-(methanesulfonamidomethyl)thieno[2,3-d]pyrimidine-3-acetate. Yield 91%, amorphous. Compound 2: Ethyl 2,4(1H,3H)-dioxo-6-(4-methoxyphenyl)-1-(2-chloro-6-fluorobenzyl)-5-(methanesulfonamidomethyl)thieno[2,3-d]pyrimidine-3-acetate. Yield 33%, amorphous. Compound 3: Ethyl 2,4(1H,3H)-dioxo-6-(4-isobutoxyphenyl)-1-(2-chloro-6-fluorobenzyl)-5-(methanesulfonamidomethyl)thieno[2,3-d]pyrimidine-3-acetate. Yield 29%, amorphous. Compound 4: Ethyl 2,4(1H,3H)-dioxo-6-(4-propoxyphenyl)-1-(2-methylthiobenzyl)-5-(methanesulfonamidomethyl)thieno[2,3-d]pyrimidine-3-acetate. Yield 85%, amorphous. Compound 5: Ethyl 2,4(1H,3H)-dioxo-6-(4-methoxymethoxy phenyl)-1-(2-methylthiobenzyl)-5-(ethanesulfonamidomethyl)thieno[2,3-d]pyrimidine-3-acetate. Yield 89%, m.p. 153–155° C. Compound 6: Ethyl 2,4(1H,3H)-dioxo-6-(4-methoxymethoxy phenyl)-1-(2-methylthiobenzyl)-5-(propanesulfonamidomethyl)thieno[2,3-d]pyrimidine-3-acetate. Yield 85%, m.p. 122–123° C. Compound 7: Ethyl 2,4(1H,3H)-dioxo-6-(4-propoxyphenyl)-1-(2-methylthiobenzyl)-5-(isopropanesulfonamidomethyl)thieno[2,3-d]pyrimidine-3-acetate. Yield 60%, amorphous. Compound 8: Ethyl 2,4(1H,3H)-dioxo-6-(4-methoxymethoxy phenyl)-1-(2-methylthiobenzyl)-5-(trifluoromethanesulfonamidomethyl)thieno[2,3-d]pyrimidine-3-acetate. Yield 58%, amorphous. Compound 9: Ethyl 2,4(1H,3H)-dioxo-6-(4-methoxymethoxy phenyl)-1-(2-methylthiobenzyl)-5-(isopropanesulfonamidomethyl)thieno[2,3-d]pyrimidine-3-acetate. Yield 93%, amorphous. Compound 10: Ethyl 2,4(1H,3H)-dioxo-6-(4-propoxyphenyl)-1-(2-methylthiobenzyl)-5-(ethanesulfonamidomethyl)thieno[2,3-d]pyrimidine-3-acetate. Yield 84%, m.p. 132–134° C. Compound 11: Ethyl 2,4(1H,3H)-dioxo-6-(4-(2-methoxyethyl)phenyl)-1-(2-methylthiobenzyl)-5-(methanesulfonamidomethyl)thieno[2,3-d]pyrimidine-3-acetate. Yield 59%, m.p. 131–134° C.

EXAMPLE 4

Production of ethyl 2,4(1H,3H)-dioxo-6-(4-methoxyphenyl)-1-(2-methylthiobenzyl)-5-(ethoxycarbonylmethyl)thieno[2,3-d]pyrimidine-3-acetate:

The compound obtained in Reference Example 15 (0.11 g, 0.21 mmol) was dissolved in ethanol (20 ml) followed by addition of saturated HCl-ethanol (10.5N) (4 ml) and the mixture was refluxed for 48 hours. After cooling, the reaction mixture was distributed between ethyl acetate (50 ml) and saturated NaHCO$_3$-water (30 ml). The aqueous layer was re-extracted with ethyl acetate (30 ml). The extracts were combined, washed with NaCl-water, and dried (MgSO$_4$) and the solvent was distilled off under reduced pressure. The residue was crystallized from methanol to provide colorless crystals (0.10 g, 84%). m.p. 117–118° C. Elemental analysis for C$_{29}$H$_{30}$N$_2$O$_7$S·1/2H$_2$O

C (%) H (%) N (%)

Calcd.: 58.87; 5.28; 4.73

Found : 58.97; 5.25; 4.65

$^1$H-NMR (300 MHz, CDCl$_3$) δ: 1.27 (3H, t, J=7.1 Hz), 1.29 (3H, t, J=7.1 Hz), 2.53 (3H, s), 3.82 (3H, s), 3.84 (2H, d), 4.19 (2H, q, J=7.0 Hz), 4.22 (2H, q, J=7.1 Hz), 4.82 (2H, s), 5.34 (2H, s), 6.89 (2H, d), 7.05 (1H, d), 7.15 (1H, t), 7.25 (2H, d), 7.32 (2H, t).

EXAMPLE 5

Production of 2,4(1H,3H)-dioxo-6-(4-methoxymethoxyphenyl)-1-(2-methylthiobenzyl)-5-(methanesulfonamidomethyl)thieno[2,3-d]pyrimidine-3-aretic acid:

The compound obtained in Example 1 (0.5 g, 0.83 mmol) was dissolved in tetrahydrofuran (10 ml)-methanol (2 ml) followed by addition of 1N-sodium hydroxide-water (2 ml). This mixture was stirred at room temperature for 4 hours, after which 1N hydrochloric acid solution (2 ml) was added. The mixture was then concentrated and the residue was distributed between ethyl acetate and aqueous ammonium chloride solution. The aqueous layer was extracted with ethyl acetate. The extracts were combined, washed with NaCl-water, and dried (MgSO$_4$) and the solvent was distilled off under reduced pressure. The residue was purified by silica gel column chromatography to give a light-yellow solid (0.55 g). This product was recrystallized from ethyl acetate-isopropyl ether to provide light-yellow crystals (0.40 g, 76%). m.p. 208–209° C. Elemental analysis for C$_{26}$H$_{27}$N$_3$O$_8$S$_3$·1/2H$_2$O

C (%) H (%) N (%)

Calcd.: 50.80; 4.59; 6.83

Found : 50.75; 4.53; 6.79

$^1$H-NMR (300 MHz, DMSO) δ: 2.55 (3H, s), 2.87 (3H, s), 3.41 (3H, s), 4.30 (2H, s), 4.41 (2H, s), 5.21 (2H, s), 5.24 (2H, s), 6.91 (1H, t), 7.02 (1H, d), 7.11 (2H, d), 7.15 (1H, d), 7.33 (1H, t), 7.42 (2H, d).

EXAMPLE 6

Production of ethyl 2,4(1H,3H)-dioxo-6-(4-isobutoxyphenyl)-1-(2-methylthiobenzyl)-5-(methanesulfonamidomethyl)thieno[2,3-d]pyrimidine-3-acetate:

To a solution of ethyl 2,4(1H,3H)-dioxo-6-(4-hydroxyphenyl)-1-(2-methylthiobenzyl)-5-(methanesulfonamidomethyl)thieno[2,3-d]pyrimidine-3-acetate (0.30 g), which was synthesized from ethyl 2,4(1H,3H)-dioxo-6-(4-methoxymethoxyphenyl)-1-(2-methylthiobenzyl)-5-(methanesulfonamidomethyl)thieno[2,3-d]pyrimidine-3-acetate (which was obtained in Example 1) with 1N hydrochloric acid in tetrahydrofuran at room temperature for 3 hours, in dimethylformamide (DMF) (25 ml) was added isobutyliodide (0.30 g) and K$_2$CO$_3$ (0.3 g). The mixture was stirred at room temperature for 24 hours. Then the mixture was evaporated in vacuo to give the residue, which was partitioned between ethyl acetate (50 ml) and aq.NH$_4$Cl (30 ml). The organic solution was dried with Na$_2$SO$_4$ and evaporated in vacuo to give a yellow amorphous, which was chromatographed on silica gel to provide a yellow amorphous (0.11 g, 33%).

EXAMPLE 7

Using the compounds obtained in Example 1, the similar procedure as in Example 6 is repeated to provide the following compounds: Compound 1: Ethyl 2,4(1H,3H)- dioxo-6-(4-carboxymethoxyphenyl)-1-(2-methylthiobenzyl)-5-(methanesulfonamidomethyl)thieno[2,3-d]pyrimidine-3-acetate. Yield 70%, amorphous. Compound 2: Ethyl 2,4(1H,3H)-dioxo-6-(4-allyloxyphenyl)-1-(2-methylthiobenzyl)-5-(methanesulfonamidomethyl)thieno[2,3-d]pyrimidine-3-acetate. Yield 84%, amorphous. Compound 3: Ethyl 2,4(1H,3H)-dioxo-6-(4-butoxyphenyl)-1-(2-methylthiobenzyl)-5-(methanesulfonamidomethyl)thieno[2,3-d]pyrimidine-3-acetate. Yield 82%, amorphous. Compound 4: Ethyl 2,4(1H,3H)-dioxo-5-[4-(2,2,2-trifluoroethoxyphanyl)]-1-(2-methylthiobenzyl)-5-(methanesulfonamidomethyl)thieno(2,3-d)pyrimidine-3-acetate.

EXAMPLE 8

Production of ethyl 2,4(1H,3H)-dioxo-6-(4-methylamino carbonylmethoxyphenyl)-1-(2-methylthiobenzyl)-5-(methanesulfonamidomethyl)thieno [2,3-d]pyrimidine-3-acetate:

The compound 1 obtained in Example 7 was reacted with isobutylchloroformate and triethylamine in tetrahydrofuran (THF) at 0° C. for three hours to provide acid anhydride compound, which was converted to amide derivative with methylamine. Yield 100%, amorphous.

EXAMPLE 9

Using the compounds obtained in Example 7, the procedure as in Example 8 was repeated to produce the following compounds: Compound 1: Ethyl 2,4(1H,3H)-dioxo-6-(4-propylaminocarbonylmethoxyphenyl)-1-(2-methylthiobenzyl)-5-(methanesulfonamidomethyl)thieno[2,3-d]pyrimidine-3-acetate. Yield 95%, amorphous. Compound 2: Ethyl 2,4(1H,3H)-dioxo-6-(4-piperazinecarbonylmethoxyphenyl)-1-(2-methylthiobenzyl)-5-(methanesulfonamidomethyl)thieno[2,3-d]pyrimidine-3-acetate. Yield 66%, amorphous.

EXAMPLE 10

(1) Production of pivaloyloxymethyl 2,4(1H,3H)-dioxo-6-(4-methoxymethoxyphenyl)-1-(2-methylthiobenzyl)-5-(methanesulfonamidomethyl)-thieno[2,3-d]pyrimidine-3-acetate:

To an ice-cooled mixture of 2,4(1H,3H)-dioxo-5-methanesulfonamidomethyl-6-(4-methoxymethoxyphenyl)-1-(2-methylthiobenzyl)thieno[2,3-d]pyrimidine-3-acetic acid obtained in Example 5 (0.25 g, 0.413 mmol), K$_2$CO$_3$ (86 mg, 0.622 mmol) and KI (83 mg, 0.50 mmol) in DMF (8 ml) was added dropwise chloromethyl pivalate (72 ml, 0.50 mmol). After being stirred at 0° C. to room temperature for 22 hours, the mixture was concentrated in vacuo and the residue was partitioned between ethyl acetate and brine. The aqueous phase was separated and extracted with ethyl acetate. The combined extracts were washed with brine, dried over MgSO$_4$, and concentrated in vacuo. The residue was subjected to silica gel column chromatography by eluting with ethyl acetate-hexane (4:6–1:1) to give the product (0.24 g, 80.8%) as a colorless syrup.

Crystallization from ethyl acetate-ether-hexane afforded the product (0.203 g, 72.6%) as white crystals. Yield 81%, m.p. 74–77° C.

(2) Employing the compound produced in Example 5 as the starting material, in accordance with substantially the same procedure as described the above item (1) of Example 10, the following compound is produced. (R.S)-1-(cyclohexyloxycarbonyloxy)ethyl 2,4(1H,3H)-dioxo-6-(4-methoxymethoxyphenyl)-1-(2-methylthiobenzyl)-5-(methanesulfonamidomethyl)thieno [2,3-d]pyrimidine-3-acetate

EXAMPLE 11

Using the compounds obtained in Examples 2, 3, 4, 6, 7, 8 or 9, the procedure of Example 5 is otherwise repeated to provide the following compounds.

Compound 1: 2,4(1H,3H)-Dioxo-6-(4-methoxymethoxyphenyl)-1-(2-methylthiobenzyl)-5-(benzenesulfonamidomethyl)thieno[2,3-d]pyrimidine-3-acetic acid. Yield 68%, m.p. 120–125° C. Compound 2: 2,4(1H,3H)-Dioxo-6-(4-methoxyphenyl)-1-(2-methylthiobenzyl)-5-(methanesulfonamidomethyl)-thieno[2,3-d]pyrimidine-3-acetic acid. Yield 76%, m.p. 208–209° C. Compound 3: Ethyl 2, 4(1H,3H)-dioxo-6-(4-methoxyphenyl)-1-(2-methylthiobenzyl)-5-(carboxylmethyl)thieno[2,3-d]-pyrimidine-3-acetate. Yield 65%, m.p. 243–245° C. Compound 4: 2,4(1H,3H)-Dioxo-6-(4-methoxyphenyl)-1-(2-chloro-6-fluorobenzyl)-5-(methanesulfonamidomethyl)-thieno[2,3-d]pyrimidine-3-acetic acid. Yield 57%, amorphous. Compound 5: 2,4(1H,3H)-Dioxo-6-(4-isobutoxyphenyl)-1-(2-chloro-6-fluorobenzyl)-5-(methanesulfonamidomethyl)-thieno[2,3-d]pyrimidine-3-acetic acid. Yield 30%, m.p. amorphous. Compound 6: 2,4(1H,3H)-Dioxo-6-(4-isobutoxyphenyl)-1-(2-methylthiobenzyl)-5-(methanesulfonamidomethyl)-thieno[2,3-d]pyrimidine-3-acetic acid. Compound 7: 2,4(1H,3H)-Dioxo-6-(4-propoxyphenyl)-1-(2-methylthiobenzyl)-5-(methanesulfonamidomethyl)-thieno[2,3-d]pyrimidine-3-acetic acid. Yield 84%, amorphous. Compound 8: 2,4(1H,3H)-Dioxo-6-(4-butoxyphenyl)-1-(2-methylthiobenzyl)-5-(methanesulfonamidomethyl)-thieno[2,3-d]pyrimidine-3-acetic acid. Yield 85%, amorphous. Compound 9: 2,4(1H, 3H)-Dioxo-6-(4-propoxyphenyl)-1-(2-methylthiobenzyl)-5-(ethanesulfonamidomethyl)-thieno [2,3-d]pyrimidine-3-acetic acid. amorphous. Compound 10: 2,4(1H,3H)-Dioxo-6-(4-(2-methoxyethyl)phenyl)-1-(2-methylthiobenzyl)-5-(methanesulfonamidomethyl)thieno[2,3-d]pyrimidine-3-acetic acid. Yield 73%, m.p. 167–168° C. Compound 11: 2,4(1H,3H)-Dioxo-6-(4-methoxymethoxy phenyl)-1-(2-methylthiobenzyl)-5-(isopropanesulfonamidomethyl)thieno[2,3-d]pyrimidine-3-acetic acid. Yield 64%, m.p. 112–114° C. Compound 12: 2,4(1H,3H)-Dioxo-6-(4-methylaminocarbonyl-methoxyphenyl)-1-(2-methylthiobenzyl)-5-(methanesulfonamidomethyl)thieno[2,3-d]pyrimidine-3-acetic acid. Yield 58%, amorphous. Compound 13: 2,4(1H,3H)-Dioxo-6-(4-propylamino carbonylmethoxyphenyl)-1-(2-methylthiobenzyl)-5-(methanesulfonamidomethyl)thieno[2,3-d]pyrimidine-3-acetic acid. Yield 81%, amorphous. Compound 14: 2,4(1H,3H)-Dioxo-6-(4-piperazine carbonylmethoxyphenyl)-1-(2-methylthiobenzyl)-5-(methanesulfonamidomethyl)thieno[2,3-d]pyrimidine-3-acetic acid. Yield 84%, amorphous. Compound 15: 2,4(1H,3H)-Dioxo-6-(4-propoxyphenyl)-1-(2-methylthiobenzyl)-5-(isopropanesulfonamidomethyl)-thieno[2,3-d]pyrimidine-3-acetic acid. Yield 84%, amorphous. Compound 16: 2,4(1H,3H)-Dioxo-6-(4-methoxymethoxyphenyl)-1-(2-methylthiobenzyl)-5-(ethanesulfonamidomethyl)thieno[2,3-d]pyrimidine-3-acetic acid. Yield 80%, m.p. 125–128° C. Elemental analysis for C$_{27}$H$_{29}$N$_3$O$_8$S$_3$·1.0H$_2$O
C (%) H (%) N (%)

Calcd.: 50.85; 4.90; 6.59
Found : 51.15; 4.78; 6.54

$^1$H-NMR (300 MHz, CDCl$_3$) δ: 1.33 (3H, t, J=7.4 Hz), 2.53 (3H, s), 2.96 (2H, q, J=7.4 Hz), 3.48 (3H, s), 4.35 (2H, d, J=6.6Hz), 4.92 (2H, s), 5.19 (2H, s), 5.36 (2H, s), 6.05 (1H, t, J=6.6 Hz), 7.01–7.37 (8H, m).

IR (KBr): 1702, 1649, 1543, 1487 cm$^{-1}$

Mass spectrum: 620.1 (MH$^+$) Compound 17: Ethyl 2,4(1H,3H)-dioxo-6-(4-methoxymethoxyphenyl)-1-(2-methylthiobenzyl)-5-(propanesulfonamidomethyl)thieno[2,3-d]pyrimidine-3-acetic acid. Yield 93%, m.p. 123–124° C. Compound 18: Ethyl 2,4(1H,3H)-dioxo-6-(4-methoxymethoxyphenyl)-1-(2-methylthiobenzyl)-5-(trifluoromethanesulfonamidomethyl)thieno[2,3-d]pyrimidine-3-acetic acid. Yield 52%, amorphous. Compound 19: 2,4(1H,3H)-Dioxo-6-[4-(2,2,2-trifluoroethoxyphenyl)]-1-(2-methylthiobenzyl)-5-(methanesulfonamidomethyl)thieno[2,3-d]pyrimidine-3-acetic acid.

The compounds shown in the above Examples are listed in the Table 2.

TABLE 2

| Example No. | R$^1$ | R$^2$ | R$^{3'}$ | R$^{4'}$ |
|---|---|---|---|---|
| 1 | 2-methylthiobenzyl | ethyl | methanesulfonamido | methoxymethoxy |
| 2 | 2-methylthiobenzyl | ethyl | benzenesulfonamido | methoxymethoxy |
| 3(1) | 2-methylthiobenzyl | ethyl | methanesulfonamido | methoxy |
| 3(2) | 2-chloro-6-fluorobenzyl | ethyl | methanesulfonamido | methoxy |
| 3(3) | 2-chloro-6-fluorobenzyl | ethyl | methanesulfonamido | isobutoxy |
| 3(4) | 2-methylthiobenzyl | ethyl | methanesulfonamido | propoxy |
| 3(5) | 2-methylthiobenzyl | ethyl | ethanesulfonamido | methoxymethoxy |
| 3(6) | 2-methylthiobenzyl | ethyl | propanesulfonamido | methoxymethoxy |
| 3(7) | 2-methylthiobenzyl | ethyl | isopropanesulfonamido | propoxy |
| 3(8) | 2-methylthiobenzyl | ethyl | trifluoromethanesulfonamido | methoxymethoxy |
| 3(9) | 2-methylthiobenzyl | ethyl | isopropanesulfonamido | methoxymethoxy |
| 3(10) | 2-methylthiobenzyl | ethyl | ethanesulfonamido | propoxy |
| 3(11) | 2-methylthiobenzyl | ethyl | methanesulfonamido | 2-methoxyethyl |
| 4 | 2-methylthiobenzyl | ethyl | ethoxycarbonyl | methoxy |
| 5 | 2-methylthiobenzyl | H | methanesulfonamido | methoxymethoxy |
| 6 | 2-methylthiobenzyl | ethyl | methanesulfonamido | isobutoxy |
| 7(1) | 2-methylthiobenzyl | ethyl | methanesulfonamido | carboxymethoxy |
| 7(2) | 2-methylthiobenzyl | ethyl | methanesulfonamido | allyloxy |
| 7(3) | 2-methylthiobenzyl | ethyl | methanesulfonamido | butoxy |
| 7(4) | 2-methylthiobenzyl | ethyl | methanesulfonamido | 2,2,2-trifluoroethoxy |
| 8 | 2-methylthiobenzyl | ethyl | methanesulfonamido | methylaminocarbonylmethoxy |
| 9(1) | 2-methylthiobenzyl | ethyl | methanesulfonamido | propylaminocarbonylmethoxy |
| 9(2) | 2-methylthiobenzyl | ethyl | methanesulfonamido | piperazinecarbonylmethoxy |
| 10(1) | 2-methylthiobenzyl | pivaloyloxymethyl | methanesulfonamido | methoxymethoxy |
| 10(2) | 2-methylthiobenzyl | 1-(cyclohexyloxycarbonyloxy)-ethyl | methanesulfonamido | methoxymethoxy |
| 11(1) | 2-methylthiobenzyl | H | benzensulfonamido | methoxymethoxy |
| 11(2) | 2-methylthiobenzyl | H | methanesulfonamido | methoxy |
| 11(3) | 2-methylthiobenzyl | ethyl | carboxy | methoxy |
| 11(4) | 2-chloro-6-fluorobenzyl | H | methanesulfonamido | methoxy |
| 11(5) | 2-chloro-6-fluorobenzyl | H | methanesulfonamido | isobutoxy |
| 11(6) | 2-methylthiobenzyl | H | methanesulfonamido | isobutoxy |
| 11(7) | 2-methylthiobenzyl | H | methanesulfonamido | propoxy |
| 11(8) | 2-methylthiobenzyl | H | methanesulfonamido | butoxy |
| 11(9) | 2-methylthiobenzyl | H | ethanesulfonamido | propoxy |
| 11(10) | 2-methylthiobenzyl | H | methanesulfonamido | 2-methoxyethyl |
| 11(11) | 2-methylthiobenzyl | H | isopropanesulfonamido | methoxymethoxy |
| 11(12) | 2-methylthiobenzyl | H | methanesulfonamido | methylaminocarbonylmethoxy |
| 11(13) | 2-methylthiobenzyl | H | methanesulfonamido | propylaminocarbonylmethoxy |
| 11(14) | 2-methylthiobenzyl | H | methanesulfonamido | piperazinecarbonylmethoxy |
| 11(15) | 2-methylthiobenzyl | H | isopropanesulfonamide | propoxy |
| 11(16) | 2-methylthiobenzyl | H | ethanesulfonamido | methoxymethoxy |
| 11(17) | 2-methylthiobenzyl | H | propanesulfonamido | methoxymethoxy |
| 11(18) | 2-methylthiobenzyl | H | trifluoromethanesulfonamido | methoxymethoxy |
| 11(19) | 2-methylthiobenzyl | H | methanesulfonamido | 2,2,2-trifluoroethoxy |

EXAMPLE 12

A tablet is prepared by a conventional method using 100 mg of the compound produced in Example 1, 165 mg of lactose, 25 mg corn starch, 4 mg of polyvinyl alcohol and 1 mg of magnesium stearate.

EXAMPLE 13

The compound (5 g) produced in Example 1 is dissolved in a distilled water for injection to make the total volume 100 ml. The solution is subjected to an aseptic filtration using a membrane filter of 0.22 micrometer (manufactured by Sumitomo Electric, Japan or by Saltorius, Germany). Each 2 ml of the filtrate is placed in a washed and sterilized vial and dried by freezing by a conventional method to prepare a freeze-dried injection of 100 mg/vial.

EXAMPLE 14

A tablet is prepared by a conventional method using 100 mg of the compound produced in Example 5, 165 mg of lactose, 25 mg of corn starch, 4 mg of polyvinyl alcohol and 1 mg of magnesium stearate.

EXAMPLE 15

The compound (5 g) produced in Example 5 is dissolved in a distilled water for injection. to make the total volume 100 ml. The solution is subjected to an aseptic filtration using a membrane filter of 0.22 micrometer (manufactured by Sumitomo Electric, Japan or by Saltorius, Germany). Each 2 ml of the filtrate is placed in a washed and sterilized vial and dried by freezing by a conventional method to prepare a freeze-dried injection of 100 mg/vial.

EXAMPLE 16

A tablet is prepared by a conventional method using 100 mg of the compound (5) produced in Example 3, 165 mg of lactose, 25 mg of corn starch, 4 mg of polyvinyl alcohol and 1 mg of magnesium stearate.

EXAMPLE 17

The compound (5) (5 g) produced in Example 3 was dissolved in a distilled water for injection to make the total volume 100 ml. The solution was subjected to an aseptic filtration using a membrane filter Of 0.22 micrometer (manufactured by Sumitomo Electric, Japan or by Saltorius, Germany). Each 2 ml of the viltrate was placed in a washed and sterilized vial and dried by freezing to prepare a freeze-dried injection of 100 mg/vial.

EXAMPLE 18

A tablet is prepared by a conventional method using 100 mg of the compound (16) produced in Example 11, 165 mg of lactose, 25 mg of corn starch, 4 mg of polyvinyl alcohol and 1 mg of magnesium stearate.

EXAMPLE 19

The compound (16) (5 g) produced in Example 11 is dissolved in a distilled water for injection to make the total volume 100 ml. The solution is subjected to an aseptic filtration using a membrane filter of 0.22 micrometer (manufactured by Sumitomo Electric, Japan or by Saltorius, Germany). Each 2 ml of the filtrate is placed in a washed and sterilized vial and dried by freezing by a conventional method to prepare a freeze-dried injection of 100 mg/vial.

Experimental Example 1

Binding Test to $ET_A$ receptor expressed in CHO cell:
Procedure
 cells: CHO cell expressing human $ET_A$ 24 endothelin receptor, i.e. $ET_A$ 24 cells
 medium: DMEM 10% FCS Gln, nonessential amino acids, penicillin, streptomycin Cells were seeded in 12 wells of 24 well plates at a density of $2 \times 10^5$ cells/well (1 ml medium/well). On the next day, [$^3$H]arachidonic acid was added to each well to be 250 nCi(nanocurie)/ml. On the next day, the medium was sucked from the wells by the use of an aspirator to remove free arachidonic acid and floating cells, and then 0.5 ml of medium was added. This procedure was repeated again. After allowing to stand for 30 minutes in a $CO_2$ incubator, the medium was exchanged rapidly.

The sample of compound obtained in Example 5 or compound 16 of Example 11 was stepwise diluted with a buffer solution for dilution, containing $3.15 \times 10^{-8}$M endothelin-1 (ET-1) {20 mM Tris, 5 mM Mg(AcO)$_2$, 2 mM EGTA, 0.03% NaN$_3$, 0.1% BSA, 0.05% CHAPS}. 10 µl of the solution was added to each well (final concentration of ET-1: $6.3 \times 10^{-10}$M). The maximum reaction value was estimated by adding 10 µl of $3.15 \times 10^{-8}$M ET-1. The radio activity under no stimulation was estimated by adding the buffer solution for dilution. After allowing to-stand for 30 minutes in the $CO_2$ incubator, the medium was completely collected and the radio activity of [$^3$H]arachidonic acid released in the medium was measured by a liquid scintillation counter. IC$_{50}$ values were calculated by hill plot from the concentration and relative reaction value of each sample.

Abbreviations:
DMEM: Dulbecco's medified Eagle Medium
FCS : fetal calf serum
AcO : acetyloxy
EGTA: ethyleneglycol bis(2-aminoethyl-ether)tetraacetic acid
BSA : bovine serum albumin
CHAPS: 3-[(3-chloroamidopropyl)dimethyl-ammonio]-1-propanesulfonate Results IC$_{50}$ values obtained are shown in Table 3:

TABLE 3

| Test compound | IC$_{50}$ value: µM |
|---|---|
| Compound obtained in Example 5 | 0.39 (n=2) |
| Compound 16 of Example 11 | 0.11 (n=2) |

Experimental Example 2

Binding Test to $ET_B$ receptor expressed in CHO cell:
Procedure
 cells: CHO cell expressing human $ET_B$ endothelin receptor, i.e. $ET_B$ 12 cells
 medium: DMEM 10% FCS Gln, nonessential amino acids, penicillin, streptomycin Cells were seeded in 12 wells of 24 well plates at a density of $2 \times 10^5$ cells/well (1 ml medium/well). On the next day, [$^3$H]arachidonic acid was added to each well to be 250 nCi(nanocurie)/ml. On the next day, the medium was sucked from the wells by the use of an aspirator to remove free arachidonic acid and floating cells, and then 0.5 ml of medium was added. This procedure was repeated again. After allowing to stand for 30 minutes in a $CO_2$ incubator, the medium was exchanged rapidly.

The sample of compound obtained in Example 5 or compound 16 of Example 11 was stepwise diluted with a buffer solution for dilution, containing $3.15 \times 10^{-8}$M endothelin-1 (ET-1) {20 mM Tris, 5 mM Mg(AcO)$_2$, 2 mM EGTA, 0.03% NaN$_3$, 0.1% BSA, 0.05% CHAPS}. 10 μl of the solution was added to each well (final concentration of ET-1: 6.3×10$^{-10}$M). The maximum reaction value was estimated by adding 10 μl of 3.15×10$^{-8}$M ET-1. The radio activity under no stimulation was estimated by adding the buffer solution for dilution. After allowing to-stand for 30 minutes in the CO$_2$ incubator, the medium was completely collected and the radio activity of [$^3$H]arachidonic acid released in the medium was measured by a liquid scintillation counter. IC$_{50}$ values were calculated by Hill Plot from the concentration and relative reaction value of each sample.

Results

IC$_{50}$ values obtained are shown in Table 4:

TABLE 4

| Test compound | IC$_{50}$ value: μM |
|---|---|
| Compound obtained in Example 5 | 0.49 (n=2) |
| Compound 16 of of Example 11 | 0.13 (n=2) |

Experimental Example 3

Inhibition Test on coronary artery where ET$_A$ is expressed:

Procedure 3-mm ring samples for vehicle group and drug-treating group were prepared by removing fat and connective tissue from coronary artery enucleated from porcine heart and obtained from the adjacent portions thereof. The samples, hanging in Magnus tube filled with Krebs solution, were stabilized for 90 minutes under 2 g of static tension. After subjecting the samples to constriction for 10 minutes by potassium chloride (KCl) (60 mM) to obtain the maximum reaction, the samples were then washed and stabilized for 60 minutes. After pre-treating compound obtained in Example 5 or Compound 16 of Example 11 or vehicle (H$_2$O) for 30 minutes, ET-1 (2 mM) was added to observe the maximum constriction.

The constriction efficiency (% KCl) of ET-1 was calculated as a relative value to KCl constriction of each sample which was regarded as 100%. Further, the inhibiting efficiency was calculated from the constriction efficiency of the drug-treating group calculated as a relative value to the constriction of the vehicle group which was regarded as 100%.

Results

The results are shown in Table 5.

TABLE 5

| Compound | % inhibition (MEAN ± S.E.M.) (n=) artery (ET-1 3nM) | | Binding IC$_{50}$ (μM) |
|---|---|---|---|
| | 0.1 μM | 1 μM | ET$_A$ |
| Compound in Example 5 | 7.6 ± 37.3 (3) | 78.1 ± 11.9 (4) | 0.0076 |
| Compound 16 of Example 11 | — | 33.1 ± 8.6 (4) | 0.0061 |

It is apparent from the results of Table 5 that in the ring samples of porcine coronary artery in which ET$_A$ is expressed, the compounds of present invention suppress vascular (smooth muscle) constriction through the agonist of ET$_A$, i.e. ET-1 (3 nM).

Thus, it was confirmed that the compounds of present invention are antagonists for ET$_A$ receptor.

Experimental Example 4

Inhibition Test on coronary vein where ET$_B$ is expressed:

Procedure 1

3-mm ring samples for vehicle group and drug-treating group were prepared by removing fat and connective tissue from coronary vein enucleated from porcine heart and obtained from the adjacent portions thereof. The samples, hanging in Magnus tube filled with Krebs solution, were stabilized for 90 minutes under 0.5 g static tension. After subjecting the samples to constriction for 10 minutes by potassium chloride (KCl) (60 mM) to obtain the maximum reaction, the samples were washed and stabilized for 60 minutes. After pre-treating compound obtained in Example 5 or Compound 16 of Example 11 or vehicle (H$_2$O) for 30 minutes, S6c (1 nM) (S6c: sarafotoxin S6c, peptide type snake toxin consisting of 21 amino acids, it is useful for the selective agonist to ET$_B$ receptor owing to the similarity of its structure to endothelin) was added to observe the maximum constriction.

The constriction efficiency (% KCl) of S6c was calculated as a relative value to KCl constriction of each sample which was regarded as 100%. Further, the inhibiting efficiency was calculated from the constriction efficiency of the drug-treating group calculated as a relative value to the constriction of the vehicle group which was regarded as 100%.

Results

The results are shown in Table 6.

TABLE 6

| Compound | % inhibition (MEAN ± S.E.M.) (n=) vein (S6c 1 nM) | | Binding IC$_{50}$ (μM) |
|---|---|---|---|
| | 0.1 μM | 10 μM | ET$_B$ |
| Compound in Example 5 | 73.4 ± 3.1 (3) | 100 ± 0 (4) | 0.100 |
| Compound 16 of Example 11 | 53.3 ± 4.4 (4) | 98.0 ± 1.1 (4) | 0.054 |

It is apparent from the results of Table 6 that in the ring samples of porcine coronary vein in which ET$_B$ is expressed, the compounds of present invention suppress vascular (smooth muscle) constriction through the agonist of ET$_B$, i.e. S6c (1 nM).

Thus, it was confirmed that the compounds of present invention are antagonists for ET$_B$ receptor.

Experimental Example 5

Binding Test to ETA receptor expressed in an insect cell Sf9:

Procedure

Endothelin (ET) receptors were prepared by diluting fractions of insect cell (Sf9) membrane having human endothelin-A (ETA) receptors expressed, with an assay buffer {20 mM Tris-HCl, 2 mM EGTA (ethyleneglycol bls(2-aminoethylether) tetra acetic acid), 5 mM magnesium acetate, 0.1% BSA (bovine serum albumin), 0.03% NaN$_3$, 0.5 mM PMSF (phenyl methyl sulfonyl fluoride), 20 μg/ml leupeptin, 4 μg/ml E-64 (products of the Peptide Institute, Japan), 1 μg/ml pepstatin, (pH 7.2)} respectively in a concentration of 1.4 μg/ml in the former case and 0.7 μg/ml in the latte case.

To 100 μl of each portion was added 5 nM[$^{125}$I] endothelin-1 (2 μl). A dimethylsulfoxide solution (3 μl) of the test compound was added thereto and incubated at 25° C. for 60 minutes.

And, to determine the maximum binding amount (B$_0$) and non-specific binding amount (NSB), lots to which a dimethyl sulfoxide solution (3 μl) or a dimethyl sulfoxide solution (3 μl) containing endothelin-1 (10$^{-3}$M) had been added, were also incubated.

These lots were supplemented with 0.05% CHAPS(3-[(3-chloroamidopropyl)dimethylammonio]-1-propanesulfonate)-assay buffer (1.5 ml), subjected to filtration through a glass fiber filter GF/F (trade name; product of Whatman Ltd. (England)), and then washed with the same buffer (1.5 ml)).

Radioactivity on the filter was counted in a gamma-counter to determine the Percent Maximum Binding (PMB) in accordance with the aforesaid calculation formula. The concentration causing PMB=50% was determined as $IC_{50}$ value. $IC_{50}$ values of some of the compounds of this invention, synthesized in the above-mentioned examples, are shown in Table 7.

TABLE 7

| Test compound (Compounds are shown by the Example No.) | $IC_{50}$ value: $\mu M$ Human endotherin-A receptor |
| --- | --- |
| 5 | 0.011 |
| potassium salt of 5 | 0.0076 |
| 11(7) | 0.018 |
| 11(9) | 0.015 |
| 11(11) | 0.0066 |
| 11(15) | 0.011 |
| 11(16) | 0.0061 |
| 11(17) | 0.022 |

According to the result shown in the Table 5, it has been proved that the compound or its salt of the present invention have excellent endothelin receptor antagonistic action to endothelin-B receptor.

Experimental Example 6
Binding Test to $ET_B$ receptor expressed in an insect cell Sf9:
Procedure Endothelin (ET) receptors were prepared by diluting fractions of insect cell (Sf9) membrane having human endothelin-B (ETB) receptors expressed, with an assay buffer {200 mM Tris-HCl, 2 mM EGTA (ethylenegiycol bis(2-aminoethylether) tetra acetic acid), 5 mM magnesium acetate, 0.1% BSA (bovine serum albumin), 0.03% $NaN_3$, 0.5 mM PMSF(phenyl methyl sulfonyl fluoride), 20 $\mu g/ml$ leupeptin, 4 $\mu g/ml$ E-64 (products of the Peptide Institute), 1 $\mu g/ml$ pepstatin, (pH 7.2)} respectively in a concentration of 1.4 $\mu g/ml$ in the former case and 0.7 $\mu g/ml$ in the latter case.

To 100 gl of each portion was added 5 $nM[^{125}I]$ endothelin-1 (2 $\mu l$). A dimethylsulfoxide solution (3 $\mu l$) of the sample was added thereto and incubated at 25° C. for 60 minutes.

And, to determine the maximum binding amount ($B_0$) and non-specific binding amount (NSB), lots to which a dimethyl sulfoxide solution (3 $\mu l$) or a dimethyl sulfoxide solution (3 $\mu l$) containing endothelin-1 ($10^{-5}M$) had been added, were also incubated.

These lots were supplemented with 0.05% CHAPS(3-[(3-chloroamidopropyl)dimethylammonio]-1-propanesulfonate)-assay buffer (1.5 ml), subjected to filtration through a glass fiber filter GF/F (trade name; product of Whatman Ltd. (England)), and then washed with the same buffer (1.5 ml)).

Radioactivity on the filter was counted in a gamma-counter to determine the Percent Maximum Binding (PMB) in accordance with the aforesaid calculation formula. The concentration causing PMB=50% was determined as $IC_{50}$ value. $IC_{50}$ values of some of the compounds of this invention, synthesized in the above-mentioned examples, are shown in Table 8.

TABLE 8

| Test compound (Compounds are shown by the Example No.) | $IC_{50}$ value: $\mu M$ Human endotherin-B receptor |
| --- | --- |
| 5 | 0.20 |
| potassium salt of 5 | 0.10 |
| 11(7) | 0.22 |
| 11(9) | 0.11 |
| 11(11) | 0.090 |
| 11(15) | 0.094 |
| 11(16) | 0.054 |
| 11(17) | 0.047 |

According to the result shown in the Table 6, it has been proved that the compound or its salt of the present invention have excellent endothelin receptor antagonistic action to endothelin-A receptor.

The potassium salt of the compound of the Working Example 5 was produced by employing the compound of the Working Example 5, potassium carbonate and water-ethanol in a conventional manner.

Industrial applicability

The thienopyrimidine derivative of the present invention possesses outstanding endothelin receptor antagonist activity and, therefore, the endothelin antagonist composition containing this thienopyrimidine derivative in accordance with the invention can be used with advantage as a prophylactic or therapeutic drug for acute renal failure, myocardial infarction, liver disorder, angina pectoris, cerebral infarction, cerebrovasospasm, hypertension, kidney disease, asthma, ectopic angina, rayneau syndrome, pulmonary hypertension, surgical shock, chronic heart failure, atherosclerosis, cardiac hypertrophy, migrane, etc., as a prophylactic or therapeutic drug for organ surgery- or graftassociated hypofunction of organs, or as a prophylactic drug for vascular restenosis following percutaneous transluminal coronary engioplasty (PTCA), or as in inhibitor for vasoconstriction of coronary artery, coronary vein, cerebrovascular system or pulmonary vascular system.

What is claimed is:
1. A compound of the formula:

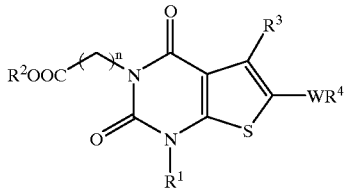

wherein $R^1$ is hydrogen, $C_{1-6}$ alkyl or a group of the formula: —$(CH_2)mQ'$ in which m is an integer of 0–3, Q' is $C_{6-14}$ aryl which may be substituted by (i) halogen, (ii) nitro, (iii) cyano, (iv) amino, (v) carboxyl which may be substituted with $C_{1-3}$ alkyl, $C_{3-7}$ cycloalkyl, phenyl, naphthyl, $C_{7-10}$ aralkyl, or heterocyclic group which is 5- to 13-membered aromatic heterocyclic group having 1–4 heteroatoms selected from oxygen, sulfur and nitrogen as the atom for constituting the ring or a saturated or unsaturated non-aromatic heterocyclic group selected from the group consisting of oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl each of which may have one to three substituents selected from the group consisting of $C_{1-3}$ alkyl, $C_{2-4}$ alkenyl, $C_{3-4}$ alkynyl, $C_{3-7}$ cycloalkyl, phenyl, naphthyl, a 5- to 9-membered aromatic heterocyclic group having 1–4 heteroatoms selected from nitrogen, oxygen and sulfur, a 5- to 9-membered non-aromatic heterocyclic group having 1–4 heteroatoms selected from nitrogen, oxygen and sulfur, $C_{7-10}$ aralkyl, amino, monoalkylamino having 1–6 carbons, N,N-disubstituted amino wherein the substituents are alkyl having 2–6 carbons, amidino, $C_{1-8}$ alkyl-carbonyl, $C_{6-14}$ aryl-carbonyl, carbamoyl, $C_{1-6}$ alkyl-carbamoyl, N,N-disubstituted carbamoyl substituted with $C_{1-6}$ alkyl, sulfamoyl, N-alkylsulfamoyl substituted with $C_{1-6}$ alkyl, N,N-disubstituted sulfamoyl substituted with $C_{1-6}$ alkyl, carboxyl, $C_{1-3}$ alkoxy-carbonyl, hydroxyl, optionally-substituted $C_{1-3}$ alkoxy which may be substituted with $C_{1-3}$ lower alkyl, halogen, $C_{1-3}$ alkylthio or hydroxyl, $C_{2-4}$ alkenyloxy, $C_{3-7}$ cycloalkyloxy, $C_{7-10}$ aralkyloxy, phenyloxy, naphthyloxy, mercapto, $C_{1-3}$ alkyl, alkylthio, $C_{7-10}$ aralkylthio, phenylthio, naphthylthio, alkylenedioxy having 1–3 carbons, sulfo, cyano, azido, nitro, nitroso and a halogen atom, (vi) $C_{1-6}$ alkylenedioxy or (vii) a group of the formula: —A—$R^6$ which A is a chemical bond or a connecting group selected from the group consisting of (1) $C_{1-4}$ alkylene, (2) $C_{2-6}$ alkenylene, (3) —$(CH_2)_c NR^{10}$— in which c is an integer of 0–3 and $R^{10}$ is hydrogen or $C_{1-6}$ alkyl, (4) —CO—, (5) a group of the formula: —$CONR^{10}$— in which $R^{10}$ has the same meaning as defined above, (6) —O—, (7) —S—, and (8) a group of the formula: —$NR^{10}SO_e$— in which e is an integer of 0–2 and $R^{10}$ has the same meaning as defined above, $R^6$ is (i) $C_{1-6}$ alkyl, (ii) $C_{3-10}$ cycloalkyl which may have one to three substituents selected from the group consisting of $C_{1-3}$ alkyl, $C_{2-4}$ alkenyl, $C_{3-4}$ alkynyl, $C_{3-7}$ cycloalkyl, phenyl, naphthyl, a 5- to 9-membered aromatic heterocyclic group having 1–4 heteroatoms selected from nitrogen, oxygen and sulfur, a 5- to 9-membered non-aromatic heterocyclic group having 1–4 heteroatoms selected from nitrogen, oxygen and sulfur, aralkyl having 7–10 carbons, amino, monoalkylamino having 1–6 carbons, N,N-disubstituted amino wherein the substituents are alkyl having 2–6 carbons, amidino, $C_{1-8}$ alkyl-carbonyl, arylcarbonyl having 6–14 carbons, carbamoyl, $C_{1-6}$ alkyl-carbamoyl, N,N-disubstituted carbamoyl substituted with alkyl having 1–6 carbons, sulfamoyl, N-alkyl-sulfamoyl substituted with alkyl having 1–6 carbons, N,N-disubstituted sulfamoyl substituted with alkyl having 1–6 carbons, carboxyl, $C_{1-3}$ alkoxy-carbonyl, hydroxyl, optionally-substituted $C_{1-3}$ alkoxy which may be substituted with $C_{1-3}$ lower alkyl, halogen, $C_{1-3}$ alkylthio or hydroxyl, $C_{2-4}$ alkenyloxy, $C_{3-7}$ cycloalkyloxy, $C_{7-10}$ aralkyloxy, phenyloxy, naphthyloxy, mercapto, $C_{1-3}$ alkylthio, $C_{7-10}$ aralkylthio, phenylthio, naphthylthio, alkylenedioxy having 1–3 carbons, sulfo, cyano, azido, nitro, nitroso and a halogen atom, or (iii) a 5-to 13-membered aromatic heterocyclic group having 1–4 heteroatoms selected from oxygen, sulfur and nitrogen as the atom for constituting the ring or a saturated or unsaturated non-aromatic heterocyclic group selected from the group consisting of oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl each of which may have one to three substituents selected from the group consisting of $C_{1-3}$ alkyl, $C_{2-4}$ alkenyl, $C_{3-4}$ alkynyl, $C_{3-7}$ cycloalkyl, phenyl, naphthyl, a 5- to 9-membered aromatic heterocyclic group having 1–4 heteroatoms selected from nitrogen, oxygen and sulfur, a 5- to 9-membered non-aromatic heterocyclic group having 1–4 heteroatoms selected from nitrogen, oxygen and sulfur, aralkyl having 7–10 carbons, amino, monoalkylamino having 1–6 carbons, N,N-disubstituted amino wherein the substituents are alkyl having 2–6 carbons, amidino, $C_{1-8}$ alkyl-carbonyl, $C_{6-14}$ aryl-carbonyl, carbamoyl, $C_{1-6}$ alkyl-carbamoyl, N,N-disubstituted carbamoyl substituted with alkyl having 1–6 carbons, sulfamoyl, N-alkyl-sulfamoyl substituted with alkyl having 1–6 carbons, N,N-disubstituted sulfamoyl substituted with alkyl having 1–6 carbons, carboxyl, $C_{1-3}$ alkoxy-carbonyl, hydroxyl, optionally-substituted alkoxy having 1–3 carbons which may be substituted with $C_{1-3}$ alkyl, halogen, $C_{1-3}$ alkylthio or hydroxyl, alkenyloxy having 2-4 carbons, cycloalkyloxy having 3–7 carbons, aralkyloxy having 7–10 carbons, phenyloxy, naphthyloxy, mercapto, alkylthio having 1–3 carbons, aralkylthio having 7–10 carbons, phenylthio, naphthylthio, alkylenedioxy having 1–3 carbons, sulfo, cyano, azido, nitro, nitroso and a halogen atom;

$R^2$ is (i) hydrogen, (ii) a $C_{1-6}$ alkyl, (iii) $C_{3-6}$ cycloalkyl, (iv) $C_{2-6}$ alkenyl, (v) $C_{6-14}$ aryl or (vi) $C_{7-20}$ aralkyl each of which (ii) to (vi) may have substituents of (1) nitro, (2) hydroxyl, (3) oxo, (4) thioxo, (5) cyano, (6) carbamoyl, (7) carboxyl, (8) $C_{1-4}$ alkoxy-carbonyl, (9) sulfo, (10) halogen, (11) $C_{1-8}$ alkoxy, (12) $C_{6-12}$ aryloxy, (13) halogeno $C_{6-16}$ aryl, (14) $C_{1-6}$ alkylthio, (15) $C_{6-12}$ arylthio, (16) $C_{1-6}$ alkylsulfinyl, (17) $C_{1-6}$ alkylsulfonyl, (18) amino, (19) $C_{1-4}$ acylamino selected from the group consisting of formylamino, acetylamino and propionylamino, (20) mono- or di-$C_{1-4}$ alkylamino, (21) acyl selected from the group consisting of formyl, acetyl and hexanoyl, (22) $C_{6-12}$ aryl-carbonyl, (23) a 5- or 6-membered heterocyclic group having 1–4 heteroatoms selected from oxygen, sulfur and nitrogen, which may be substituted with one to four substituent(s) selected from (a) halogen, (b) $C_{1-4}$ alkyl and (c) halogenophenoxy, or (24) $C_{1-10}$ haloalkyl;

$R^3$ is hydrogen, or a group bonded through a carbon atom selected from the group consisting of $C_{1-6}$ alkyl, $C_{3-6}$ cycloalkyl, $C_{1-3}$ alkoxy $C_{1-6}$ alkyl, hydroxy $C_{1-6}$ alkyl, $C_{2-6}$ alkenyl, formyl, carboxyl, $C_{1-6}$ alkoxycarbonyl, cyano, mono- or di-$C_{1-6}$ alkylcarbamoyl, amidino, $C_{6-14}$ aryl, $C_{7-20}$ aralkyl, a five-membered group having one to four hetero atoms selected from the group consisting of 2- or 3-thienyl, 2- or 3-furyl, 2- or 3-pyrrolyl, 2-, 4- or 5-oxazolyl, 2-, 4- or 5-thiazolyl, 3-, 4- or 5-pyrazolyl pyrrolidinyl, 2-, 4- or 5-imidazolyl, 3- 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, and 1H- or 2H-tetrazolyl, a six-membered group having one to four hetero atoms selected from the group consisting of 2-, 3- or 4-pyridyl, N-oxido-2-, 3- or 4-pyridyl, 2-, 4- or 5-pyrimidinyl, N-oxido-2-, 4- or 5-pyrimidinyl, 2- or 3-thiomorpholinyl, 2- or 3-morpholinyl, piperidyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, pyrazinyl, N-oxido-3- and 4-pyridazinyl, and a bicyclic or tricyclic condensed group having one to four hetero atoms selected from the group consisting of benzofuryl, benzothiazolyl, benzoxazolyl, pyrrolo(1,2-b)pyridazinyl, pyrazolo(1,5-b)pyridyl, imidazo(1,2-a)pyridyl, triazolo(4,5-b)pyridazinyl, imidazo(1,2-b)pyridazinyl, 1,2,4-triazolo(4,3-a)pyridyl, benzimidazolyl, quinolyl, isoquinolyl, cinnolinyl, phthalazinyl, quinazolinyl, quinoxalinyl, indolidinyl, quinolidinyl, 1,8-naphthylidinyl, purinyl, pteridinyl, dibenzofuranyl, carbazolyl, acridinyl, phenanthridinyl, chromanyl, benzoxazinyl, phenazinyl, phenothiazinyl, phenoxazinyl, phthalazinyl, naphthyridiryl, phenoxathiinyl, phenanthrolinyl and thianthrenyl, or a group bonded through a nitrogen atom selected from the group consisting of (a) amino, (b) -NR$^8$R$^9$, in which R$^8$ is hydrogen, C$_{1-6}$ alkyl, C$_{3-6}$ cycloalkyl, C$_{6-14}$ aryl or a heterocyclic group which is 5-to 13-membered aromatic heterocyclic group selected from the group consisting of furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3 thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, and triazinyl, and aromatic fused heterocyclic group selected from the group consisting of benzofuranyl, isobenzofuranyl, benzo(b)thienyl, indolyl, isoindolyl, 1H-indazolyl, benzoimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, alpha-carbolinyl, beta-carbolinyl, gamma-carbolinyl, acridinyl, phenoxazinyl, phenothiazinyl, phenazinyl, phenoxathinyl, thianthrenyl, phenathridinyl, phenathrolinyl, pyrrolo( 1,2-b)pyridazinyl, pyrazolo( 1,5-a)pyridyl, imidazo(1 ,2-a)pyridyl, imidazo(1,5-a)pyridyl, imidazo(1,2-b)pyridazinyl, 1,2,4-triazolo(4,3-a)pyridyl and 1,2,4-triazolo(4,3-b)pyridazinyl or a saturated or unsaturated non-aromatic heterocyclic group selected from the group consisting of oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl each of which may have one to three is selected from the group consisting of C$_{1-3}$ alkyl, C$_{2-4}$ alkenyl, C$_{3-4}$ alkynyl, C$_{3-7}$ cycloalkyl, phenyl, naphthyl, a 5- to 9-membered aromatic heterocyclic group having 1–4 heteroatoms selected from nitrogen, oxygen and sulfur, a 5- to 9-membered non-aromatic heterocyclic group having 1–4 heteroatoms selected from nitrogen, oxygen and sulfur, aralkyl having 7–10 carbons, amino, monoalkylamino having 1–6 carbons, N,N-disubstituted amino wherein the substituents are alkyl having 2 to 6 carbon aminos, C$_{1-8}$ alkyl-carbanoyl, C$_{6-14}$ aryl-carbonyl, carbamoyl, C$_{1-6}$ alkyl-carbamoyl, N,N-disubstituted carbamoyl substituted with alkyl having 1–6 carbons, sulfamoyl, N-alkylsulfamoyl substituted with alkyl having 1–6 carbons, N,N-disubstituted sulfamoyl substituted with alkyl having 1–6 carbons, carboxyl, C$_{1-3}$ alkoxy-carbonyl, hydroxyl, optionally-substituted alkoxy having 1–3 carbons which may be substituted with C$_{1-3}$ alkyl, halogen, C$_{1-3}$ alkylthio or hydroxyl, alkenyloxy having 2–4 carbons, cycloalkyloxy having 3–7 carbons, aralkyloxy having 7–10 carbons, phenyloxy, naphthyloxy, mercapto, alkylthio having 1–3 carbons, aralkylthio having 7–10 carbons, phenylthio, naphthylthio, alkylenedioxy having 1–3 carbons, sulfo, cyano, azido, nitro, nitroso and a halogen atom, and R$^9$ is hydrogen or C$_{1-6}$ alkyl, and (c) a heterocyclic group selected from the group consisting of 1H-1-pyrrolyl, 1-imidazolinyl, 1-pyrazolyl, 1-indolyl, 1H-1-indazolyl, 7-purinyl, 1-pyrrolidinyl, 1-pyrrolinyl, 1-imidazolinyl, 1-pyrazolidinyl, 1-piperazinyl, 1-pyrazolinyl, 1-piperidinyl, 4-morpholinyl and 4-thiomorpholinyl;

R$^4$ is (A) C$_{6-14}$ aryl which may have one to three substituents selected from the group consisting of (1) C$_{1-3}$ alkyl, (2) C$_{2-4}$ alkenyl, (3) C$_{3-4}$ alkynyl, (4) C$_{3-7}$ cycloalkyl, (5) phenyl, (6) naphthyl, (7) a 5- to 9-membered aromatic heterocyclic group having 1–4 heteroatoms selected from nitrogen, oxygen and sulfur, (8) a 5- to 9-membered non-aromatic heterocyclic group having 1–4 heteroatoms selected from nitrogen, oxygen and sulfur, (9) C$_{7-10}$ aralkyl, (10) amino, (11) monoalkylamino having 1–6 carbons, (12) N,N-disubstituted amino wherein the substituents are C$_{2-6}$ alkyl, (13) amidino, (14) C$_{1-8}$ alkyl-carbonyl, (15) C$_{6-14}$ aryl-carbonyl, (16) carbamoyl, (17) C$_{1-6}$ alkyl-carbamoyl, (18) N,N-disubstituted carbamoyl substituted with C$_{1-6}$ alkyl, (19) sulfamoyl, (20) N-alkylsulfamoyl substituted with alkyl having 1–6 carbons, (21) N,N-disubstituted sulfamoyl substituted with alkyl having 1–6 carbons, (22) carboxyl, (23) C$_{1-3}$ alkoxy-carbonyl, (24) hydroxyl, (25) optionally-substituted C$_{1-3}$ alkoxy which may be substituted with C$_{1-3}$ alkyl, halogen, C$_{1-3}$ alkylthio or hydroxyl, (26) alkenyloxy having 2–4 carbons, (27) cycloalkyloxy having 3–7 carbons, (28) aralkyloxy having 7–10 carbons, (29) phenyloxy, (30) naphthyloxy, (31) mercapto, (32) alkylthio having 1–3 carbons, (33) aralkylthio having 7–10 carbons, (34) phenylthio, (35) naphthylthio, (36) alkylenedioxy having 1–3 carbons, (37) sulfo, (38) cyano, (39) azido, (40) nitro, (41) nitroso and (42) a halogen atom, (B) C$_{3-10}$ cycloalkyl which may have one to three substituents selected from the group consisting of (1) C$_{1-3}$ alkyl, (2) C$_{2-4}$ alkenyl, (3) C$_{3-4}$ alkynyl, (4) C$_{3-7}$ cycloalkyl, (5) phenyl, (6) naphthyl, (7) a 5- to 9-membered aromatic heterocyclic group having 1–4 heteroatoms selected from nitrogen, oxygen and sulfur, (8) a 5- to 9-membered non-aromatic heterocyclic group having 1–4 heteroatoms selected from nitrogen, oxygen and sulfur, (9) C$_{7-10}$ aralkyl, (10) amino, (11) monoalkylamino having 1–6 carbons, (12) N,N-disubstituted amino wherein the substituents are alkyl having 2–6 carbons, (13) amidino, (14) C$_{1-8}$ alkyl-carbonyl, (15) C$_{6-14}$ aryl-carbonyl, (16) carbamoyl, (17) C$_{1-6}$ alkyl-carbamoyl, (18) N,N-disubstituted carbamoyl substituted with alkyl having 1–6 carbons, (19) sulfamoyl, (20) N-aikylsulfamoyl substituted with alkyl having 1–6 carbons, (21) N,N-disubstituted sulfamoyl substituted with alkyl having 1–6 carbons, (22) carboxyl, (23) alkoxycarbonyl having 1–3 carbons, (24) hydroxyl, (25) optionally-substituted alkoxy having 1–3 carbons which may be substituted with C$_{1-3}$ alkyl, halogen, C$_{1-3}$ alkylthio or hydroxyl, (26) alkenyloxy having 2–4 carbons, (27) cycloalkyloxy having 3–7 carbons, (28) aralkyloxy having 7–10 carbons, (29) phenyloxy, (30) naphthyloxy, (31) mercapto, (32) alkylthio having 1–3 carbons, (33) aralkylthio having 7–10 carbons, (34) phenylthio, (35) naphthylthio, (36) alkylenedioxy having 1–3 carbons, (37) sulfo, (38) cyano, (39) azido, (40) nitro, (41) nitroso and (42) a halogen atom, (C) a 5-to 13-membered aromatic heterocyclic group having 1–4 heteroatoms selected from oxygen, sulfur and nitrogen as the atom for constituting the ring, (D) a saturated or unsaturated non-aromatic heterocyclic group selected from the group consisting of oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl each of which may have one to three substituents selected from the group consisting of (1) C$_{1-3}$ alkyl, (2) C$_{2-4}$ alkenyl, (3) C$_{3-4}$ alkynyl, (4) C$_{3-7}$ cycloalkyl, (5) phenyl, (6) naphthyl, (7) a 5- to 9-membered aromatic heterocyclic group having 1–4 heteroatoms selected from nitrogen, oxygen and sulfur, (8) a 5- to 9-membered non-aromatic heterocyclic group having 1–4 heteroatoms selected from nitrogen, oxygen and sulfur, (9) aralkyl having 7–10 carbons, (10) amino, (11) monoalkylamino having 1–6 carbons, (12) N,N-disubstituted amino wherein the substituents are alkyl having 2–6 carbons (13), amidino, (14) C$_{1-8}$ alkyl-carbonyl, (15) C$_{6-14}$ aryl-carbonyl, (16) carbamoyl, (17) C$_{1-6}$ alkyl-carbamoyl, (18) N,N-disubstituted carbamoyl substituted with alkyl having 1–6 carbons, (19) sulfamoyl, (20) N-alkylsulfamoyl substituted with alkyl having 1–6 carbons, (21) N,N-disubstituted sulfamoyl substituted with alkyl having 1–6 carbons, (22) carboxyl, (23) C$_{1-3}$ alkoxy-carbonyl, (24) hydroxyl, (25) optionally-substituted alkoxy having 1–3 carbons which may be substituted with C$_{1-3}$ lower alkyl, halogen, C$_{1-3}$ alkylthio or hydroxyl, (26) alkenyloxy having 2–4 carbons, (27) cycloalkyloxy having 3–7 carbons, (28) aralkyloxy having 7–10 carbons, (29) phenyloxy, (30) naphthyloxy, (31) mercapto, (32) alkylthio having 1–3 carbons, (33) aralkylthio having 7–10 carbons, (34) phenylthio, (35) naphthylthio, (36) alkylenedioxy having 1–3 carbons, (37) sulfo, (38) cyano, (39) azido, (40) nitro, (41) nitroso and a (42) halogen atom, or (E) a group of the formula: —COOR$^{5'}$ (in which R$^{5'}$ is hydrogen or C$_{1-6}$ alkyl);

W is a chemical bond or a connecting group selected from the group consisting of (1) C$_{1-4}$ alkylene, (2) C$_{2-6}$ alkenylene, (3) —(CH$_2$)$_c$NR$^{10}$— (in which c is an integer of 0–3 and R$^{10}$ is hydrogen or C$_{1-6}$ alkyl), (4) —CO—, (5) a group of the formula: —CONR$^{10}$— (in which R$^{10}$ has the same meaning as defined above), (6) —O—, (7) —S—, and (8) a group of the formula: —NR$^{10}$SO$_e$— in which e is an integer of 0–2 and R$^{10}$ has the same meaning as defined above and n is an integer of 1–3, or a salt thereof.

2. A compound of the formula:

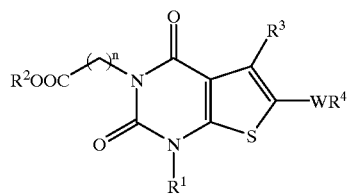

wherein each of R$^1$ and R$^2$ are hydrogen or a C$_{1-20}$ hydrocarbon residue selected from the group consisting of C$_{1-10}$ alkyl, C$_{3-10}$ cycloalkyl, C$_{7-10}$ bicycloalkyl, C$_{2-10}$ alkenyl, C$_{6-14}$ aryl and C$_{7-20}$ aralkyl each of which may optionally have (1) halogen, (2) nitro, (3) nitroso, (4) cyano, (5) hydroxyl group which may optionally be substituted by (i) C$_{1-6}$ alkyl which may optionally be substituted by hydroxyl, C$_{1-6}$ alkoxy, C$_{1-3}$ alkoxy-C$_{1-3}$ alkoxy, C$_{1-3}$ alkylthio, carboxyl, carbamoyl, C$_{1-6}$ alkyl-carbamoyl, 5- to 7-membered nitrogen containing heterocyclic group-carbonyl or halogen, (ii) formyl, (iii) C$_{7-20}$ aralkyl which may optionally be substituted by halogen, C$_{1-3}$ alkoxy or C$_{1-4}$ alkyl (iv) C$_{6-14}$ aryl which may optionally be substituted by halogen, (v) C$_{2-6}$ alkenyl, (vi) C$_{3-7}$ cycloalkyl, (vii) C$_{1-3}$ alkoxy-carbonyl, (viii) mono- or di-C$_{1-6}$ alkyl-amino, (ix) C$_{1-3}$ alkoxy-carbonyl, (x) C$_{1-6}$ alkyl-carbonyl, or (xi) C$_{3-6}$ cycloalkyloxy-carbonyl, (6) a group of the formula: —S(O)f—R$^6$, wherein f is an integer of 0 to 2, R$^6$ represents a hydrogen atom or a hydrocarbon residue which has the same meaning as defined above, and may be substituted with halogen, nitro, cyano, hydroxy, oxo, thioxo, carboxyl, cyano-C$_{6-14}$ aryl, or halogeno-C$_{6-14}$ aryl, (7) a group of the formula: —NR$^9$R$^{10}$, wherein R$^9$ and R$^{10}$ each is (i) hydrogen, (ii) hydrocarbon residue, which has the same meaning as defined above, (iii) formyl, (iv) C$_{1-6}$ alkanoyl, or (v) a 5- to 13-membered heterocyclic group which is mentioned below, (8) a 5- to 13-membered heterocyclic group containing 1–4 heteroatoms selected from oxygen, sulfur and nitrogen as ring members, the heterocyclic group being optionally substituted by (i) halogen, (ii) C$_{1-4}$ alkyl, (iii) C$_{1-3}$ alkoxy, (iv) C$_{1-4}$ alkylthio, or (v) phenoxy which may optionally be substituted by a halogen, (9) sulfo, (10) C$_{6-14}$ aryl, (11) C$_{3-7}$ cycloalkyl, (12) C$_{1-6}$ alkylenedioxy, (13) oxo, (14) thioxo, (15) C$_{3-4}$ alkynyl, (16) C$_{3-10}$ cycloalkyl, (17) C$_{2-10}$ alkenyl, (18) C$_{7-20}$ aralkyl, (19) amidino, or (20) azido, R$^3$ is a C$_{1-6}$ alkyl group which is substituted by (i) a C$_{1-6}$ alkoxy-carbonyl group or (ii) a group of the formula: —NH—SO$_2$—R$^5$, wherein R$^5$ is (1) a C$_{1-6}$ alkyl group which may optionally be substituted by halogen or (2) a C$_{6-14}$ aryl group, R$^4$ is (A) C$_{1-20}$ hydrocarbon residue selected from the group consisting of C$_{1-10}$ alkyl, C$_{3-10}$ cycloalkyl, C$_{7-10}$ bicycloalkyl, C$_{2-10}$ alkenyl, C$_{6-14}$ aryl, and C$_{7-20}$ aralkyl each of which may optionally have the following substituents: (1) halogen, (2) nitro, (3) nitroso, (4) cyano, (5) hydroxyl group which may optionally be substituted by (i) C$_{1-6}$ alkyl which may optionally be substituted by hydroxyl, C$_{1-6}$ alkoxy, C$_{1-3}$ alkoxy-C$_{1-3}$ alkoxy, C$_{1-3}$ alkylthio, carboxyl, carbamoyl, C$_{1-6}$ alkyl-carbamoyl, 5- to 7-membered nitrogen containing heterocyclic group-carbonyl or halogen, (ii) formyl, (iii) C$_{7-20}$ aralkyl which may optionally be substituted by halogen, $C_{1-3}$ alkoxy or $C_{1-4}$ alkyl, (iv) $C_{6-14}$ aryl which may optionally be substituted by halogen, (v) $C_{2-6}$ alkenyl, (vi) $C_{3-7}$ cycloalkyl, (vii) $C_{1-3}$ alkoxycarbonyl, (viii) mono- or di-$C_{1-6}$ alkylamino, (ix) $C_{1-3}$ alkoxy-carbonyl, (x) $C_{1-6}$ alkyl-carbonyl, or (xi) $C_{3-6}$ cycloalkyloxycarbonyl, (6) a group of the formula: —S(O)f—$R^6$, wherein f is an integer of 0 to 2, and $R^6$ represents a hydrogen atom or a hydrocarbon residue which has the same meaning as defined above, and may be substituted with halogen, nitro, cyano, hydroxy, oxo, thioxo, carboxyl, cyano-$C_{6-14}$ aryl, or halogeno-$C_{6-14}$ aryl, (7) a group of the formula: —$NR^9R^{10}$, wherein $R^9$ and $R^{10}$ each is (i) hydrogen, (ii) hydrocarbon residue, which has the same meaning as defined above, (iii) formyl, (iv) $C_{1-6}$ alkanoyl, or (v) a 5- to 13-membered heterocyclic group which is mentioned below, (8) a 5- to 13-membered heterocyclic group containing 1–4 heteroatoms selected from oxygen, sulfur and nitrogen as ring members, the heterocyclic group being optionally substituted by (i) halogen, (ii) $C_{1-4}$ alkyl, (iii) $C_{1-3}$ alkoxy, (iv) $C_{1-4}$ alkylthio, or (v) phenoxy which may optionally be substituted by a halogen, (9) sulfo, (10) $C_{6-14}$ aryl, (11) $C_{3-7}$ cycloalkyl, (12) $C_{1-6}$ alkylenedioxy, (13) oxo, (14) thioxo, (15) $C_{3-4}$ alkynyl, (16) $C_{3-10}$ cycloalkyl, (17) $C_{2-10}$ alkenyl, (18) $C_{7-20}$ aralkyl, (19) amidino, and (20) azido, or (B) a 5- to 13-membered, hetero-aromatic group or non-aromatic saturated or unsaturated heterocyclic group containing 1–4 heteroatoms selected from the group consisting of oxygen, sulfur and nitrogen as ring members which may optionally have the following substituents: (1) halogen, (2) nitro, (3) nitroso, (4) cyano, (5) hydroxyl group which may optionally be substituted by (i) $C_{1-6}$ alkyl which may optionally be substituted by hydroxyl, $C_{1-6}$ alkoxy, $C_{1-3}$ alkoxy-$C_{1-3}$ alkoxy, $C_{1-3}$ alkylthio, carboxyl, carbamoyl, $C_{1-6}$ alkyl-carbamoyl, 5- to 7-membered nitrogen containing heterocyclic group-carbonyl or halogen, (ii) formyl, (iii) $C_{7-20}$ aralkyl which may optionally be substituted by halogen, $C_{1-3}$ alkoxy or $C_{1-4}$ alkyl, (iv) $C_{6-14}$ aryl which may optionally be substituted by halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkyl-amino, (ix) $C_{1-3}$ alkoxy-carbonyl, (x) $C_{1-6}$ alkyl-carbonyl, or (xi) $C_{3-6}$ cycloalkyloxycarbonyl, (6) a group of the formula: —S(O)f—$R^6$, wherein f is an integer of 0 to 2, $R^6$ represents a hydrogen atom or a hydrocarbon residue which may optionally be substituted, the hydrocarbon residue has the same meaning as defined above, which may be substituted with halogen, nitro, cyano, hydroxy, oxo, thioxo, carboxyl, cyano-$C_{6-14}$ aryl, or halogeno-$C_{6-14}$ aryl, (7) a group of the formula: —$NR^9R^{10}$, wherein $R^9$ and $R^{10}$ each is (i) hydrogen, (ii) hydrocarbon residue, which has the same meaning as defined above, (iii) formyl, (iv) $C_{1-6}$ alkanoyl, or (v) a 5- to 13-membered heterocyclic group which is mentioned below, (8) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) a group of the formula: $NR^8R^9$ which is defined above or (ix) an optionally substituted 5- to 13-membered heterocyclic group which is mentioned below, (9) a 5- to 13-membered heterocyclic group containing 1–4 heteroatoms selected from the group consisting of oxygen, sulfur and nitrogen as ring members, the heterocyclic group being optionally substituted by (i) halogen, (ii) $C_{1-4}$ alky, (iii) $C_{1-3}$ alkoxy, (iv) $C_{1-4}$ alkylthio, or (v) phenoxy which may optionally be substituted by a halogen, (10) sulfo, (11) $C_{6-14}$ aryl, (12) $C_{3-7}$ cycloalkyl, (13) $C_{1-6}$ alkylenedioxy, (14) oxo, (15) thioxo, (16) $C_{3-4}$ alkynyl, (17) $C_{3-10}$ cycloalkyl, (18) $C_{2-10}$ alkenyl, (19) $C_{7-20}$ aralkyl, (20) amidino or (21) azido, W is a direct linkage or a spacer group selected from the group consisting of (1) $C_{1-4}$ alkylene, (2) $C_{2-6}$ alkenylene, (3) a group of the formula: —(CH$_2$)$_c$NR$^{10}$—, where c represents an integer of 0–3, $R^{10}$ represents hydrogen or $C_{1-6}$ alkyl, (4) —CO—, (5) a group of the formula: —CONR$^{10}$—, where $R^{10}$ is as defined above, (6) —O—, (7) a group of the formula: —S(O)f—, where f represents an integer of 0 to 2, and (8) a group of the formula: —NR$^{10}$S(O)e—, where e represents an integer of 0–2; $R^{10}$ is as defined above, and n denotes an integer of 1 to 3; or a salt thereof.

3. 2,4(1H,3H)-dioxo-6-(4-methoxymethoxyphenyl)-1-(2-methylthiobenzyl)-5-(methanesulfonamidomethyl)-thieno [2,3-d]pyrimidine-3-acetic acid or its salt.

4. 2,4(1H,3H)-dioxo-6-(4-methoxymethoxyphenyl)-1-(2-methylthiobenzyl)-5-(ethanesulfonamidomethyl)-thieno[2,3-d]pyrimidine-3-acetic acid or its salt.

5. 2,4 (1H,3H)-dioxo-6-(4-methoxyphenyl)-1-(2-methylthio-benzyl)-5-(methanesulfonamidomethyl)-thieno [2,3-d]pyrimidine-3-acetic acid or its salt.

6. Ethyl 2,4(1H,3H)-dioxo-6-(4-methoxyphenyl)-1-(2-methylthiobenzyl)-5-(carboxymethyl)thieno[2,3-d] pyrimidine-3-acetate.

7. A method for antagonizing endothelin activity in a mammal comprising administering an effective amount of the compound according to claim 1 to the mammal wherein the mammal suffers from an endothelin-derived disorder selected from the group consisting of acute renal insufficiency, myocardial infarction and liver insufficiency.

8. A method according to claim 7, wherein the endothelin-derived disorder is a liver hypofunction caused by surgery or transplant.

9. A pharmaceutical composition, which comprises a compound as defined in claim 2 and a carrier, excipient or diluent therefor.

10. A method for antagonizing endothelin activity in a mammal comprising administering an effective amount of the pharmaceutical composition according to claim 9 to the mammal wherein the mammal suffers from an endothelin-derived disorder selected from the group consisting of acute renal insufficiency, cardiac infarction and liver insufficiency.

11. A method for antagonizing endothelin activity in a mammal according to claim 10, wherein the mammal suffers from an endothelin-derived liver hypofunction caused by surgery or transplant.

12. A method for treating a mammal suffering from vasoconstriction, which comprises administering an effective amount of a compound as defined in claim 2 to the mammal.

13. A method for treating a mammal suffering from acute renal insufficiency, cardiac infarction or liver insufficiency, which comprises administering an effective amount of a compound as defined in claim 2 to the mammal.

14. A pharmaceutical composition, which comprises a compound as defined in claim 1, and a carrier, excipient, or diluent therefore.

15. A compound according to claim 2, wherein $R^4$ is a $C_{6-14}$ aryl group which may optionally have (1) halogen, (2) nitro, (3) nitroso, (4) cyano, (5) hydroxyl group which may optionally be substituted by (i) $C_{1-6}$ alkyl which may optionally be substituted by hydroxyl, $C_{1-6}$ alkoxy, $C_{1-3}$ alkoxy- $C_{1-3}$ alkoxy, $C_{1-3}$ alkylthio, carboxyl, carbamoyl, $C_{1-6}$ alkyl-carbamoyl, 5- to 7-membered nitrogen containing heterocyclic group-carbonyl or halogen, (ii) formyl, (iii) $C_{7-20}$ aralkyl which may optionally be substituted by halogen, $C_{1-3}$ alkoxy or $C_{1-4}$ alkyl, (iv) $C_{6-14}$ aryl which may optionally be substituted by halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkylamino (ix) $C_{1-3}$ alkoxy-carbonyl, (x) $C_{1-6}$ alkyl-carbonyl, or (xi) $C_{3-6}$ cycloalkyloxycarbonyl, (6) a group of the formula: —S(O)f—$R^6$, which is defined in claim 2, (7) a group of the formula: —$NR^9R^{10}$ which is defined in claim 2, (8) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) a group of the formula: —$NR^9R^{10}$ which is defined above or (ix) an optionally substituted 5- to 13-membered heterocyclic group which is mentioned below, (9) a 5- to 13-membered heterocyclic group containing 1–4 heteroatoms selected from oxygen, sulfur and nitrogen as ring members, the heterocyclic group being optionally substituted by (i) halogen, (ii) $C_{1-4}$ alkyl, (iii) $C_{1-3}$ alkoxy, (iv) $C_{1-4}$ alkylthio, or (v) phenoxy which may optionally be substituted by a halogen, (10) sulfo, (11) $C_{6-14}$ aryl, (12) $C_{3-7}$ cycloalkyl, (13) $C_{1-6}$ alkylenedioxy, (14) oxo, (15) thioxo, (16) $C_{2-4}$ alkenyl, (17) $C_{3-4}$ alkynyl, (18) $C_{3-10}$ cycloalkyl, (19) $C_{2-10}$ alkenyl, (20) $C_{7-20}$ aralkyl, (21) amidino, and (22) azido.

16. A compound according to claim 1, wherein $R^4$ is a $C_{1-20}$ hydrocarbon residue optionally substituted with (1) halogen, (2) nitro, (3) cyano, (4) $C_{1-6}$ alkoxy which may optionally be substituted by $C_{1-6}$ alkoxy, carboxyl, halogen, $C_{1-6}$ alkyl-carbamoyl or 5 to 7 membered nitrogen-containing heterocyclic group-carbonyl, (5) $C_{7-13}$ aralkyloxy, (6) $C_{1-4}$ alkyl which may be substituted by $C_{1-3}$ alkoxy, (7) $C_{1-6}$ alkanoyl, (8) $C_{1-4}$ alkylthio, (9) $C_{2-6}$ alkenyloxy, (10) $C_{1-6}$ alkoxy-carbonyl or (11) $C_{1-6}$ alkyl-carbamoyl.

17. A compound according to claim 1, wherein $R^4$ is a $C_{1-20}$ hydrocarbon residue optionally substituted with $C_{1-6}$ alkoxy which may optionally be substituted by $C_{1-6}$ alkoxy, carboxyl, halogen, $C_{1-6}$ alkyl-carbamoyl or a 5 to 7 membered nitrogen-containing heterocyclic group-carbonyl.

18. A compound according to claim 1, wherein Q' is $C_{6-14}$ aryl which may be substituted by a group of the formula: —A—$R^5$ (in which A is a chemical bond or a connecting group selected from the group consisting of (1) $C_{1-4}$ alkylene, (2) $C_{1-6}$ alkenylene, (3) —$(CH_2)_cNR^{10}$— (in which c is an integer of 0–3 and $R^{10}$ is hydrogen or $C_{1-6}$ alkyl), (4) —CO—, (5) a group of the formula: —$CONR^{10}$— (in which $R^{10}$ has the same meaning as defined above), (6) —O—, (7) —S—, and (8) a group of the formula: —$NR^{10}SO_e$— (in which e is an integer of 0–2 and $R^{10}$ has the same meaning as defined above; and $R^5$ is $C_{1-6}$ alkyl).

19. A compound according to claim 1, wherein $R^{1'}$ is benzyl which may be substituted by a group of the formula: —A—$R^5$: (wherein A is a chemical bond or a connecting group selected from the group consisting of (1) $C_{1-4}$ alkylene, (2) $C_{1-6}$ alkenylene, (3) —$(CH_2)_cNR^{10}$— (in which c is an integer of 0–3 and $R^{10}$ is hydrogen or $C_{1-6}$ alkyl), (4) —CO—, (5) a group of the formula: —$CONR^{10}$— (in which $R^{10}$ has the same meaning as defined above), (6) —O—, (7) —S—, and (8) a group of the formula: —$NR^{10}SO_e$— (in which e is an integer of 0–2 and $R^{10}$ has the same meaning as defined above; and $R^5$ is $C_{1-6}$ alkyl).

20. A compound according to claim 1, wherein $R^2$ is hydrogen or $C_{1-6}$ alkyl.

21. A compound according to claim 20, wherein $R^2$ is hydrogen.

22. A compound according to claim 1, wherein $R^3$ is hydrogen, $C_{1-6}$ alkyl or amino which may be mono- or di-substituted by $C_{1-4}$ alkyl or $C_{6-12}$ aryl.

23. A compound according to claim 1, wherein $R^3$ is $C_{1-6}$ alkyl.

24. A compound according to claim 1, wherein is $R^4$ is $C_{6-14}$ aryl which may be substituted with one to three substituents selected from the group consisting of $C_{1-3}$ alkyl, $C_{2-4}$ alkenyl, $C_{3-4}$ alkynyl, $C_{3-7}$ cycloalkyl, phenyl, naphthyl, a 5- to 9-membered aromatic heterocyclic group having 1–4 heteroatoms selected from nitrogen, oxygen and sulfur, a 5- to 9-membered non-aromatic heterocyclic group having 1–4 heteroatoms selected from nitrogen, oxygen and sulfur, aralkyl having 7–10 carbons, amino, monoalkylamino having 1–6 carbons, N,N-disubstituted amino wherein the substituents are alykl having 2–6 carbons, amidino, $C_{1-8}$ alkyl-carbonyl, $C_{6-14}$ aryl-carbonyl, carbamoyl, $C_{1-6}$ alkyl-carbamoyl, N,N-disubstituted carbamoyl substituted with alkyl having 1–6 carbons, sulfamoyl, N-alkylsulfamoyl substituted with alkyl having 1–6 carbons, N,N-disubstituted sulfamoyl substituted with alkyl having 1–6 carbons, carboxyl, $C_{1-3}$ alkoxy-carbonyl, hydroxyl, optionally-substituted alkoxy having 1–3 carbons which may be substituted with $C_{1-3}$ lower alkyl, halogen, $C_{1-3}$ alkylthio or hydroxyl, alkenyloxy having 2–4 carbons, cycloalkyloxy having 3–7 carbons, aralkyloxy having 7–10 carbons, phenyloxy, naphthyloxy, mercapto, alkylthio having 1–3 carbons, aralkylthio having 7–10 carbons, phenylthio, naphthylthio, alkylenedioxy having 1–3 carbons, sulfo, cyano, azido, nitro, nitroso and a halogen atom.

25. A compound according to claim 1, wherein $R^{4'}$ is $C_{6-12}$ aryl which may be substituted by $C_{1-6}$ alkoxy or $C_{1-6}$ alkylthio.

26. A compound according to claim 1, wherein W is a spacer group selected from the group consisting of (1) $C_{1-4}$ alkylene, (2) $C_{2-6}$ alkenylene, (3) a group of the formula —$(CH_2)cNR^{10}$—, where c represents an integer of 0–3, $R^{10}$ represents hydrogen or $C_{1-6}$ alkyl, (4) —CO—, (5) a group of the formula —$CONR^{10}$—, where $R^{10}$ is as defined above, (6) —O—, (7) a group of the formula: —S(O)f—, where f represents an integer of 0 to 2, and (8) a group of the formula: —$NR^{10}S(O)e$—, where e represents an integer of 0–2; $R^{10}$ is as defined above.

27. A compound according to claim 1, wherein the compound is selected from the group consisting of 2,4(1H,3H)-dioxo-5-methyl-6-(4-methoxymethoxyphenyl)-1-(2-methoxybenzyl)thieno[2,3-d]pyrimidine-3-acetic acid, 2,4(1H,3H)-dioxo-5-methyl-6-(4-methoxyphenyl)-1-(2-methylthiobenzyl)thieno[2,3-d]pyrimidine-3-acetic acid, 2,4(1H,3H)-dioxo-5-methyl-6-(4-methoxymethoxyphenyl)-1-(2-methylthiobenzyl)thieno[2,3-d]pyrimidine-3-acetic acid, 2,4(1H,3H)-dioxo-5-methyl-6-(4-methylthiomethoxyphenyl)-1-(2-methylthiobenzyl)thieno[2,3-d]pyrimidine-3-acetic acid, 2,4(1H,3H)-dioxo-5-methyl-6-(4-methylthiomethoxyphenyl)-1-(2-methoxybenzyl)thieno[2,3-d]pyrimidine-3-acetic acid, 2,4(1H,3H)-dioxo-5-methyl-1-(2-methylthiobenzyl)-6-(4-propoxyphenyl)thieno[2,3-d]pyrimidine-3-acetic acid and 2,4(1H,3H)-dioxo-5-methyl-1-(2-methylthiobenzyl)-6-[4-(2-oxopropoxy)phenyl]thieno[2,3-d]pyrimidine-3-acetic acid.

28. A compound according to claim 1, wherein W is a chemical bond.

29. A compound according to claim 2, wherein $R^1$ is a benzyl group which may optionally be substituted by (1) halogen or (2) $C_{1-4}$ alkylthio,
$R^2$ is a hydrogen atom or a $C_{1-4}$ alkyl group which may optionally be substituted by (1) $C_{1-6}$ alkyl-carbonyloxy or (2) $C_{3-6}$ cycloalkyl-oxycarbonyloxy,
$R^3$ is a $C_{1-6}$ alkyl group which is substituted by (1) a $C_{1-6}$ alkoxy-carbonyl group or (2) a group of the formula: —NH—SO$_2$—$R^{5''}$ (wherein $R^{5''}$ is (1) a $C_{1-3}$ alkyl group which may optionally be substituted by halogen or (2) a phenyl group),
$R^4$ is a phenyl group which is substituted by (1) $C_{1-4}$ alkoxy which may be substituted by $C_{1-6}$ alkoxy, carboxyl, $C_{1-6}$alkyl-carbamoyl, piperazinecarbonyl or halogen, (2) $C_{7-8}$ aralkyloxy, (3) $C_{1-4}$ alkyl which may be substituted by $C_{1-3}$ alkoxy, (4) $C_{1-6}$ alkanoyl, (5) $C_{2-4}$ alkenyloxy, (6) $C_{1-6}$ alkoxy-carbonyl or (7) $C_{1-6}$ carbamoyl, and W is a chemical bond.

30. A method according to claim 2, wherein the vasoconstriction is in a coronary artery, coronary vein, cerebrovascular system or pulmonary vascular system.

31. A compound according to claim 2, wherein $R^3$ is a $C_{1-6}$ alkyl group which is substituted by a group of the formula: —NH—SO$_2$—$R^5$, wherein $R^5$ is (1) a $C_{1-6}$ alkyl group which may optionally be substituted by halogen or (2) a $C_{6-14}$ aryl group.

32. A compound according to claim 2, wherein $R^3$ is a $C_{1-6}$ alkyl group which is substituted by a group of the formula: —NH—SO$_2$—$R^{5'}$, wherein $R^{5'}$ is a $C_{1-6}$ alkyl group or a $C_{6-14}$ aryl group.

33. A compound according to claim 2, wherein $R^2$ is a $C_{1-20}$ hydrocarbon residue optionally substituted with (1) halogen, (2) nitro, (3) hydroxyl, (4) cyano, (5) $C_{1-4}$ alkylthio, (6) $C_{1-4}$ alkoxy, (7) $C_{1-6}$ alkyl-carbonyloxy or (8) $C_{3-6}$ cycloalkyl-oxycarbonyl.

34. A compound according to claim 2, wherein $R^2$ is hydrogen or a $C_{1-6}$ alkyl group which may be optionally substituted by $C_{1-6}$ alkyl-carbonyloxy or $C_{3-6}$ cycloalkyl-oxycarbonyloxy.

35. A compound according to claim 2, wherein $R^3$ is a $C_{1-6}$ alkyl group which is substituted by a $C_{1-6}$ alkoxy-carbonyl group or a group of the formula: —NH—SO$_2$—$R^{5'}$, wherein $R^{5'}$ is a $C_{1-6}$ alkyl group or a $C_{6-14}$ aryl group.

36. A compound according to claim 2, wherein $R^2$ is $C_{1-10}$ alkyl, $C_{3-10}$ cycloalkyl, $C_{2-10}$ alkenyl, $C_{6-14}$ aryl or $C_{7-20}$ aralkyl any of which may optionally have following substituents: (1) halogen, (2) nitro, (3) nitroso, (4) cyano, (5) hydroxyl group which may optionally be substituted by (i) $C_{1-6}$ alkyl which may optionally be substituted by hydroxyl, $C_{1-6}$ alkoxy, $C_{1-3}$ alkoxy-$C_{1-3}$ alkoxy, $C_{1-3}$ alkylthio, carboxyl, carbamoyl, $C_{1-6}$ alkyl-carbamoyl, 5- to 7-membered nitrogen containing heterocyclic group-carbonyl or halogen, (ii) formyl, (iii) $C_{7-20}$ aralkyl, which may optionally be substituted by halogen, $C_{1-3}$ alkoxy or $C_{1-4}$ alkyl, (iv) $C_{6-14}$ aryl which may optionally be substituted by halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkylamino, (ix) $C_{1-3}$ alkoxy-carbonyl, (x) $C_{1-6}$ alkyl-carbonyl, or (xi) $C_{3-6}$ cycloalkyloxycarbonyl, (6) a group of the formula: —S(O)f—$R^6$ which is defined in claim 2, (7) a group of the formula: —NR$^9$R$^{10}$ which is defined in claim 2, (8) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) a group of the formula: NR$^9$NR$^{10}$ which is defined above or (ix) an optionally substituted 5- to 13-membered heterocyclic group which is mentioned below, (9) a 5- to 13-membered heterocyclic group containing 1–4 heteroatoms selected from oxygen, sulfur and nitrogen as ring members, the heterocyclic group being optionally substituted by (i) halogen, (ii) $C_{1-4}$ alkyl, (iii) $C_{1-3}$ alkoxy, (iv) $C_{1-4}$ alkylthio, or (v) phenoxy which may optionally be substituted by a halogen, (10) sulfo, (11) $C_{6-14}$ aryl, (12) $C_{3-7}$ cycloalkyl, (13) $C_{1-6}$ alkylenedioxy, (14) oxo, (15) thioxo, (16) $C_{2-4}$ alkenyl, (17) $C_{3-4}$ alkynyl, (18) $C_{3-10}$ cycloalkyl, (19) $C_{2-10}$ alkenyl, (20) $C_{7-20}$ aralkyl, (21) amidino, and (22) azido.

37. A compound according to claim 2, wherein $R^2$ is a $C_{1-10}$ alkyl which may optionally have (1) halogen, (2) nitro, (3) nitroso, (4) cyano, (5) hydroxyl group which may optionally be substituted by (i) $C_{1-6}$ alkyl which may optionally be substituted by hydroxyl, $C_{1-6}$ alkoxy, $C_{1-3}$ alkoxy-$C_{1-3}$ alkoxy, $C_{1-3}$ alkylthio, carboxyl, carbamoyl, $C_{1-6}$ alkyl-carbamoyl, 5- to 7-membered nitrogen containing heterocyclic group-carbonyl or halogen, (ii) formyl, (iii) $C_{7-20}$ aralkyl which may optionally be substituted by halogen, $C_{1-3}$ alkoxy or $C_{1-4}$ alkyl, (iv) $C_{6-14}$ aryl which may optionally be substituted by halogen, (v) $C_{2-6}$ alkenyl, (vi) $C_{3-7}$—cycloalkyl, (vii) $C_{1-3}$ alkoxy-carbonyl, (viii) mono- or di-$C_{1-6}$ alkylamino, (ix) $C_{1-3}$ alkoxy-carbonyl, (x) $C_{1-6}$ alkyl-carbonyl $C_{1-6}$ or (xi) $C_{3-6}$ cycloalkyloxycarbonyl, (6) a group of the formula: —S(O)f—$R^6$, which is defined in claim 2, (7) a group of the formula: —NR$^9$R$^{10}$, which is defined in claim 2, (8) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) a group of the formula: NR$^9$R$^{10}$ which is defined above or (vix) an optionally substituted 5- to 13-membered heterocyclic group which is mentioned below, (9) a 5- through 13-membered heterocyclic group containing 1–4 heteroatoms selected from oxygen, sulfur and nitrogen as ring members, the heterocyclic group being optionally substituted by (i) halogen, (ii) $C_{1-4}$ alkyl, (iii) $C_{1-3}$ alkoxy, (iv) $C_{1-4}$ alkylthio, and (v) phenoxy which may optionally be substituted by a halogen, (10) sulfo, (11) $C_{6-14}$ aryl, (12) $C_{3-7}$ cycloalkyl, (13) $C_{1-6}$ alkylenedioxy, (14) oxo, (15) thioxo, (16) $C_{2-4}$ alkenyl, (17) $C_{3-4}$ alkynyl, (18) $C_{3-10}$ cycloalkyl, (19) $C_{2-10}$ alkenyl, (20) $C_{7-20}$ aralkyl, (21) amidino, and (22) azido.

38. A compound according to claim 2, wherein $R^2$ is a $C_{1-20}$ hydrocarbon residue optionally substituted with (a) halogen, (b) nitro, (c) cyano, (d) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) a group of the formula: NR$^9$R$^{10}$ which is defined in claim 2, or (ix) an optionally substituted 5- to 13-membered heterocyclic group which is mentioned in claim 2, (e) a group of the formula: —S(O) f—$R^6$, wherein f denotes an integer of 0 to 2, and $R^6$ is a hydrogen atom or a hydrocarbon residue, selected from the group consisting of $C_{1-10}$ alkyl, $C_{3-10}$ cycloalkyl, $C_{7-10}$ bicycloalkyl, $C_{2-10}$ alkenyl, $C_{6-14}$ aryl, and $C_{7-20}$ aralkyl each of which may optionally have (1) halogen, (2) nitro, (3) nitroso, (4) cyano, (5) hydroxyl group which may optionally be substituted by (i) $C_{1-6}$ alkyl which may optionally be substituted by hydroxyl, $C_{1-6}$ alkoxy, $C_{1-3}$ alkoxy-$C_{1-3}$ alkoxy, $C_{1-3}$ allylthio, carboxyl, carbamoyl, $C_{1-6}$ alkyl-carbamoyl, 5- to 7-membered nitrogen containing heterocyclic group-carbonyl or halogen, (ii) formyl, (iii) $C_{7-20}$ aralkyl, which may optionally be substituted by halogen, $C_{1-3}$ alkoxy or $C_{1-4}$ alkyl, (iv) $C_{6-14}$ aryl which may optionally be substituted by halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkyl-amino, (ix) $C_{1-3}$ alkoxy-carbonyl, (x) $C_{1-6}$ alkyl-carbonyl, or (xi) $C_{3-6}$ cycloalkyloxycarbonyl, (6) a group of the formula: —S(O)f—$R^6$, wherein f is an integer of 0 to 2, $R^6$ represents a hydrogen atom or a hydrocarbon residue which may optionally be substituted, the hydrocarbon residue has the same meaning as defined above, which may be substituted with halogen, nitro, cyano, hydroxy, oxo, thioxo, carboxyl, cyano-$C_{6-14}$ aryl, or halogeno-$C_{6-14}$ aryl, (7) a group of the formula: —$NR^9R^{10}$ which is defined above, (8) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) a group of the formula: —$NR^9R^{10}$ which is defined above or (ix) an optionally substituted 5- to 13-membered heterocyclic group which is mentioned below, (9) a 5- to 13-membered heterocyclic group containing 1–4 heteroatoms selected from oxygen, sulfur and nitrogen as ring members, the heterocyclic group being optionally substituted by (i) halogen, (ii) $C_{1-4}$ alkyl, (iii) $C_{1-3}$ alkoxy, (iv) $C_{1-4}$ alkylthio, (v) phenoxy which may optionally be substituted by a halogen, (10) sulfo, (11) $C_{6-14}$ aryl, (12) $C_{3-7}$ cycloalkyl, (13) $C_{1-6}$ alkylenedioxy, (14) oxo, (15) thioxo, (16) $C_{2-4}$ alkenyl, (17) $C_{3-4}$ alkynyl, (18) $C_{3-10}$ cycloalkyl, (19) $C_{2-10}$ alkenyl, (20) $C_{7-20}$ aralkyl, (21) amidino, and (22) azido, (f) a group of the formula: —$NR^9R^{10}$ as defined above, or (g) 5- or 6-membered heterocyclic group which contains 1 to 4 heteroatom(s) of oxygen, sulfur or nitrogen as ring members wherein the heterocyclic group is optionally substituted by (i) halogen, (ii) $C_{1-4}$ alkyl, (iii) $C_{1-3}$ alkoxy, (iv) $C_{1-4}$ alkylthio, or (v) phenoxy which may optionally be substituted by a halogen.

39. A compound according to claim 2, wherein R' is a $C_{1-10}$ alkyl, $C_{3-10}$ cycloalkyl, $C_{2-10}$ alkenyl, $C_{6-14}$ aryl or $C_{7-20}$ aralkyl group.

40. A compound according to claim 2, wherein $R^1$ is a $C_{7-20}$ aralkyl group which may optionally have the following substituents: (1) halogen, (2) nitro, (3) nitroso, (4) cyano, (5) hydroxyl group which may optionally be substituted by (i) $C_{1-6}$ alkyl which may optionally be substituted by hydroxyl, $C_{1-6}$ alkoxy, $C_{1-3}$ alkoxy-$C_{1-3}$ alkoxy, $C_{1-3}$ alkylthio, carboxyl, carbamoyl, $C_{1-6}$ alkyl-carbamoyl, 5- to 7-membered nitrogen containing heterocyclic group-carbonyl or halogen, (ii) formyl, (iii) $C_{7-20}$ aralkyl which may optionally be substituted by halogen, $C_{1-3}$ alkoxy or $C_{1-4}$ alkyl, (iv) $C_{6-14}$ aryl which may optionally be substituted by halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkylamino, (ix) $C_{1-3}$ alkoxy-carbonyl, (x) $C_{1-6}$ alkyl-carbonyl, or (xi) $C_{3-6}$ cycloalkyloxycarbonyl, (6) a group of the formula: —S(O)f—$R^6$, wherein f is an integer of 0 to 2, $R^6$ represents a hydrogen atom or a hydrocarbon residue which may optionally be substituted, the hydrocarbon residue has the same meaning as in claim 37, which may be substituted with halogen, nitro, cyano, hydroxy, oxo, thioxo, carboxyl, cyano-$C_{6-14}$ aryl, or halogeno-$C_{6-14}$ aryl, (7) a group of the formula: —$NR^9R^{10}$, wherein $R^9$ and $R^{10}$ each is hydrogen, hydrocarbon residue, which has the same meaning as defined above, formyl or a 5- to 13-membered heterocyclic group which is mentioned below, (8) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloallyl, (vi) $C_{6-14}$ aryl, (vii) $C_{7-20}$ aralkyl, (viii) a group of the formula: $NR^9R^{10}$ which is defined above or (ix) an optionally substituted 5- to 13-membered heterocyclic group which is mentioned below, (9) a 5- to 13-membered heterocyclic group containing 1–4 heteroatoms selected from oxygen, sulfur and nitrogen as ring members, the heterocyclic group being optionally substituted by (i) halogen, (ii) $C_{1-4}$ alkyl, (iii) $C_{1-3}$ alkoxy, (iv) $C_{1-4}$ alkylthio, (v) phenoxy which may optionally be substituted by a halogen, (10) sulfo, (11) $C_{6-14}$ aryl, (12) $C_{3-7}$ cycloalkyl, (13) $C_{1-6}$ alkylenedioxy, (14) oxo, (15) thioxo, (16) $C_{3-4}$ alkynyl, (17) $C_{3-10}$ cycloalkyl, (18) $C_{2-10}$ alkenyl, (19) $C_{7-20}$ aralkyl, (20) amidino, and (21) azido.

41. A compound according to claim 2, wherein $R^1$ is a $C_{7-20}$ hydrocarbon residue optionally substituted with (a) halogen, (b) nitro, (c) cyano, (d) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) a group of the formula: $NR^9R^{10}$ which is defined in claim 37 or (ix) an optionally substituted 5- to 13-membered heterocyclic group which is mentioned below, (e) a group of the formula: —S(O)f—$R^6$, wherein f denotes an integer of 0 to 2, and $R^6$ is a hydrogen atom or an optionally substituted hydrocarbon residue selected from the group consisting of $C_{1-10}$ alkyl, $C_{3-10}$ cycloalkyl, $C_{7-10}$ bicycloalkyl, $C_{2-10}$ alkenyl, $C_{6-14}$ aryl, and $C_{7-20}$ aralkyl each of which may optionally have (1) halogen, (2) nitro, (3) nitroso, (4) cyano, (5) hydroxyl group which may optionally be substituted by (i) $C_{1-6}$ alkyl which may optionally be substituted by hydroxyl, $C_{1-6}$ alkoxy, $C_{1-3}$ alkoxy-$C_{1-3}$ alkoxy, $C_{1-3}$ alkylthio, carboxyl, carbamoyl, $C_{1-6}$ alkyl-carbamoyl, 5- to 7-membered nitrogen containing heterocyclic group-carbonyl or halogen, (ii) formyl or $C_{1-6}$ alkanoyl, (ill) $C_{7-20}$ aralkyl which may optionally be substituted by halogen, $C_{1-3}$ alkoxy or $C_{1-4}$ alkyl, (iv) $C_{6-14}$ aryl which may optionally be substituted by halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkylamino, (ix) $C_{1-3}$ alkoxy-carbonyl, (x) $C_{1-6}$ alkyl-carbonyl, or (xi) $C_{3-6}$ cycloalkyloxycarbonyl, (6) a group of the formula: —S(O)f—$R^6$, wherein f is an integer of 0 to 2, $R^6$ represents a hydrogen atom or a hydrocarbon residue which may optionally be substituted, the hydrocarbon residue has the same meaning as defined above, which may be substituted with halogen, nitro, cyano, hydroxy, oxo, thioxo, carboxyl, cyano-$C_{6-14}$ aryl, or halogeno-$C_{6-14}$ aryl, (7) a group of the formula: —$NR^9R^{10}$ which is defined above, (8) a group of the formula: —CO—$R^{11}$ wherein $R^{11}$ denotes (i) hydrogen, (ii) hydroxyl, (iii) $C_{1-6}$ alkyl, (iv) $C_{1-6}$ alkoxy, (v) $C_{3-6}$ cycloalkyl, (vi) $C_{6-14}$ aryl, (vii) $C_{7-20}$ aralkyl, (viii) a group of the formula: $NR^9R^{10}$ which is defined above or (vix) an optionally substituted 5- to 13-membered heterocyclic group which is mentioned below, (9) a 5- to 13-membered heterocyclic group containing 1–4 heteroatoms selected from oxygen, sulfur and nitrogen as ring members, the heterocyclic group being optionally substituted by (i) halogen, (ii) $C_{1-4}$ alkyl, (iii) $C_{1-3}$ alkoxy, (iv) $C_{1-4}$ alkylthio, (v) phenoxy which may optionally be substituted by a halogen, (10) sulfo, (11) $C_{6-14}$ aryl, (12) $C_{3-7}$ cycloalkyl, (13) $C_{1-6}$ alkylenedioxy, (14) oxo, (15) thioxo, (16) $C_{2-4}$ alkenyl, (17) $C_{3-4}$ alkynyl, (18) $C_{3-10}$ cycloalkyl, (19) $C_{2-10}$ alkenyl, (20) $C_{7-20}$ aralkyl, (21) amidino, and (22) azido, (f) a group of the formula: —$NR^9R^{10}$ defined above, or (g) an optionally substituted 5- or 6-membered heterocyclic group which contains 1 to 4 heteroatom(s) of oxygen, sulfur or nitrogen as ring members wherein the heterocyclic group is optionally substituted by (i) halogen, (ii) $C_{1-4}$ alkyl, (iii) $C_{1-3}$ alkoxy, (iv) $C_{1-4}$ alkylthio, or (v) phenoxy which may optionally be substituted by a halogen.

42. A compound according to claim 2, wherein $R^1$ is a $C_{7-20}$ hydrocarbon residue optionally substituted with halogen or a $C_{1-4}$ alkylthio group.

* * * * *

UNITED STATES PATENT AND TRADEMARK OFFICE
CERTIFICATE OF CORRECTION

PATENT NO. : 6,140,325
DATED : October 31, 2000
INVENTOR(S) : Furuya, et al.

It is certified that error appears in the above-identified patent and that said Letters Patent is hereby corrected as shown below:

<u>Title page,</u>
Item [30], Foreign Application Priority Data, delete "August 19, 1993" should read -- August 26, 1993 --.

Signed and Sealed this

Thirtieth Day of October, 2001

Attest:

NICHOLAS P. GODICI
Attesting Officer    Acting Director of the United States Patent and Trademark Office